(12) United States Patent
Leblond et al.

(10) Patent No.: US 8,168,631 B2
(45) Date of Patent: May 1, 2012

(54) 3-(4-FLUOROPHENYL)-3-HYDROXY-2-AMINO-PROPIONIC ACID AMIDES AND RELATED COMPOUNDS HAVING ANALGESIC ACTIVITY

(75) Inventors: Bertrand Leblond, Paris (FR); Eric Beausoleil, Paris (FR); Thierry Taverne, Paris (FR); John E. Donello, Dana Point, CA (US); Rong Yang, Mission Viejo, CA (US); Cédric Chauvignac, Montrouge (FR)

(73) Assignee: Allergan, Inc., Irvine, CA (US)

( * ) Notice: Subject to any disclaimer, the term of this patent is extended or adjusted under 35 U.S.C. 154(b) by 197 days.

(21) Appl. No.: 12/364,930

(22) Filed: Feb. 3, 2009

(65) Prior Publication Data

US 2009/0281085 A1    Nov. 12, 2009

Related U.S. Application Data

(60) Provisional application No. 61/026,178, filed on Feb. 5, 2008.

(51) Int. Cl.
| | |
|---|---|
| A61K 31/40 | (2006.01) |
| A61K 31/426 | (2006.01) |
| A61K 31/4453 | (2006.01) |
| A61K 31/5375 | (2006.01) |
| A61K 31/165 | (2006.01) |

(52) U.S. Cl. .............. 514/228.8; 514/330; 514/365; 514/423; 514/620; 544/163; 546/226; 548/200; 548/540; 564/167

(58) Field of Classification Search .......... 548/540, 548/200; 514/228.8, 330, 365, 423, 620; 546/226; 544/163; 564/167
See application file for complete search history.

(56) References Cited

U.S. PATENT DOCUMENTS

| | | |
|---|---|---|
| 5,945,442 A | 8/1999 | Shayman |
| 5,952,370 A | 9/1999 | Shayman |
| 6,030,995 A | 2/2000 | Shayman |
| 6,051,598 A | 4/2000 | Shayman |
| 7,687,435 B2 | 3/2010 | Witschel et al. |
| 2003/0050299 A1 | 3/2003 | Hirth |
| 2003/0153768 A1 | 8/2003 | Hirth |
| 2007/0142230 A1 | 6/2007 | Witschel et al. |

FOREIGN PATENT DOCUMENTS

| | | |
|---|---|---|
| WO | WO 2006/081273 | 8/2006 |
| WO | WO2008-011478 A2 | 1/2008 |

OTHER PUBLICATIONS

Soloshonok et al. Tetrahedron, 1996, 52(1), 245-254.*
U.S. Appl. No. 11/814,604, filed Jul. 24, 2007.
Dixon WJ.: Efficient Analysis of Experimental Observations. Annu Rev Pharmacol Toxicol 1980; 20: 441-461.
Kurosawa, Motohiro; et al.: 14C-labeling of a novel atypical β-adrenoceptor agonist, SM-11044. Journal of Labelled Compounds & Radiopharmaceuticals (1996), 38(3), 285-97.
Kim SH, Chung JM.: An Experimental Model for Peripheral Neuropathy Produced by Segmental Spinal Nerve Ligation in the Rat. Pain 1992; 50(3): 355-363.
Oehike, J.; et al.: Synthesis of the Tritium Labelled β-Casomorphine Analogues 3H-PHE-PRO-GLY-OH and 3H2-TYR-PRO-3H-PHE-Pyrrolidide. Journal of Labelled Compounds and Radiopharmaceuticals. vol. 29, No. 12, 1991. pp. 1265-1276.
SciFinder, Nov. 7, 2007.
Silverman, Richard B.: Prodrugs and Drug Delivery Systems, Organic Chemistry of Drug Design and Drug Action, 2d Ed., Elsevier Academic Press: Amsterdam, 2004, pp. 496-557.
PCT-International Search Report, May 13, 2009.
Sloshonok, V.A., et al., << Gold(I)-Catalyzed Asymmetric Aldol Reactions of Fluorinated Benzaldeydes with an α-Isocyanoacetamide, Tetrahedron: Asymmetry, vol. 5, No. 6, 1994, pp. 1091-1094 (XP-002525821).

* cited by examiner

*Primary Examiner* — Jason M Nolan
(74) *Attorney, Agent, or Firm* — Joel B. German; Krishna G. Banerjee

(57) ABSTRACT

Compounds according to the formula below are disclosed herein:

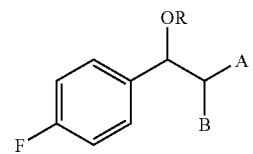

Therapeutic methods, compositions, and medicaments related thereto are also disclosed.

21 Claims, 7 Drawing Sheets

Figure 1: Separation of racemate Compound 1 on Chiralpak® IA
Description:
Chiralpak® IA, hexane:ethanol = 80:20, 220 nm UV+ polarimetry, 1 mL/min
Sample Name: racemate Compound 1
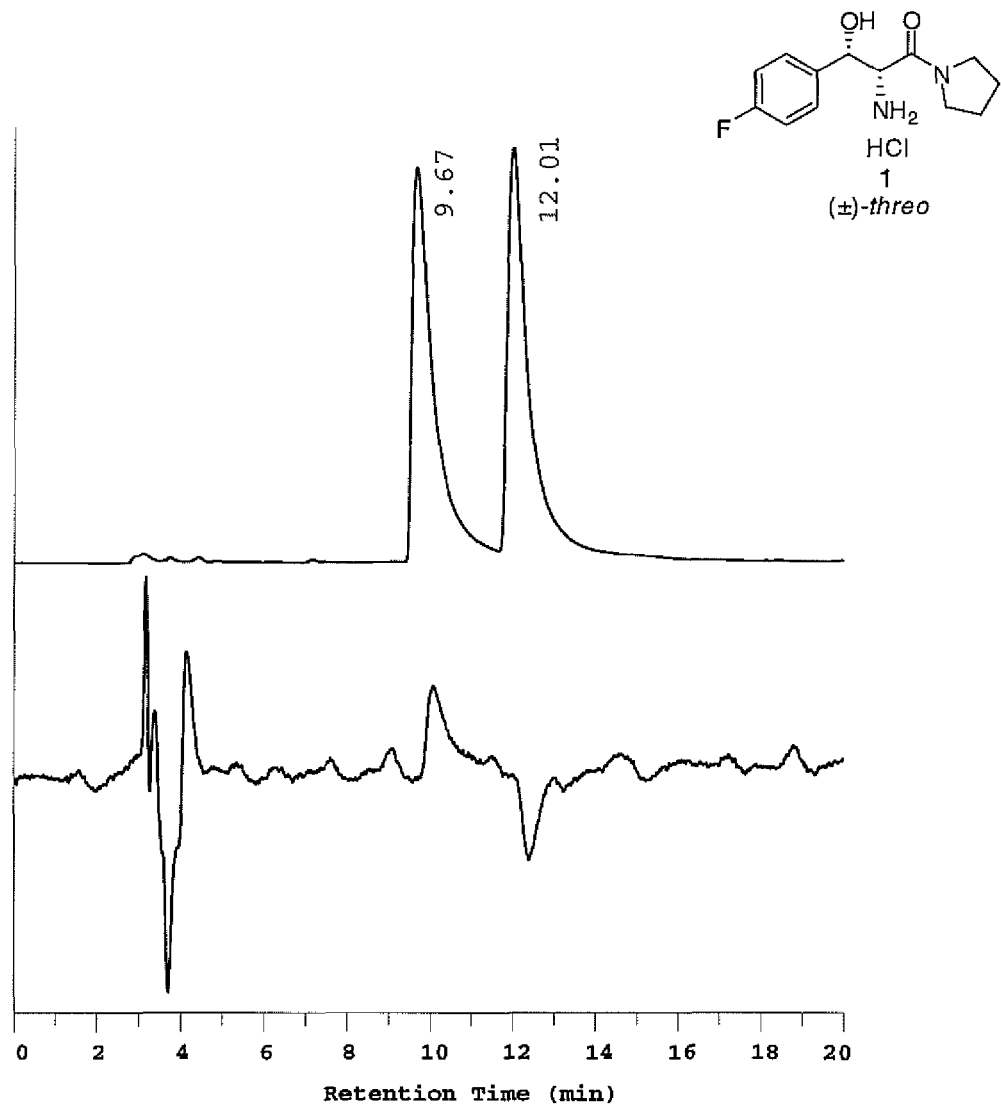
| No. | RT | Area | Conc 1 | BC |
|---|---|---|---|---|
| 1 | 9.67 | 14931886 | 49.741 | MC |
| 2 | 12.01 | 15087297 | 50.259 | MC |
|  |  | 30019183 | 100.000 |  |

Figure 2: Enantiomeric purity of the (+) enantiomer – Compound 2
Description:
Chiralpak® IA, hexane:ethanol = 80:20, 220 nm UV+ polarimetry, 1 mL/min
Sample Name: (+) enantiomer Compound 2
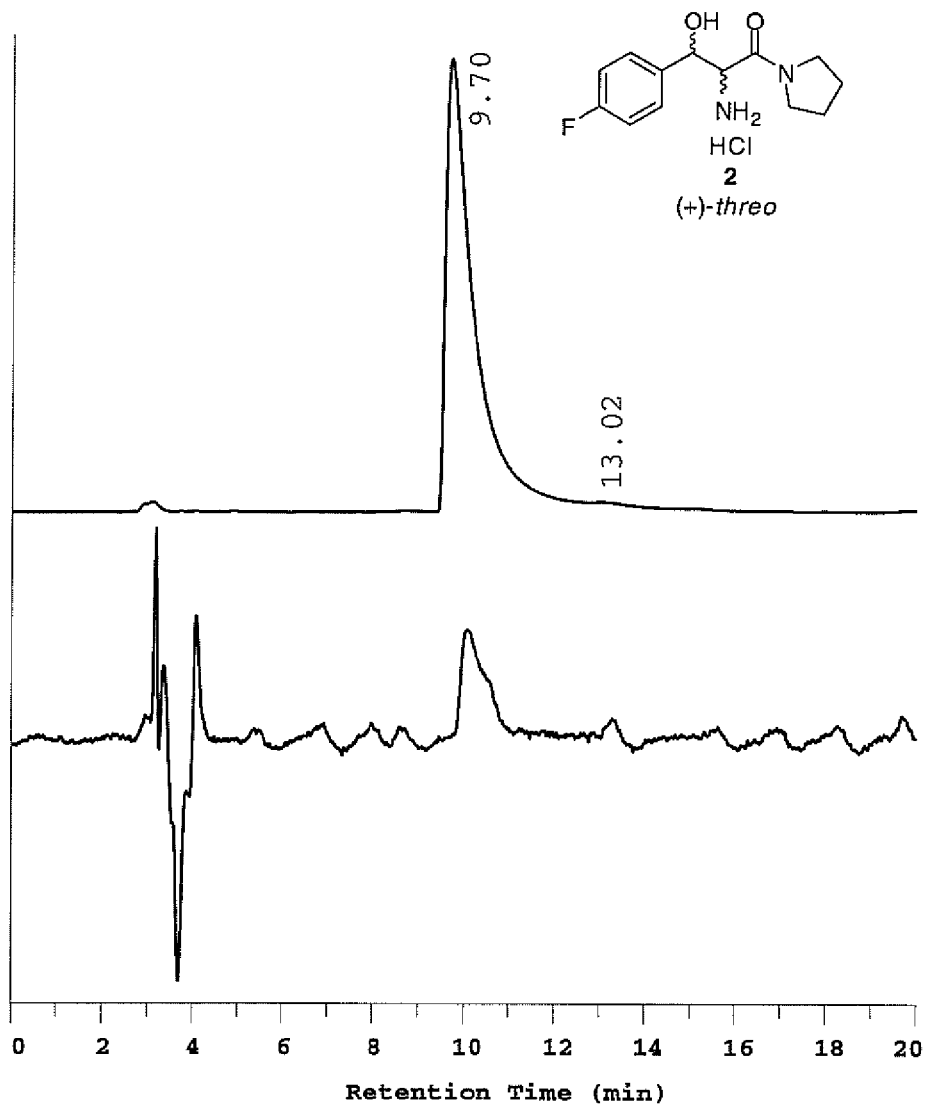
```
No.    RT     Area       Conc 1    BC
-------------------------------------------
1     9.70   21270577   99.693    BV
2    13.02      65459    0.307    TBB
-------------------------------------------
             21336036  100.000
```

Figure 3: Enantiomeric purity of the (-) enantiomer – Compound 3
Description:
Chiralpak IA®, hexane:ethanol = 80:20, 220 nm UV+ polarimetry, 1 mL/min
Sample Name: (-) enantiomer Compound 3
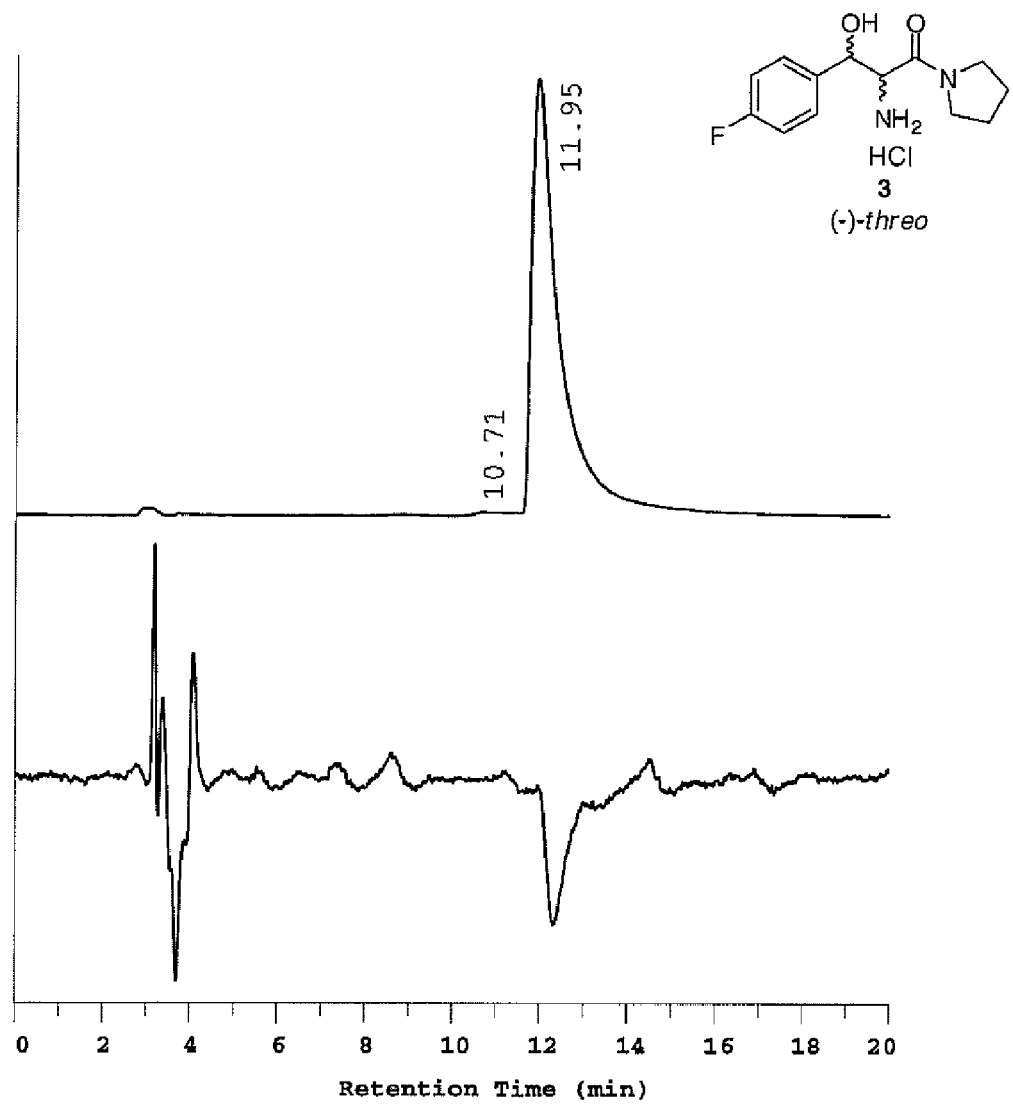
| No. | RT | Area | Conc 1 | BC |
|---|---|---|---|---|
| 1 | 10.71 | 80255 | 0.352 | MC |
| 2 | 11.95 | 22692739 | 99.648 | MC |
|  |  | 22772994 | 100.000 |  |

Figure 4: Separation of racemate Compound 4 on Sepapak®-2 HR
Description:
Sepapak®-2 HR, hexane:ethanol = 60:40, 220 nm UV+ polarimetry, 1 mL/min
Sample Name: racemate Compound 4
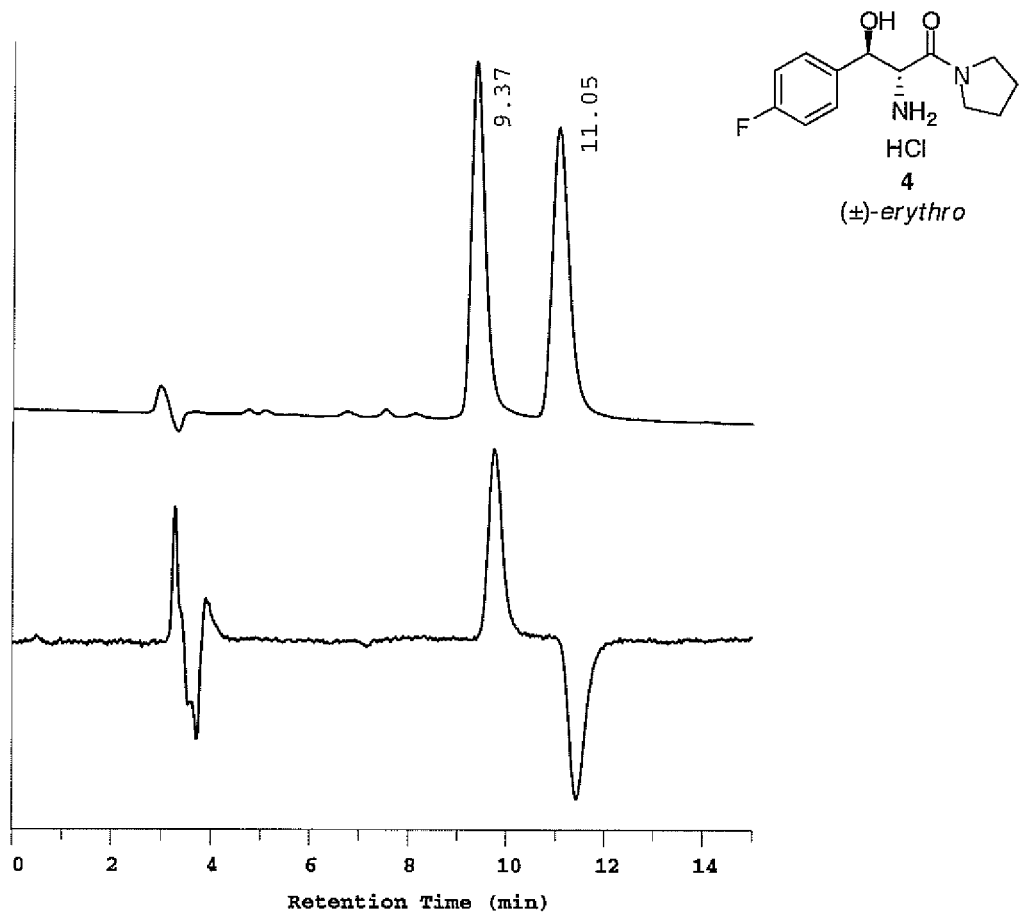
```
No.     RT      Area        Conc 1    BC
-------------------------------------------
  1    9.37    18678691     49.443    BV
  2   11.05    19099753     50.557    VB
-------------------------------------------
               37778444    100.000
RT          k'     Asym      N        Res     Alpha    S/N    Noise
(min)                      (USP)     (USP)                    (uV)
-------------------------------------------------------------------
 9.37       1.91   1.42*    5354      ---      ---     ---    ---
11.05       2.43   1.42*    4839*    2.92     1.27     ---    ---
```

Figure 5: Enantiomeric purity of the (+) enantiomer – Compound 5
Description:
Sepapak®-2 HR, hexane:ethanol = 60:40, 220 nm UV+ polarimetry, 1 mL/min
Sample Name: (+) enantiomer Compound 5
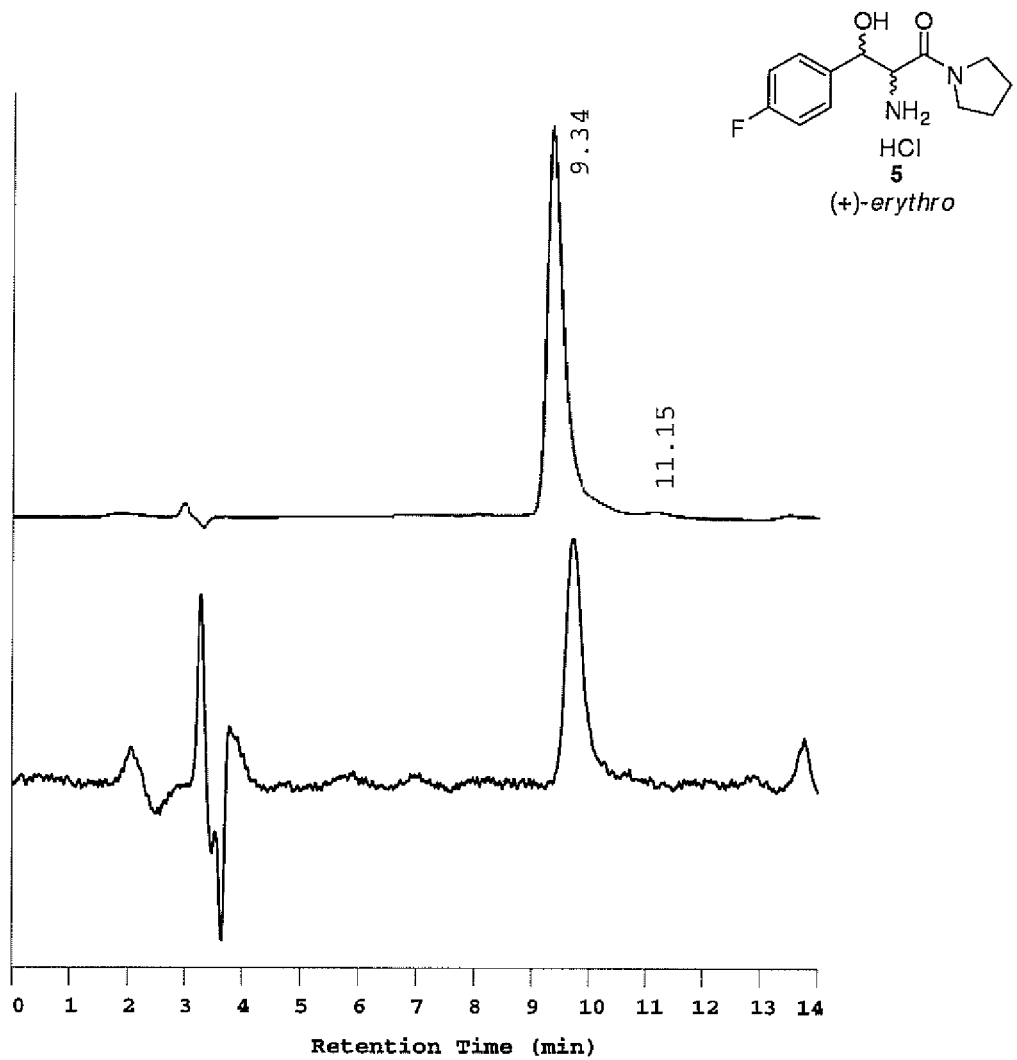
```
No.      RT        Area      Conc 1     BC
------------------------------------------------
  1     9.34    11209313     99.355     BV
  2    11.15       72769      0.645     TBB
------------------------------------------------
                11282082    100.000
```

Figure 6: Enantiomeric purity of the (-) enantiomer – Compound 6
Description:
Sepapak®-2 HR, Hexane:ethanol = 60:40, 220 nm UV+ polarimetry, 1 mL/min
Sample Name: (-) enantiomer Compound 6
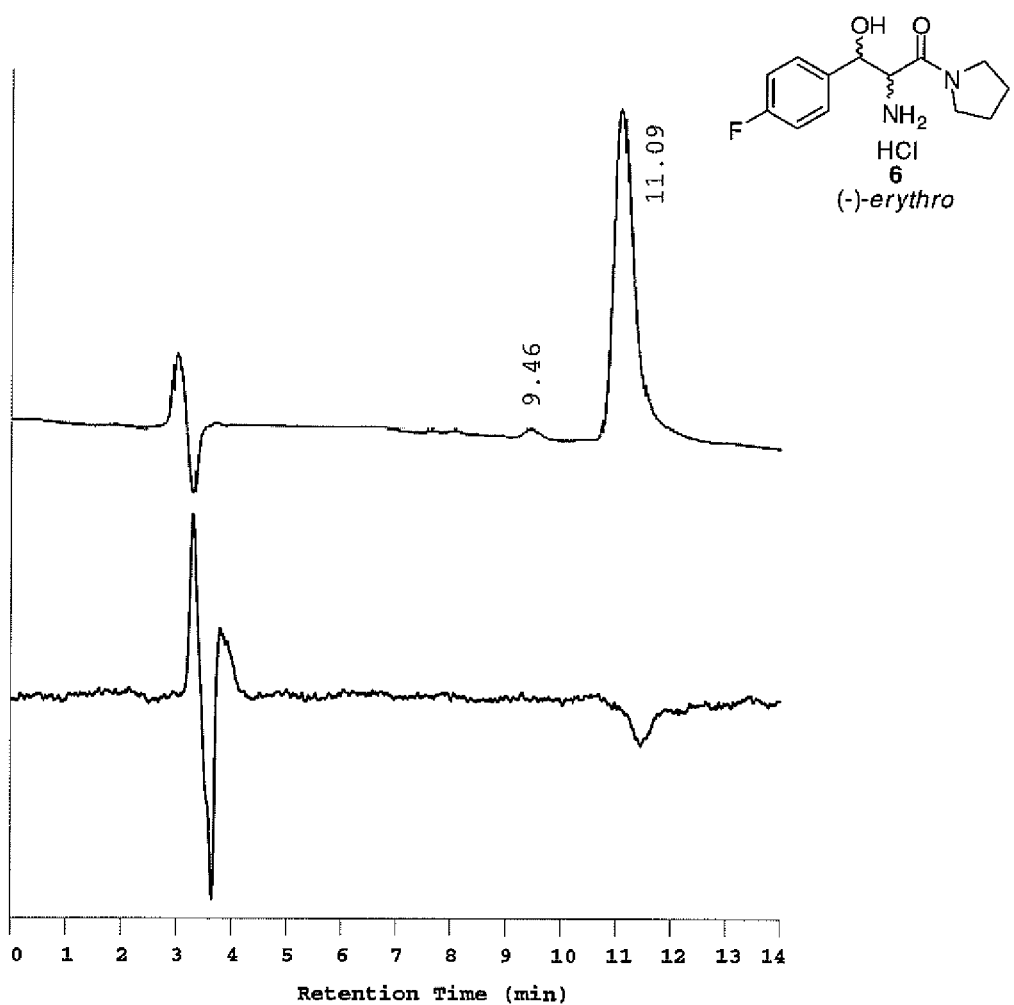
```
No.      RT       Area      Conc 1     BC
-----------------------------------------------
 1      9.46      26958      0.909     BB
 2     11.09    2938717     99.091     BB
-----------------------------------------------
                2965675    100.000
```

Figure 7: Absolute configuration determination of Compound 3 by single crystal X-ray diffraction:
(2*R*,3*S*)-2-Amino-3-(4-fluorophenyl)-3-hydroxy-1-(pyrrolidin-1-yl)propan-1-one hydrochloride sesquihydrate Compound 3.
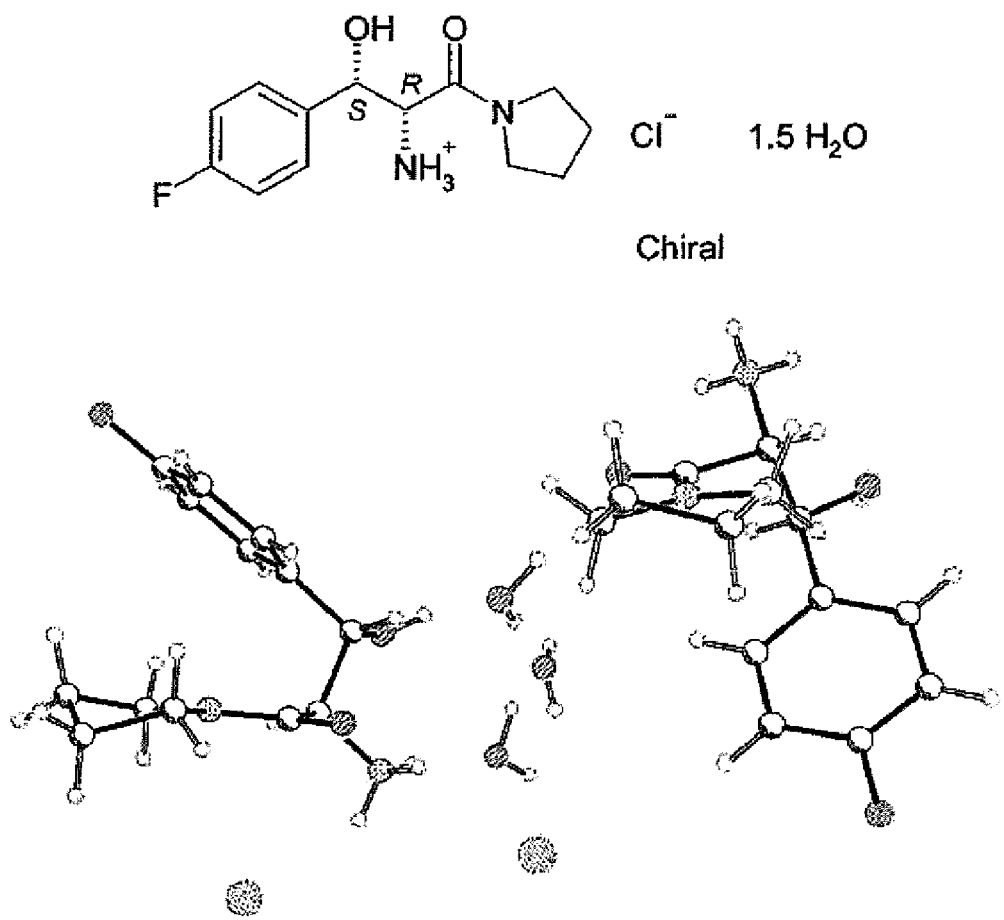
Chiral

US 8,168,631 B2

3-(4-FLUOROPHENYL)-3-HYDROXY-2-AMINO-PROPIONIC ACID AMIDES AND RELATED COMPOUNDS HAVING ANALGESIC ACTIVITY

RELATED APPLICATION DATA

This application claims the benefit of U.S. Provisional Application Ser. No. 61/026,178, filed Feb. 5, 2008 which is hereby incorporated by reference in its entirety.

FIELD OF THE INVENTION

The present invention relates to derivatives of 3-(4-fluorophenyl)-3-hydroxy-2-amino-propionic acid amides and related compounds having analgesic activity. The present invention also relates to pharmaceutical compositions containing these compounds as active ingredient for alleviating or eliminating pain in mammals and to methods of using said pharmaceutical compositions as analgesics.

BACKGROUND OF THE INVENTION

United States Patent Application Publications US 2003/0153768; US 2003/0050299 disclose compounds such as those shown below:

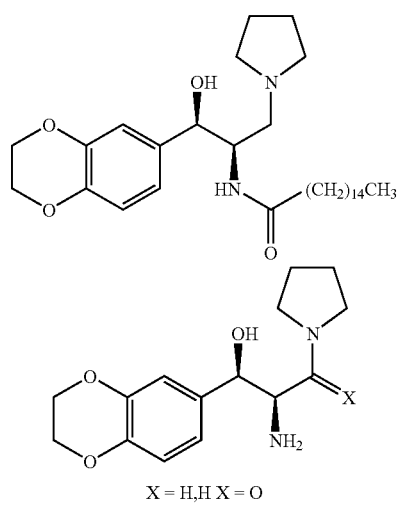

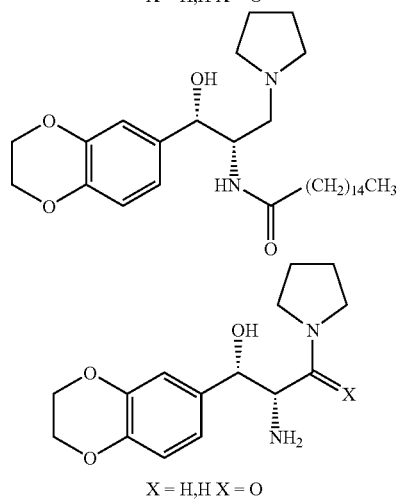

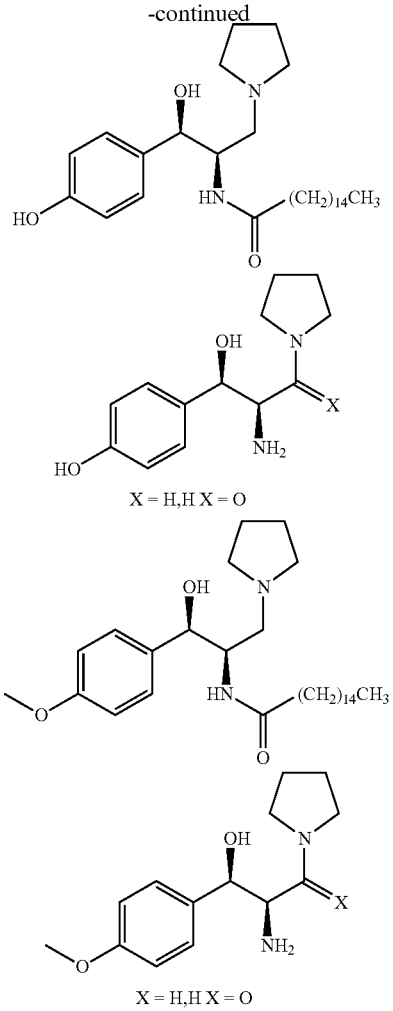

U.S. Pat. Nos. 5,945,442; 5,952,370; 6,030,995 and 6,051,598, which are all related to each other as being based on same or related disclosures, describe compounds which are structurally similar to the known compounds shown above.

A publication in Journal of Labelled Compounds & Radiopharmaceuticals (1996), 38 (3), 285-97 discloses the compound of the formula:

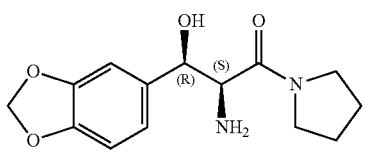

Patent application WO 081273 published on 3 Aug. 2006 also discloses compounds which are structurally related to the compounds shown above.

BRIEF DESCRIPTION OF THE DRAWINGS

FIG. 1 shows the separation of racemate Compound 1 on Chiralpak® IA.
FIG. 2 shows shows the enantiomeric purity of the (+) enantiomer of Compound 2.
FIG. 3 shows the enantiomeric purity of the (−) enantiomer of Compound 3.

FIG. 4 shows the separation of racemate Compound 4 on Sepapak®-2 HR.

FIG. 5 shows the enantiomeric purity of the (+) enantiomer of Compound 5.

FIG. 6 shows the enantiomeric purity of the (−) enantiomer of Compound 6.

FIG. 7 shows the absolute configuration determination of (2R,3S)-2-Amino-3-(4-fluorophenyl)-3-hydroxy-1-(pyrrolidin-1-yl)propan-1-one hydrochloride sesquihydrate by single crystal X-ray diffraction.

DETAILED DESCRIPTION OF THE INVENTION

Disclosed herein is a compound represented by the formula:

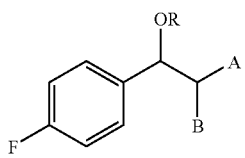

wherein A is an amide moiety having a formula $C_{1-7}O_{1-2}S_{0-1}N_{1-2}H_{2-16}F_{0-2}$;
B is an amine, an N-amide, or sulfonamide moiety having a formula $C_{1-12}H_{2-30}O_{1-4}S_{0-1}N_{1-3}F_{0-2}Cl_{0-2}Br_{0-2}I_{0-2}$; and
R is H, $C_{1-6}$ alkyl, or $C_{1-6}$ acyl.

These compounds are useful for treating pain.

Typically, a dosage form (such as pill, tablet, or capsule for oral administration, or a liquid for injection) is prepared containing the compound, and the dosage form is administered to a mammal needing the treatment. Preparation of suitable dosage forms is known in the art. For example, U.S. patent application Ser. No. 11/814,604, filed on Jul. 24, 2007, describes suitable methods.

The dose may vary depending upon the mammal being dosed and the particular condition being treated. A person of ordinary skill in the art can determine the dose appropriate for the situation. For example, for humans, a dose range of 0.5 mg to 1000 mg is contemplated.

For the purposes of this disclosure, "treat," "treating," or "treatment" refers to the diagnosis, cure, mitigation, treatment, or prevention of disease or other undesirable condition.

Unless otherwise indicated, reference to a compound should be construed broadly to include any compounds, pharmaceutically acceptable salts, prodrugs, tautomers, alternate solid forms, non-covalent complexes, and combinations thereof, of a chemical entity of a depicted structural formula or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

A, B, and R are standard moieties recognized as stable in the art. Unusual structures such as open shell atoms, overstrained rings, and hypervalent atoms are not contemplated. For example, all carbon atoms have 4 covalent bonds in any combination of single, double, or triple bonds, where a double bond counts as 2 covalent bonds, and a triple bond counts as 3 covalent bonds. All hydrogen and halogen atoms have a single covalent bond. All oxygen atoms have 2 covalent bonds. All nitrogen atoms have 3 covalent bonds. Finally, sulfur atoms usually have 2 covalent bonds, but may also form one of the following functional groups:

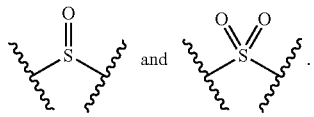

A is an amide moiety having a formula $C_{1-7}O_{1-2}S_{0-1}N_{1-2}H_{2-16}F_{0-2}$. The formula $C_{1-7}O_{1-2}S_{0-1}N_{1-2}H_{2-15}F_{0-2}$ means that A has from 1 to 7 carbon atoms, from 1 to 2 oxygen atoms, from 0 to 1 sulfur atoms, from 1 to 2 nitrogen atoms, from 2 to 16 hydrogen atoms, and from 0 to 2 fluorine atoms.

An amide moiety has the functional group:

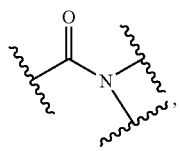

where the carbonyl carbon directly attaches to the remainder of the molecule and the 2 bonds from the N go to the remainder of the amide moiety (i.e. the remaining part of A).

For example, A could be an acyclic amide moiety such as:

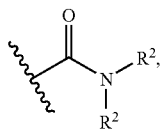

wherein each $R^2$ is independently hydrogen or linear alkyl, provided that the total number of carbon atoms in A is from 1 to 7. For example, on $R^2$ might be $C_{1-6}$ alkyl, and the other $R^2$ might be hydrogen. Alternatively, both $R^2$ could be hydrogen, or both $R^2$ could be alkyl.

$C_{1-6}$ alkyl is alkyl having from 1 to 6 carbon atoms, e.g. methyl, ethyl, propyl isomers, butyl isomers, pentyl isomers, hexyl isomers, cyclopropyl, cyclobutyl, cyclopenyl, cyclohexyl, etc.

Alkyl is a moiety containing only carbon and hydrogen that has only single covalent bonds, i.e. no double or triple bonds are present.

For example, A could be one of the moieties depicted below.

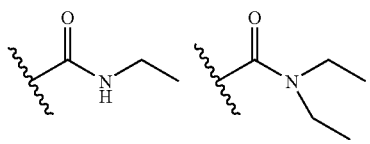

A could also be a cyclic amide, meaning that A has a ring as part of the structure. For example, the nitrogen attached to the carbonyl of the amide could be part of a cycle. For the purposes of this disclosure, this type of amide is referred to as an "N-cyclic amide." Examples of N-cyclic amides include the structures below.

The structures depicted above might also be varied by increasing or decreasing the ring size, or by moving a heteroatom, double bond, or substituent to form other N-cyclic amides.

Other moieties for A that are not depicted here are also possible, provided that they conform to the constraints defined herein.

B is an amine or an N-amide moiety having a formula $C_{1-12}H_{2-30}O_{1-4}S_{0-1}N_{1-3}F_{0-2}Cl_{0-2}Br_{0-2}I_{0-2}$. The formula $C_{1-12}H_{2-30}O_{1-4}S_{0-1}N_{1-3}F_{0-2}Cl_{0-2}Br_{0-2}I_{0-2}$ means that B has from 1 to 12 carbon atoms, from 2 to 30 hydrogen atoms, from 1 to 4 oxygen atoms, from 0 to 1 sulfur atoms, from 1 to 3 nitrogen atoms, from 0 to 2 fluorine atoms, from 0 to 2 chlorine atoms, from 0 to 2 bromine atoms, and from 0 to 2 iodine atoms.

An amine moiety has the functional group:

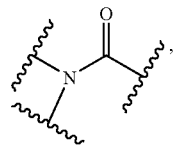

where 1 bond from the nitrogen attaches to the remainder of the molecule and the other 2 bonds from the nitrogen attach to the remainder of the amine moiety (i.e. the remaining part of B).

For example, B might be a linear alkyl amine, meaning a moiety having the formula —NH—$C_{1-6}$alkyl, wherein the alkyl is linear.

B might also be a benzylic amine, meaning a moiety having the formula —NH—$CH_2$-Ph, wherein Ph is substituted or unsubstituted phenyl. Any substituent may be present on phenyl, provided that it conforms to the constrains for B defined herein. Examples of useful substituents include F, Cl, Br, I, OH, $NH_2$, $C_{1-6}$ alkyl, O—($C_{1-6}$ alkyl), S—($C_{1-6}$ alkyl), $CO_2H$, and CN.

B might also be an N-amide. An N-amide moiety has the functional group:

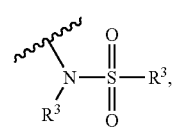

where one of the 2 bonds from the N attaches to the remainder of the molecule, and 1 of the bonds from the N and the bond from the carbonyl carbon to the remainder of the N-amide moiety (i.e. the remaining part of B).

Examples include those shown below:

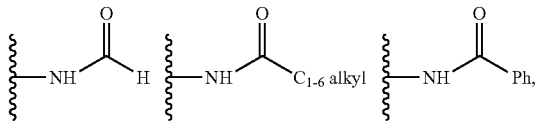

where Ph is substituted or unsubstituted phenyl. Any substituent may be present on phenyl, provided that it conforms to the constrains for B defined herein. Examples of useful substituents include F, Cl, Br, I, OH, $NH_2$, $C_{1-6}$ alkyl, O—($C_{1-6}$ alkyl), S—($C_{1-6}$ alkyl), $CO_2H$, and CN.

In one embodiment, the $C_{1-6}$ alkyl depicted above is linear.

A sulfonamide moiety has a formula:

wherein each $R^3$ are independently any moiety that conforms to the constraints for B defined herein.

For example, H and $C_{1-6}$ alkyl are particularly contemplated for $R^3$. Examples include:

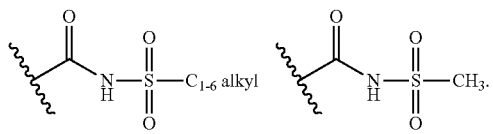

Other moieties for B are also possible that are not depicted here, provided that they conform to the constraints defined herein.

For both A and B, there is no direct bonding between heteroatoms, meaning that there are no direct bonds between any combination of O, N, and S (e.g. —O—O—, —S—S—, —O—S—, —O—N—, etc.), except in the case of a sulfonamide.

R is H, $C_{1-6}$ alkyl or $C_{1-6}$ acyl. Acyl is

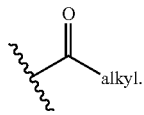

For example, H, —COCH$_3$ and methyl are examples of useful moieties for R.

In one embodiment, R is H.
In another embodiment, A is:

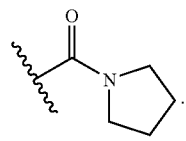

In another embodiment, B is NH$_2$.

Another embodiment is a compound represented by the formula:

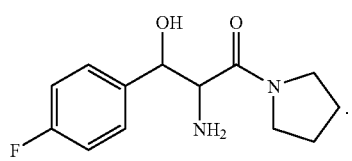

In another embodiment, the compound above is the erythro form.
In another embodiment, the compound above is the (+)-enantiomer of the erythro form.
In another embodiment, the compound above is the (−)-enantiomer of the erythro form.
In another embodiment, the compound above is the threo form.
In another embodiment, the compound above is the (+)-enantiomer of the threo form.
In another embodiment, the compound above is the (−)-enantiomer of the threo form.

Another embodiment is a method of treating pain comprising administering a compound according to the invention to a mammal in need thereof.

Another embodiment is use of a compound according to the invention in the manufacture of a medicament for the treatment of pain in a mammal.

Another embodiment is a dosage form comprising a compound according to the invention and a pharmaceutically acceptable excipient.

Exemplary compounds contemplated for use in the practice of the invention are depicted below:

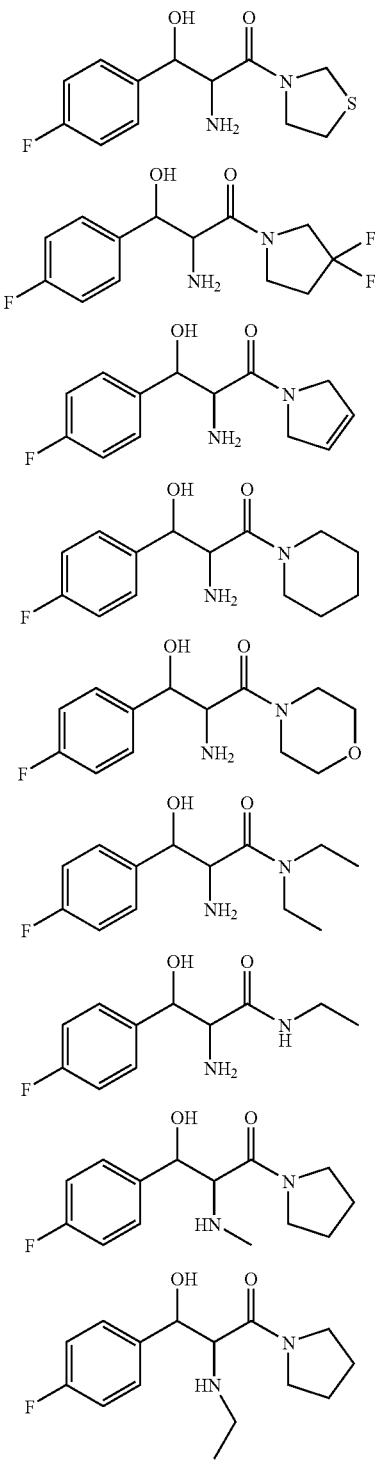

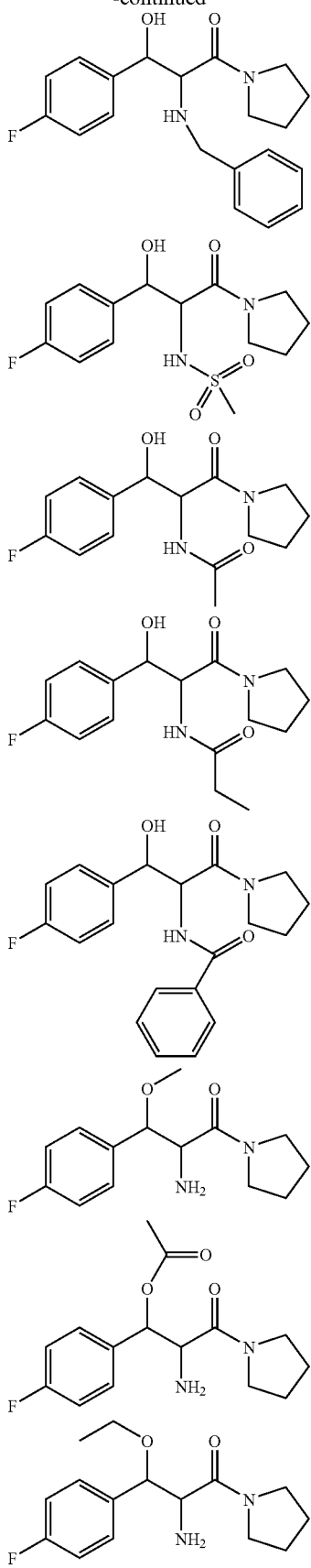

Most compounds disclosed herein have two asymmetric carbons adjacent to one another, and therefore can exist in erythro or threo form, with each of these two forms having dextrorotatory D- or (+)- or levorotary L- or (−)-enantiomers. The designation "(±)" in this application includes the pure dextrorotatory enantiomer, the pure levorotatory enantiomer and any mixture of the two enantiomers in equal or in unequal proportions.

For simplicity sake in many of the structural formulas, such as in the example below, only one of the enantiomers is actually shown but when the designation "(±)" appears it also includes the enantiomeric form (mirror image) of the structure actually shown in the formula.

For example:

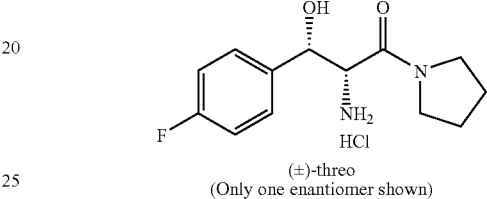

(±)-threo
(Only one enantiomer shown)

Thus, in the example above, only one enantiomer is shown, but because the designation "(±)" appears below the formula, its optical isomer:

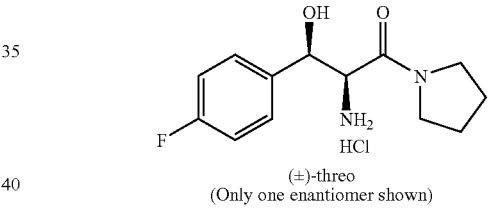

(±)-threo
(Only one enantiomer shown)

and all racemic mixtures of the two optical isomers are also included.

Analgesic Activity in the Neuropathic Pain Model (the Chung Model)

Several of the compounds disclosed herein were tested in the rat model of spinal nerve ligation (SNL) which involves a traumatic partial nerve injury, involving tight ligation of the L5 and L6 spinal nerves (Kim and Chung, 1992). Pain, including mechanical allodynia and thermal hyperalgesia, persists in the absence of ongoing tissue injury for more than 2 months following the surgery. The ability of the drug to alleviate the mechanical allodynia was assessed using a series of Von Frey hairs applied to the mid-plantar area of the ipsilateral hind paw before and after drug administration. The paw withdrawal threshold was determined using a standard up-down testing method (Dixon, 1980) and expressed relative to the paw withdrawal threshold in uninjured rats. As shown in Table 1, Compound 1 and Compound 3 at 1 mg/kg reversed pain by 64% and 86%, respectively in the Chung model. Interestingly, substitution at position 4 with either chlorine or iodine abolished this analgesic activity. These results indicates that there is a size limitation on the position 4 substitution.

TABLE 1

| | | | Percent pain reversal at time in min | | |
|---|---|---|---|---|---|
| CODE | FORMULA | Dose mg/kg | 15 | 30 | 60 |
| Compound 1 | 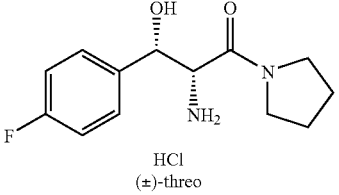<br>HCl<br>(±)-threo | 1 | 28 | 52 | 64 |
| | | 0.3 | 17 | 29 | 52 |
| Compound 3 | 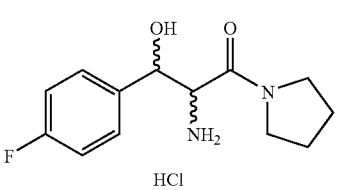<br>HCl<br>(−)-threo | 1 | 57.2 | 73.5 | 86.2 |
| | | 0.3 | 26.7 | 53.6 | 75.5 |
| | | 0.1 | 1.2 | 20.2 | 43.2 |
| | 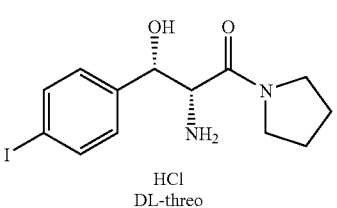<br>HCl<br>DL-threo | 0.3 | 4.3 | 5.8 | 7.3 |
| | 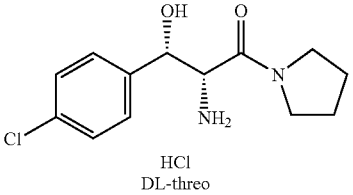<br>HCl<br>DL-threo | 0.3 | 4.8 | 7.5 | 8.6 |

REFERENCES FOR THE PAIN MODEL

Kim S H, Chung J M. An experimental model for peripheral neuropathy produced by segmental spinal nerve ligation in the rat, Pain 1992; 50 (3): 355-63.

Dixon W J. Efficient analysis of experimental observations. Annu Rev Pharmacol Toxicol 1980; 20: 441-62.

The compounds disclosed herein can be synthesized by utilizing the synthetic methods described in a general sense immediately below and in more detail in the experimental section of the present application, or by such modifications of the below described experimental methods which will become readily apparent to those skilled in the art in light of the present disclosure.

Reaction Scheme 1

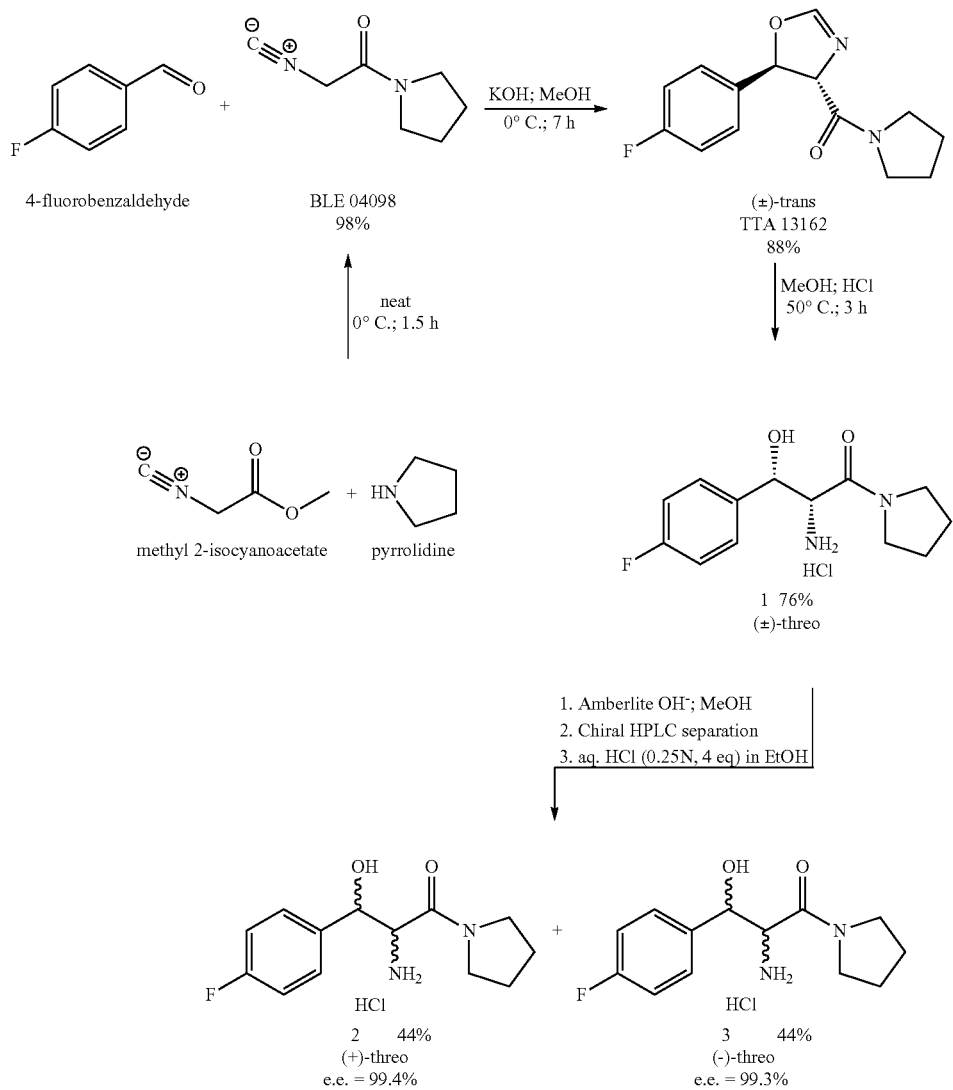

Compound 1 (Reaction Scheme 1) was obtained in three synthetic steps. Methyl 2-isocyanoacetate reacted neat at 0° C. for 1.5 hour with pyrrolidine to give 2-isocyano-1-(pyrrolidin-1-yl)ethanone BLE 04098 in 98% yield. Amide BLE 04098 was treated with 4-fluorobenzaldehyde in presence of KOH in MeOH at 0° C. for 7 hours to led diastereoselectively (diastereoisomeric excess d.e.>96%) to the (±)-trans oxazoline TTA 13162 in 88% yield. Final hydrolysis of the oxazoline TTA 13162 by an aqueous HCl solution in MeOH at 50° C. afforded to (±)-threo-2-amino-3-(4-fluorophenyl)-3-hydroxy-1-(pyrrolidin-1-yl)propan-1-one hydrochloride, Compound 1, in 76% yield (65.5% total yield).

Enantiomers (+)-threo Compound 2 and (−)-threo Compound 3 (Reaction Scheme 1) were obtained in 44% yield each from the free base of racemate Compound 1 (prepared from Compound 1HCl salt using Amberlite OH⁻ resin in MeOH) by chiral HPLC separation using a semi-preparative Chiralpak® IA column followed by a 0.25 N aqueous HCl treatment in ethanol. Their enantiomeric excess (e.e.), 99.4 (Compound 2) and 99.3% (Compound 3), was measured by analytical chiral HPLC using an analytical Chiralpak® IA column.

(±)-erythro-2-Amino-3-(4-fluorophenyl)-3-hydroxy-1-(pyrrolidin-1-yl)propan-1-one hydrochloride, Compound 4 (Reaction Scheme 2), was obtained in three synthetic steps from its (±)-threo diastereoisomer, Compound 1. Compound 1 was reacted with Boc anhydride, in presence of triethylamine and dichloromethane as solvent, to give the N-Boc protected derivative SLA 19084 in 78% yield. The secondary alcohol function of SLA 19084 was oxidized at room temperature using the Dess-Martin periodinane in dichloromethane to afford to the dioxo derivative, SLA 19086, in 76% yield. SLA 19086 was reduced diastereoselectively (diastereoisomeric excess d.e.=60%) by sodium borohydride in methanol at 0° C. to produce in 70% yield a mixture (SLA 19088) of (±)-erythro and (±)-threo isomers in a ratio of 80:20, respectively (as measured by ¹H NMR). Treatment of the mixture SLA 19088 by a solution of trifluoroacetic acid (TFA) in dichloromethane followed by purification by reverse phase preparative HPLC(C18) and HCl treatment in methanol led to (±)-erythro-2-amino-3-(4-fluorophenyl)-3-hydroxy-1-(pyrrolidin-1-yl)propan-1-one hydrochloride, Compound 4 (d.e.>98%), in 38% yield.

Reaction Scheme 2

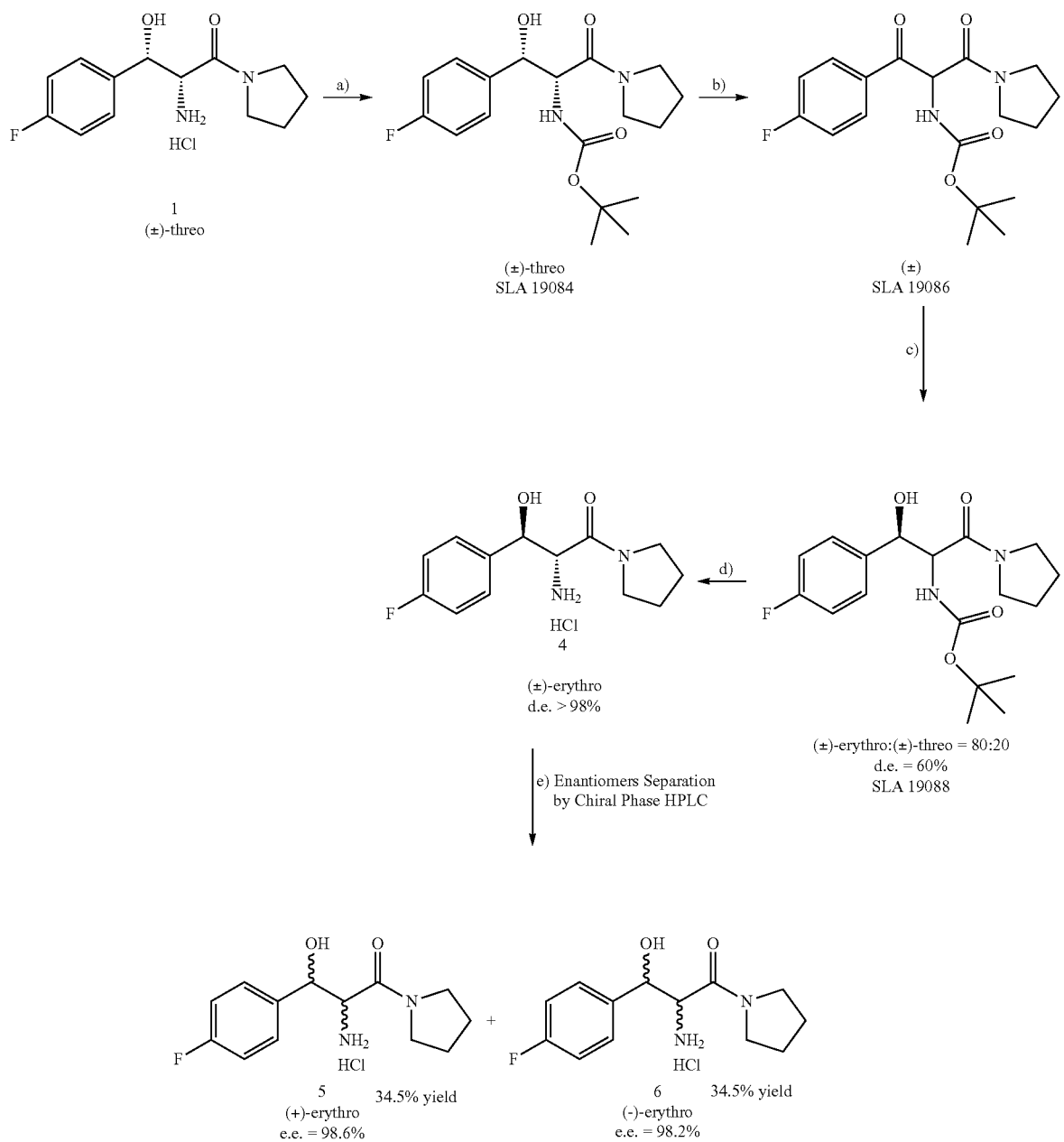

a) i. Boc₂O, TEA, CH₂Cl₂, 78% yield b) i. Dess Martin Periodinane, CH₂Cl₂, 76% yield. c) i. NaBH₄, MeOH, 0° C. to RT, 3 h, 70% yield
d) i. TFA (20 eq.), CH₂Cl₂, 0° C. to RT, 2 h, ii. Reverse Phase HPLC C18 iii. HCl, MeOH. 38% yield e) i. Amberlite ⁻OH form, MeOH ii. Chiral Phase HPLC iii. 0.25N aqueous HCl, EtOH.

Enantiomers (+)-erythro Compound 5 and (−)-erythro Compound 6 (Reaction Scheme 2) were obtained in 34.5% yield each from the free base of racemic Compound 4 (prepared from Compound 4 HCl salt using Amberlite OH⁻ resin in MeOH) by a semi-preparative chiral HPLC separation using a Sepapak®-2 HR column (250×4.6 mm, 3 μm) followed by a 0.25 N aqueous HCl treatment in EtOH. Enantiomeric excesses (e.e.) of 98.6% for Compound 5 and 98.2% for Compound 6, were measured by analytical chiral HPLC using a Sepapak®-2 HR column.

Reaction Scheme 3

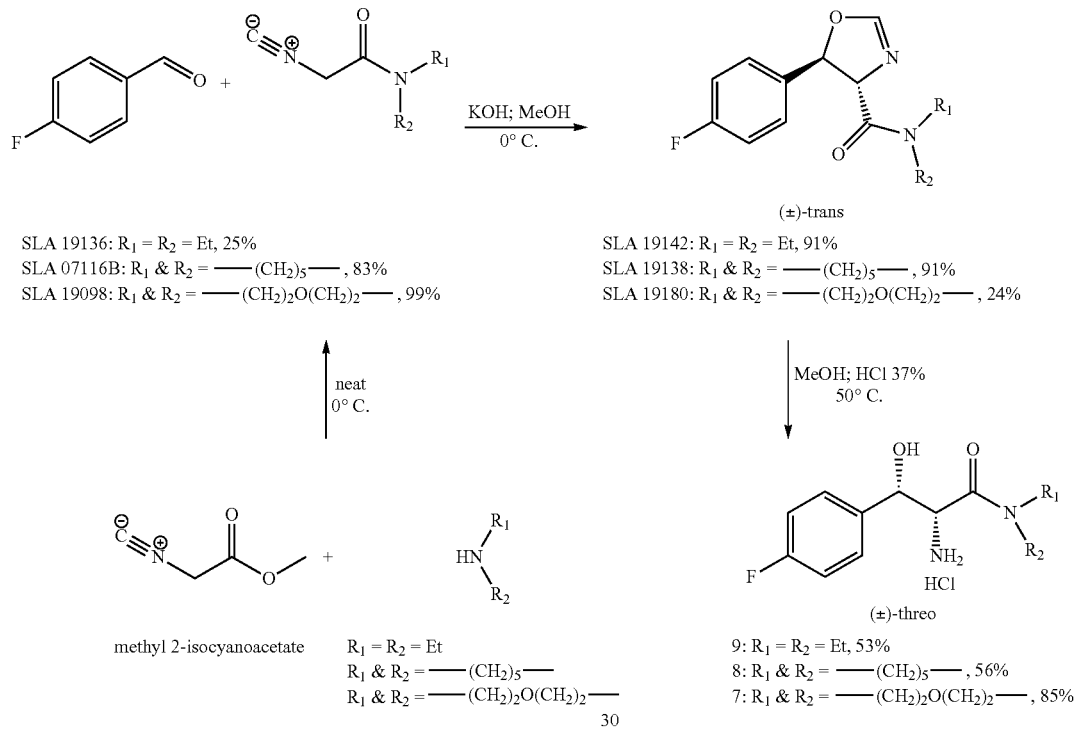

Compounds 7-9 (Reaction Scheme 3) were obtained in three synthetic steps. Methyl 2-isocyanoacetate reacted neat at 0° C. with ethylamine, piperidine or morpholine led respectively to the corresponding isocyanoamides SLA 19136, SLA 07116B or SLA 19098 in 25%-99% yields. Amides SLA 19136, SLA 07116B or SLA 19098 were separately reacted with 4-fluorobenzaldehyde in presence of KOH in MeOH at 0° C. to produce diastereoselectively (diastereoisomeric excess d.e.>96%) the (±)-trans oxazolines, SLA 19142, SLA 19138 or SLA 19180, respectively, in 24-91% yields. Final ring opening of the oxazolines SLA 19142, SLA 19138 or SLA 19180 by an aqueous HCl solution in MeOH at 50° C. afforded Compounds 7, 8, and 9, respectively, in 53-85% yield.

Reaction Scheme 4

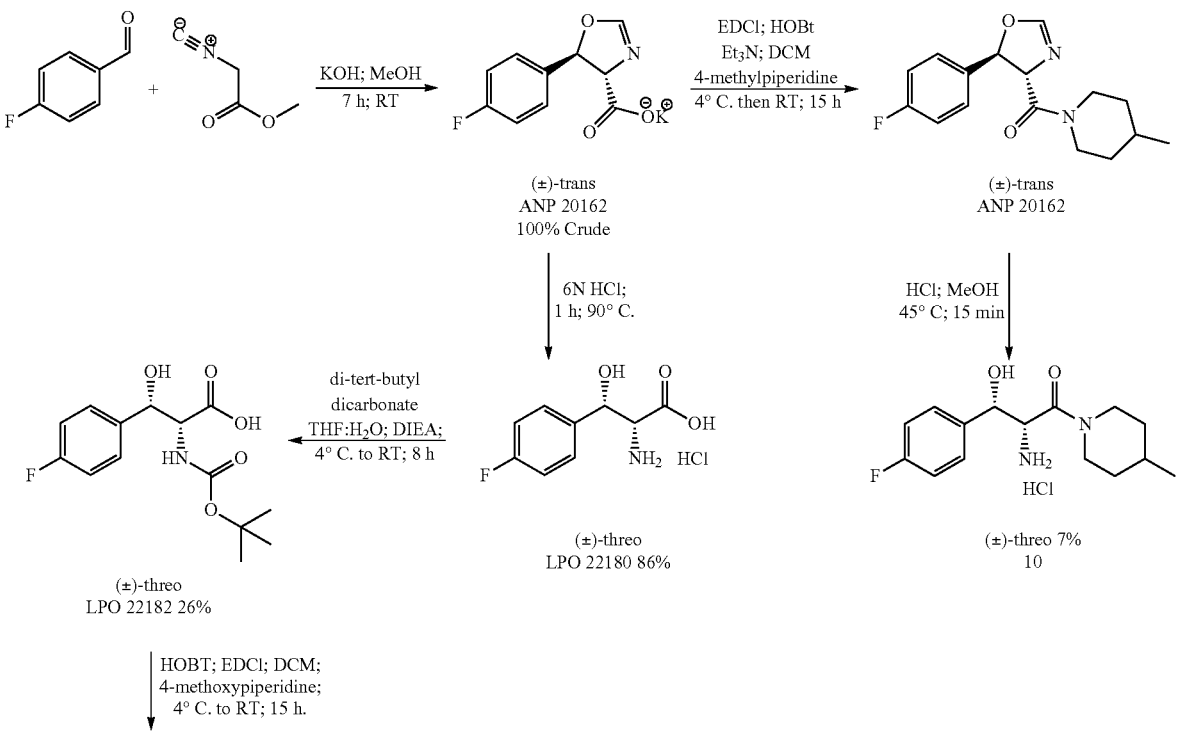

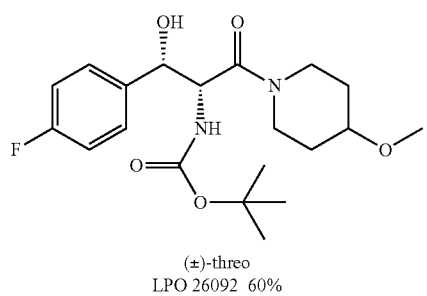

(±)-threo
LPO 26092 60% i) DCM; TFA
15 min; RT
ii) 1.56N HCl in
MeOH; 4° C.;
15 min.

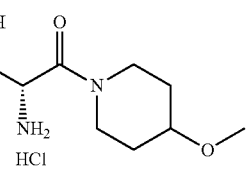

(±)-threo
11
52%

Compound 10 (Reaction Scheme 4) was obtained in three synthetic steps. Methyl 2-isocyanoacetate reacted with 4-fluorobenzaldehyde and KOH in MeOH for 7 h at room temperature to afford diastereoselectivity and quantitatively the crude potassium salt trans-ANP 20162. Potassium salt ANP 20162 was coupled with 4-methylpiperidine using the EDCI-HOBT method in dichloromethane to produce the oxazoline amide, LPO 26074 Oxazoline LPO 26074 then underwent ring opening using a HCl 37% solution in MeOH at 45° C. for 15 min to give Compound 10 in 7% yield after purification.

Compound 11 (Reaction Scheme 4) was obtained from the crude potassium salt trans-ANP 20162 in four synthetic steps. Potassium salt ANP 20162 was hydrolyzed by a solution of 6 N HCl for 1 h at 90° C. to afford to the carboxylic acid, LPO 22180, in 86% yield. The carboxylic acid, LPO 22180, was reacted with di-tert-butyl dicarbonate in a 1:1 mixture of THF and $H_2O$ in presence of diethylamine at 4° C. to RT for 8 h to give the t-Boc protected carboxylic acid, LPO 22182, in 26% yield. LPO 22182 was coupled with 4-methoxypiperidine using the EDCI-HOBT method in dichloromethane at 4° C. to RT for 15 h to give the t-Boc protected amide, LPO 26092, in 60% yield. Amide LPO 26092 was deprotected by treatment with trifluoroacetic acid in dichloromethane for 15 min at RT to afford Compound 11, which was subsequently treated for 15 min at 4° C. with a 1.56 N HCl solution in MeOH to obtain Compound 11 in 52% yield.

Reaction Scheme 5

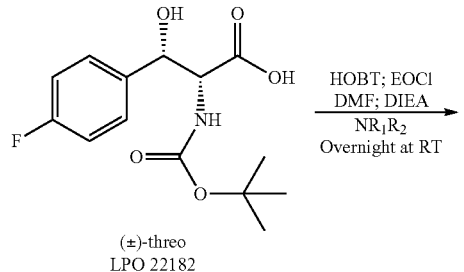

(±)-threo
LPO 22182

HOBT; EOCl
DMF; DIEA
$NR_1R_2$
Overnight at RT

Reaction Scheme 5 -continued

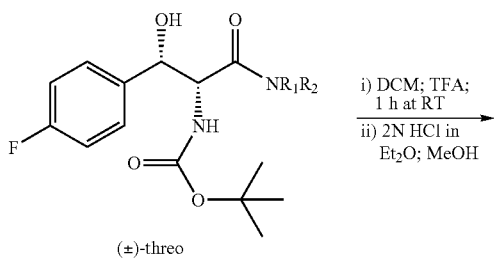

(±)-threo i) DCM; TFA;
1 h at RT
ii) 2N HCl in
$Et_2O$; MeOH

| Cpd | $NR_1R_2$ | % Yield |
|---|---|---|
| A | azepane | 94 |
| A | 3,3-difluoropyrrolidine | 89 |
| TTA 24064 | N-methyl-N-methoxy | 99 |

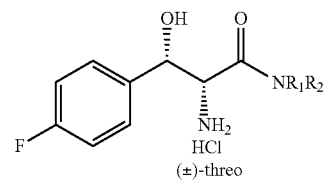

(±)-threo

| Cpd | $NR_1R_2$ | % Yield |
|---|---|---|
| 12 | azepane | 33 |
| 13 | 3,3-difluoropyrrolidine | 66 |
| 18 | N-methyl-N-methoxy | 47 |

Reaction Scheme 5

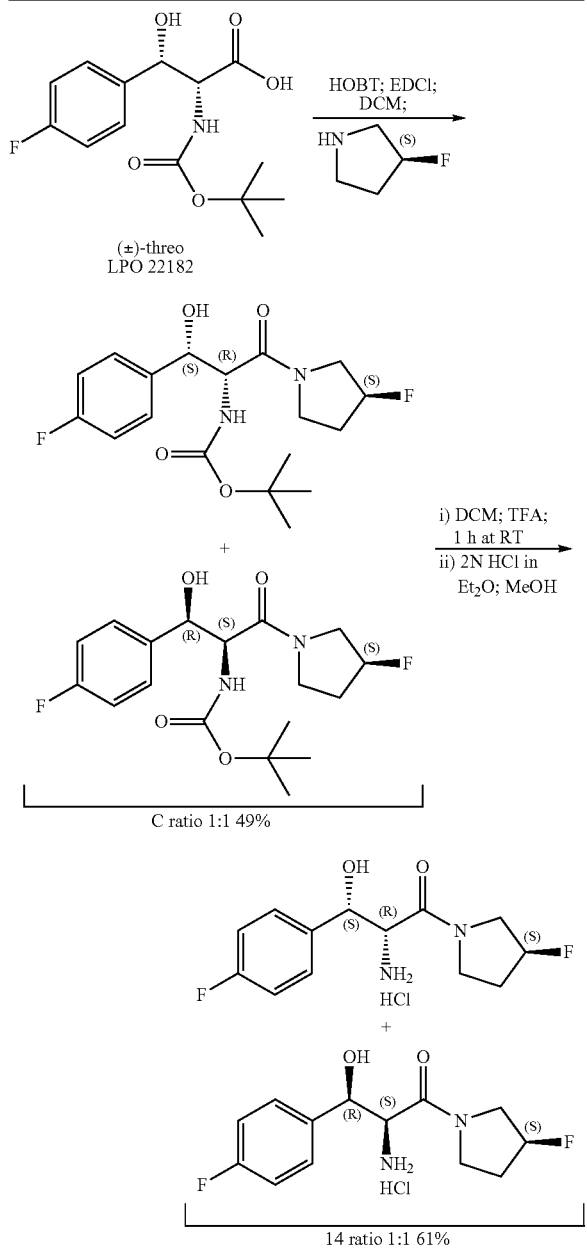

Compounds 12, 13 and 18 (Reaction Scheme 5) were obtained in two synthetic steps from carboxylic acid, LPO 22182. LPO 22182 was coupled separately with hexamethyleneimine, 3,3-difluoropyrrolidine hydrochloride and N,O-dimethylhydroxylamine hydrochloride using the EDCI-HOBT-DIEA method in dimethylformamide overnight at RT to produce the t-Boc protected amides A, B, and TTA 24064, respectively, in 89% to 99% yields. Finally, amides A, B and TTA 24064 were deprotected by treatment by trifluoroacetic acid in dichloromethane for one hour (15 h for TTA 24064) at RT to afford to Compounds 12, 13 and 18, respectively, as the free bases. Separate methanolic solutions of Compound 12 and 13 were treated for 10 min at RT with 2N HCl solutions in diethyl ether (a 0.2N HCl solution in MeOH was used for Compound 18 free base) to obtain Compounds 12, 13 and 18, respectively, in 33% to 66% yields.

Compound 14 (Reaction Scheme 3) was similarly obtained from carboxylic acid LPO 22182. LPO 22182 was coupled overnight at RT with (S)-3-fluoropyrrolidine hydrochloride using the EDCI-HOBT-DIEA method in dimethylformamide to produce the t-Boc protected amide, C (as a 1:1 mixture of two diastereoisomers) in 49% yield. A methanolic solution of amide C was treated with trifluoroacetic acid in dichloromethane for 1 h to afford to Compound 14 as a free base, which was subsequently treated for 10 min at RT with a 2N HCl solution in diethyl ether to obtain Compound 14 (as a 1:1 mixture of two diastereoisomers) in 61% yield.

Reaction Scheme 5

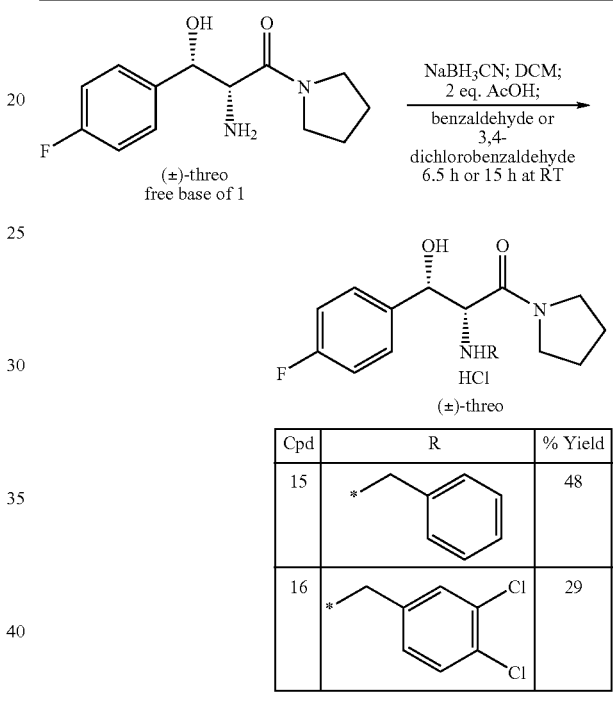

| Cpd | R | % Yield |
|---|---|---|
| 15 | *–CH₂–phenyl | 48 |
| 16 | *–CH₂–(3,4-dichlorophenyl) | 29 |

Compounds 15 and 16 (Reaction Scheme 5) were obtained from the free base of Compound 1 by reductive amination. The free base of Compound 1 in acetic acid was reacted separately with sodium cyanoborohydride and benzaldehyde (6.5 h at RT) or with dichlorobenzaldehyde (15 h at RT) to obtain respectively Compounds 15 and 16 as the free bases. Finally, separate methanolic solutions of the free bases of Compounds 15 and 16 (29% yield) were treated at 4° C. for 10 min with a 0.65 N HCl solution in MeOH to obtain the HCl salts of Compound 15 in 48% yield or of Compound 16 in 29% yield, respectively.

Reaction Scheme 6

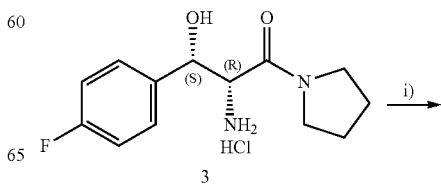

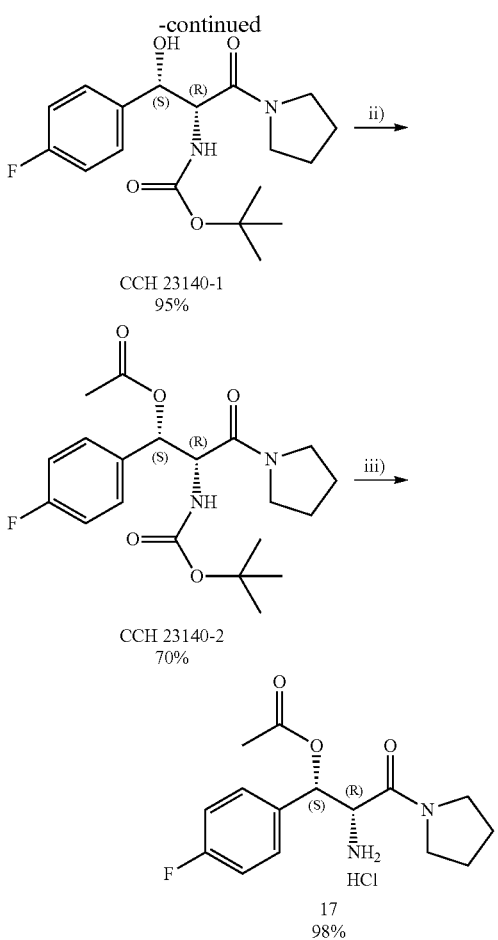

i) Et$_3$N; DMAP cat; DCM; di-tert-butyl dicarbonate; overnight at RT.
ii) diisopropylaminomethyl-polystyrene resin; DMAP cat.; DCM; AcOH; overnight at RT.
iii) HCl in Et$_2$O; 1 h at RT.

Compound 17 was obtained in three synthetic steps from Compound 3. Compound 3 in dichloromethane was treated overnight at RT with di-tert-butyl dicarbonate in the presence of triethylamine and a catalytic quantity of DMAP to afford the t-Boc protected derivative CCH 23140-1 in 95% yield. CCH 23140-1 was reacted overnight at RT with acetic acid in the presence of diisopropylaminomethyl resin and a catalytic quantity of DMAP to give the t-Boc protected acetate, CCH 23140-2, in 70% yield. Finally, CCH 23140-2 was treated for 1 h at RT with a solution of HCl in diethyl ether to obtain Compound 17 in 98% yield.

Examples of useful compounds include:

(±)-threo-2-Amino-3-(4-fluorophenyl)-3-hydroxy-1-(pyrrolidin-1-yl)propan-1-one hydrochloride, Compound 1,
(+)-threo-2-Amino-3-(4-fluorophenyl)-3-hydroxy-1-(pyrrolidin-1-yl)propan-1-one hydrochloride, Compound 2,
(−)-threo-2-Amino-3-(4-fluorophenyl)-3-hydroxy-1-(pyrrolidin-1-yl)propan-1-one hydrochloride, Compound 3,
(±)-erythro-2-Amino-3-(4-fluorophenyl)-3-hydroxy-1-(pyrrolidin-1-yl)propan-1-one hydrochloride, Compound 4,
(+)-erythro-2-Amino-3-(4-fluorophenyl)-3-hydroxy-1-(pyrrolidin-1-yl)propan-1-one hydrochloride Compound 5,
(−)-erythro-2-Amino-3-(4-fluorophenyl)-3-hydroxy-1-(pyrrolidin-1-yl)propan-1-one hydrochloride, Compound 6,
(±)-threo-2-Amino-3-(4-fluorophenyl)-3-hydroxy-1-(morpholin-4-yl)-propan-1-one hydrochloride, Compound 7,
(±)-threo-2-Amino-3-(4-fluorophenyl)-3-hydroxy-1-(piperidin-1-yl)propan-1-one hydrochloride, Compound 8,
(±)-threo-2-Amino-N,N-diethyl-3-(4-fluorophenyl)-3-hydroxypropanamide hydrochloride, Compound 9,
(±)-threo-2-Amino-3-(4-fluorophenyl)-3-hydroxy-1-(4-methylpiperidin-1-yl)propan-1-one hydrochloride, Compound 10,
(±)-threo-2-Amino-3-(4-fluorophenyl)-3-hydroxy-1-(4-methoxypiperidin-1-yl)propan-1-one hydrochloride, Compound 11,
(±)-threo-2-Amino-1-(azepan-1-yl)-3-(4-fluorophenyl)-3-hydroxypropan-1-one hydrochloride, Compound 12,
(±)-threo-2-Amino-1-(3,3-difluoropyrrolidin-1-yl)-3-(4-fluorophenyl)-3-hydroxypropan-1-one hydrochloride, Compound 13,
(2R,3S)-2-Amino-3-(4-fluorophenyl)-1-((S)-3-fluoropyrrolidin-1-yl)-3-hydroxypropan-1-one hydrochloride and (2S,3R)-2-amino-3-(4-fluorophenyl)-1-((S)-3-fluoropyrrolidin-1-yl)-3-hydroxypropan-1-one hydrochloride in ratio (1:1), Compound 14,
(±)-threo-2-(Benzylamino)-3-(4-fluorophenyl)-3-hydroxy-1-(pyrrolidin-1-yl)propan-1-one hydrochloride, Compound 15,
(±)-threo-2-(3,4-Dichlorobenzylamino)-3-(4-fluorophenyl)-3-hydroxy-1-(pyrrolidin-1-yl)propan-1-one hydrochloride, Compound 16,
(1S,2R)-2-Amino-1-(4-fluorophenyl)-3-oxo-3-(pyrrolidin-1-yl)propyl acetate hydrochloride, Compound 17,
(±)-threo-2-Amino-3-(4-fluorophenyl)-3-hydroxy-N-methoxy-N-methylpropanamide hydrochloride, Compound 18.

The following examples are intended only to illustrate the invention and should in no way be construed as limiting the invention.

EXAMPLES

General $^1$H NMR spectra were recorded at ambient temperature with an Avance 300 (Bruker) spectrometer.

Melting points were measured with a Büchi B-545 melting point apparatus and are uncorrected. To isolate reaction products the solvents were removed by evaporation using a vacuum rotatory evaporator with a water bath temperature not exceeding 40° C.

HPLC Method A: Compounds were analyzed by reverse phase high performance liquid chromatography (HPLC) using a Waters Autopurification System equipped with a Waters 2525 Pump, a Waters 2696 photodiode array detector, and a XTerra column (Part. No. 186000482, 5 μm, C18, 4.5×50 mm).

The HPLC analyses were performed using a linear gradient of 5% to 100% solvent B in solvent A in 7 min. Solvent A was H$_2$O with 0.05% TFA and solvent B was CH$_3$CN with 0.05% TFA (Method A).

HPLC Method B: Compounds were analyzed by reverse phase high performance liquid chromatography (HPLC) using a Waters System equipped with a Waters 600 Pump, a Waters 996 photodiode array detector, and a XTerra column (Part. No. 191372972, 5 μm, RP18, 4.6×250 mm).

HPLC analyses were performed using a linear gradient of 2% to 100% solvent B in solvent A in 25 min. Solvent A was H$_2$O with 0.05% TFA and solvent B was CH$_3$CN with 0.05% TFA (Method B).

The HPLC Chiral Analysis were performed on an unit composed of Merck D-7000 system manager, Merck-Lachrom L-7100 pump, Merck-Lachrom L-7200 autosampler, Merck-Lachrom L-7360 oven, Merck-Lachrom L-7400 UV-detector and a Jasco OR-1590 polarimeter.

For Compound 1 (free base), analytical chiral separation was performed on a Chiralpak® IA column (Daicel, 250×4.6 mm, 5 μm) available from Chiral Technology Europa (Illkirch, France). Semi-preparative chiral separation was performed on a Chiralpak® IA column (Daicel, 250×10 mm, 5 μm), amylose tris(3,5-dimethylphenylcarbamate) chiral stationary phases, available from Chiral Technology Europa (Illkirch, France), on an Knauer unit with pump, UV detector and a software to collect the different fractions.

For Compound 4 (free base), analytical chiral and semi-preparative separation were performed on a Sepapak®-2 HR column (Sepaserve GmbH, 250×4.6 mm, 3 μm), cellulose tris(3-chloro-4-methylphenylcarbamate) chiral stationary phases, on an Knauer unit with pump, UV detector and a software to collect the different fractions.

Hexane, 2-PrOH and ethanol, HPLC grade, were degassed and filtered on a 0.45 μm millipore membrane before use. Retention times (Rt) are reported in minutes, retention factors $k_i=(Rt_i-Rt_0)/Rt_0$ and enantioselectivity factor $\alpha=k_2/k_1$ are given. $Rt_0$ was determined by injection of tri-tertio-butyl benzene.

The optical rotatory powers of the salts were measured on a 241 MC Perkin-Elmer polarimeter with a sodium lamp (589 nm), a mercury lamp (578, 546 and 436 nm) and a double-jacketed 10 cm cell at 25° C.

Example 1

Preparation of (±)-threo-2-amino-3-(4-fluorophenyl)-3-hydroxy-1-(pyrrolidin-1-yl)propan-1-one hydrochloride, Compound 1

2-Isocyano-1-(pyrrolidin-1-yl)ethanone, BLE 04098

To stirred and cooled (0° C.) methyl 2-isocyanoacetate (96% technical grade, 5.0 g, 47.8 mmol) was slowly added in 0.75 h pyrrolidine (6.5 mL, 78 mmol). The mixture was stirred for 1.5 h with continued cooling and then concentrated. The resulting oil was co-evaporated twice from $CH_2Cl_2$:hexane to remove residual pyrrolidine. 2-Isocyano-1-(pyrrolidin-1-yl)ethanone, BLE 04098, was obtained as a yellow solid (6.85 g, 98% yield) and used in the next step without further purification.

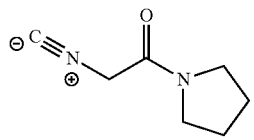

BLE 04098

MW: 138.17; Yield: 98%; Yellow Solid; Mp (° C.)=73.9.
$^1$H-NMR ($CDCl_3$, δ): 1.81-2.08 (m, 4H, 2×$CH_2$), 3.35-3.45 (m, 2H, $NCH_2$), 3.50-3.60 (m, 2H, $NCH_2$), 4.23 (s, 2H, $CH_2CO$).

(±)-trans-5-(4-Fluorophenyl)-4,5-dihydrooxazol-4-yl)(pyrrolidin-1-yl)methanone, TTA 13162

To a stirred and cooled (+4° C., water-ice bath) solution of KOH (3.5 g, 14.7 mmol) in MeOH (42 mL) was added successively 2-isocyano-1-(pyrrolidin-1-yl)ethanone, BLE 04098 (6.60 g, 48 mmol), and, portion-wise, 4-fluorobenzaldehyde (6.10 g, 48 mmol). The mixture was stirred for 7 h under a nitrogen atmosphere (4° C. to RT). The solvent was evaporated at 30° C. and the obtained residue was dried with a vacuum pump for 1 h. A mixture of water (30 mL) and ice (20 g) was then added to the residue with stirring. The solid was filtered and washed with water (3×20 mL) to give, after drying, (±)-trans-5-(4-fluorophenyl)-4,5-dihydrooxazol-4-yl)(pyrrolidin-1-yl)methanone, TTA 13162, as a white solid (11.1 g, 88% yield).

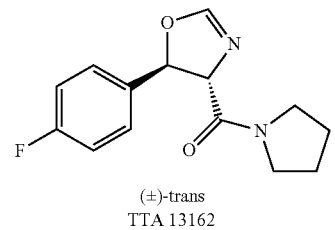

(±)-trans
TTA 13162

MW: 262.28; Yield: 88%; White Solid; Mp (° C.): 115.7. $R_f$=0.45 (EtOAc).
$^1$H NMR ($CD_3OD$, δ): 1.80-2.05 (m, 4H, 2×$CH_2$), 3.42-3.55 (m, 3H, 1.5×$CH_2N$), 3.90-3.98 (m, 1H, $CH_2N$), 4.55 (dd, 1H, J=7.7 Hz and J=2.2 Hz, CHN), 6.13 (d, 1H, J=7.7 Hz, CHO), 7.01-7.10 (m, 3H, 2×ArH and CH=N), 7.27-7.33 (d, 2H, 2×ArH).
$^{13}$C NMR ($CD_3OD$, δ): 24.1, 26.0, 46.4, 46.6, 75.7, 80.9, 115.8 (2×C, J=22.0 Hz), 127.7 (2×C, J=8.2 Hz), 135.5 (J=3.3 Hz), 155.2, 162.7 (J=247.5 Hz), 166.6.
MS-ESI m/z (% rel. Int.): 263.1 ([MH]$^+$, 100).
HPLC: Method A, detection UV 254 nm, RT=3.89 min, peak area 99.0%.

(±)-threo-2-Amino-3-(4-fluorophenyl)-3-hydroxy-1-(pyrrolidin-1-yl)propan-1-one hydrochloride, Compound 1

To a stirred solution of (±)-trans-5-(4-fluorophenyl)-4,5-dihydrooxazol-4-yl)(pyrrolidin-1-yl)methanone, TTA 13162 (200 mg, 0.76 mmol), in MeOH (8 mL) was added concentrated HCl (37%, 1.27 mL, 15.25 mmol). After heating at 50° C. for 3 h, the reaction mixture was concentrated, and the resulting yellow oil was co-evaporated twice with EtOAc before solidifying. Trituration ($CH_2Cl_2$) and drying afforded to (±)-threo-2-amino-3-(4-fluorophenyl)-3-hydroxy-1-(pyrrolidin-1-yl)propan-1-one hydrochloride, Compound 1, as a white solid (167 mg, 76% yield).

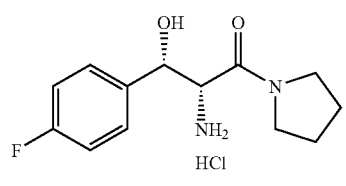

Compound 1
(±)-threo

MW: 288.10; Yield: 76%; White Solid; Mp (° C.)=179.3. $R_f$=0.4 ($CH_2Cl_2$:MeOH=9:1, free base).
$^1$H NMR ($CD_3OD$, δ): 1.40-1.85 (m, 4H, 2×$CH_2$), 2.30 (m, 1H, 0.5×$NCH_2$), 3.15-3.42 (m, 3H, 1.5×$NCH_2$), 4.11 (d, 1H, J=9.1 Hz, NCH), 7.10-7.19 (m, 2H, 2×ArH), 7.42-7.49 (m, 2H, 2×ArH). OCH not seen (masked by H$_2$O broad peak at 4.86). Signal detected in HSQC $^1$H-$^{13}$C correlation spectra at 4.86 ppm and 73.5 ppm.

$^{13}$C NMR (CD$_3$OD, δ): 24.8, 26.6, 47.2, 47.7, 59.4, 73.5, 116.4, (d, 2×C, J=21.8 Hz), 129.8 (d, 2×C, J=8.3 Hz), 136.7 (d, J=3.2 Hz), 164.4 (d, J=246.4 Hz), 166.2.

MS-ESI m/z (% rel. Int.): 253.1 ([MH]$^+$, 35), 97.9 (100).

HPLC: Method A, detection UV 260 nm, RT=3.72 min, peak area 96.4%.

Example 2

Preparation of (+)-threo-2-amino-3-(4-fluorophenyl)-3-hydroxy-1-(pyrrolidin-1-yl)propan-1-one hydrochloride, Compound 2, and (−)-threo-2-amino-3-(4-fluorophenyl)-3-hydroxy-1-(pyrrolidin-1-yl)propan-1-one hydrochloride, Compound 3

Samples are dissolved in EtOH. Compound 1 and its corresponding free base gave identical chromatograms in the chromatographic conditions used. Due to the lower solubility of the salt, the separation was done on the free base. The sign given by the on-line polarimeter is the sign of the free base in the solvent used for the chromatographic separation.

Preparation of (±)-threo-2-amino-3-(4-fluorophenyl)-3-hydroxy-1-pyrrolidin-1-yl-propan-1-one, Compound 1, free base To a solution of (±)-threo-2-amino-3-(4-fluorophenyl)-3-hydroxy-1-pyrrolidin-1-yl-propan-1-one hydrochloride Compound 1 (2.2 g, 7.6 mmol) in MeOH (100 mL) at 0° C. was added a solid form of Amberlite OH$^-$ (50 mL), which was prepared using Amberlite Cl$^-$ washed with H$_2$O (3×100 mL), treated with NaOH (1 N) (100 mL) for 10 min, filtered washed with H$_2$O (4×100 mL) and MeOH (4×100 mL). The heterogeneous mixture was stirred for 20 min, filtered and the volatiles of the filtrate were evaporated under reduced pressure to obtain (±)-threo-2-amino-3-(4-fluorophenyl)-3-hydroxy-1-pyrrolidin-1-yl-propan-1-one, Compound 1, free base (1.5 g) as a white solid.

Analytical Chiral Separation:

20 µL of a 1 mg/mL solution of Compound 1 in EtOH were injected on Chiralpak® IA: flow-rate=1 mL/min, temperature=25° C., mobile phase hexane:ethanol=8:2, detection on UV 220 nm and on polarimeter, Rt(+)=9.67 min, Rt(−)=12.01 min, k(+)=2.17, k(−)=2.94, α=1.35 and resolution Rs=2.92. (chromatogram FIG. 1).

Semi-Preparative Chiral Separation:

A 7.5 mg/mL solution of racemic Compound 1 free base (300 mg, 1.19 mmol) in EtOH (40 mL) was prepared and 500 µL of this solution was injected every 10 min on Chiralpak® IA, flow-rate=5 mL/min, mobile phase hexane:ethanol=8:2, detection on UV 254 nm. 80 successive injections were done. The two main fractions were identified on UV and collected in two different flasks. The solvent was removed in vacuo at 35° C. The resulting solid was dissolved in 50 mL of CH$_2$Cl$_2$ and then filtered on a 0.45 µm millipore membrane. After evaporation of CH$_2$Cl$_2$, the solid was dissolved in 50 mL of methanol and then filtered. The two fractions (135 mg each) have an enantiomeric excess higher than 99% (measured by analytical chiral HPLC).

Regeneration of the HCl Salts:

After the chiral separation, about 135 mg of each enantiomer (free base) was dissolved in 120 mL of EtOH and 8.6 mL of HCl (0.25 N, 4 eq) were added. The solvent was evaporated, and then 100 mL of EtOH was added and then removed in vacuo. The product was dissolved in 2 mL of MeOH, and 30 mL of EtOAc and 20 mL of hexane were added. The solvents were removed to give a white solid and the solids were dried over P$_2$O$_5$ under vacuum overnight. The enantiomeric excess (e.e.) of Compound 2 (white solid, 150 mg, 44% yield) and Compound 3 (white solid, 150 mg, 44% yield) was checked by analytical injection of the regenerated salts.

Rotatory Powers:

40.0 mg of the (+) enantiomer Compound 2 were dissolved in 4 mL of MeOH and this solution was put in the cell. For the (−) enantiomer Compound 3, 40.0 mg were also used.

(+)-threo-2-Amino-3-(4-fluorophenyl)-3-hydroxy-1-(pyrrolidin-1-yl)propan-1-one hydrochloride Compound 2

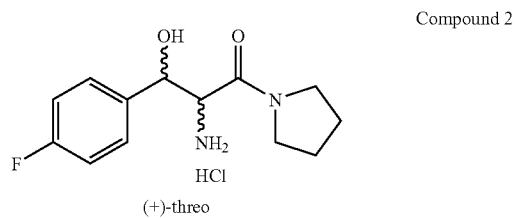

Compound 2

MW: 288.10; Yield: 44%; White Solid; Mp (° C.)=138.9.

e.e.=99.4% (chromatogram FIG. 2).

$\alpha^{25}_D$=+30.8 (MeOH, c=1)

$\alpha^{25}_{578}$=+32.1 (MeOH, c=1)

$\alpha^{25}_{546}$=+37.1 (MeOH, c=1)

$\alpha^{25}_{436}$=+68.3 (MeOH, c=1).

Example 3

(−)-threo-2-Amino-3-(4-fluorophenyl)-3-hydroxy-1-(pyrrolidin-1-yl)propan-1-one hydrochloride Compound 3

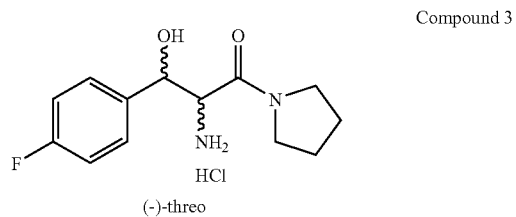

Compound 3

MW: 288.10; Yield: 44%; White Solid; Mp (° C.)=139.0.

e.e.=99.3% (chromatogram FIG. 3).

$\alpha^{25}_D$=−30.9 (MeOH, c=1)

$\alpha^{25}_{578}$=−32.2 (MeOH, C=1)

$\alpha^{25}_{546}$=−37.3 (MeOH, c=1)

$\alpha^{25}_{436}$=−68.9 (MeOH, c=1)

Determination of Absolute Configuration of Compound 3:

Compound 3 has been identified as (2R,3S)-2-amino-3-(4-fluorophenyl)-3-hydroxy-1-(pyrrolidin-1-yl)propan-1-one hydrochloride sesquihydrate by single crystal X-Ray diffraction (FIGS. 7 & 8).

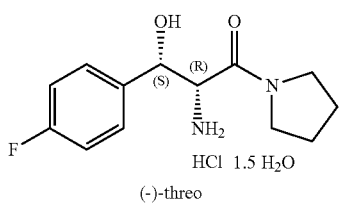

(−)-threo

3

By deduction, Compound 2 has been assigned as (2S,3R)-2-amino-3-(4-fluorophenyl)-3-hydroxy-1-(pyrrolidin-1-yl)propan-1-one hydrochloride.

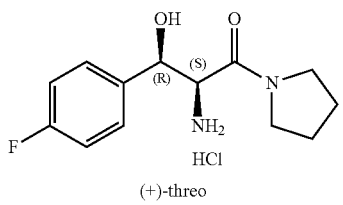

(+)-threo

2

Example 4

Preparation of (±)-erythro-2-amino-3-(4-fluorophenyl)-3-hydroxy-1-(pyrrolidin-1-yl)propan-1-one hydrochloride, Compound 4 tert-Butyl (±)-threo-1-(4-fluorophenyl)-1-hydroxy-3-oxo-3-(pyrrolidin-1-yl)propan-2-ylcarbamate, SLA 19084

To a solution of (±)-threo-2-amino-3-(4-fluorophenyl)-3-hydroxy-1-(pyrrolidin-1-yl)propan-1-one hydrochloride, Compound 1 (3.00 g, 10.39 mmol), in $CH_2Cl_2$ (104 mL) was added $Et_3N$ (4.33 mL, 31.17 mmol). The mixture was cooled to 0° C. under $N_2$ and di-tert-butyl dicarbonate ($Boc_2O$) (2.27 g, 10.39 mmol) was added. The mixture was allowed to warm to 25° C. with continuous stirring for 16 h. The solution was washed with brine (3×50 mL), dried over sodium sulfate, filtered and evaporated to dryness. The residue obtained was purified by column chromatography ($SiO_2$) using a gradient of 0-1% MeOH in $CH_2Cl_2$ [v/v] to give ter-butyl (±)-threo-1-(4-fluorophenyl)-1-hydroxy-3-oxo-3-(pyrrolidin-1-yl)propan-2-ylcarbamate, SLA 19084 (2.84 g, 78% yield), as a pale yellow solid.

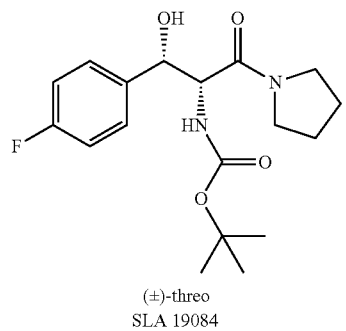

(±)-threo
SLA 19084

MW: 352.40; Yield: 78%; Pale Yellow solid; Mp (° C.)=136.1 (dec).
$R_f$: 0.30 (MeOH:$CH_2Cl_2$=99:1).
$^1H$ NMR (CDCl$_3$, δ): 1.33 (s, 9H, C(CH$_3$)$_3$), 1.76-1.88 (m, 4H, 2×CH$_2$), 3.11-3.55 (m, 4H, 2×CH$_2$), 4.51 (d, 1H, J=5.6 Hz, NCH), 4.60 (d, 1H, J=1.8 Hz, OH), 5.01 (d, 1H, J=3.6 Hz, OCH), 5.56 (d, 1H, J=8.7 Hz, NH), 7.02 (t, 2H, J=8.7 Hz, 2×ArH), 7.35-7.44 (m, 2H, 2×ArH).
$^{13}C$ NMR (CDCl$_3$, δ): 23.9, 25.7, 28.0 (3×C), 45.8, 46.4, 56.9, 73.5, 80.0, 114.8 (d, J=22.6 Hz 2×C), 127.8 (d, J=7.5 Hz, 2×C), 135.1, 155.7, 162.2 (d, J=249.1 Hz, CF), 169.5.
MS-ESI m/z (% rel. Int.): 375.1 (12, [M+Na]$^+$).
HPLC: Method A, detection at 254 nm, RT=5.17 min, peak area 99%.

tert-Butyl (±)-1-(4-fluorophenyl)-1,3-dioxo-3-(pyrrolidin-1-yl)propan-2-ylcarbamate, SLA 19086

To a solution of tert-butyl (±)-threo-1-(4-fluorophenyl)-1-hydroxy-3-oxo-3-(pyrrolidin-1-yl)propan-2-ylcarbamate, SLA 19084 (2.79 g, 7.92 mmol), in $CH_2Cl_2$ (80 mL) was added at 0° C. 1,1,1-triacetoxy-1,1-dihydro-1,2-benziodoxol-3-(1H)-one (Dess-Martin periodinane, 3.36 g, 7.92 mmol). This mixture was stirred overnight at 25° C., diluted with $CH_2Cl_2$ (100 mL) and washed successively with saturated NaHCO$_3$ (2×50 mL), 1 N Na$_2$S$_2$O$_3$ (2×50 mL) and brine (2×50 mL). The organic layer was dried over MgSO$_4$, filtered and evaporated to dryness. The residue obtained was purified by column chromatography ($SiO_2$) using a gradient of 0-1% MeOH in $CH_2Cl_2$ [v/v] to give tert-butyl (±)-1-(4-fluorophenyl)-1,3-dioxo-3-(pyrrolidin-1-yl)propan-2-ylcarbamate, SLA 19086 (2.11 g, 76% yield), as a pale yellow solid.

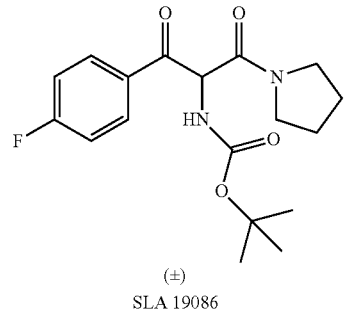

(±)
SLA 19086

MW: 350.38; Yield: 76%; Pale Yellow Solid; Mp (° C.)=156.6 (dec).
$^1H$ NMR (CDCl$_3$, δ): 1.40 (s, 9H, C(CH$_3$)$_3$), 1.85-1.98 (m, 4H, 2×CH$_2$), 3.42-3.67 (m, 4H, 2×CH$_2$), 5.72 (d, 1H, J=7.9 Hz, NCH), 6.08 (d, 1H, J=7.8 Hz, NH), 7.14 (t, 2H, J=8.6 Hz, 2×ArH), 8.06-8.13 (m, 2H, 2×ArH).
$^{13}C$ NMR (CDCl$_3$, δ): 23.7, 25.7, 26.9 (3×C), 46.6, 46.7, 60.0, 80.6, 115.8 (d, J=22.6 Hz, 2×C), 131.3, 132.5 (d, J=7.5 Hz, 2×C), 155.1, 164.8, 166.0 (d, J=256.6 Hz, CF), 192.4.
MS-ESI m/z (% rel. Int.): 351.0 (28, [MH]$^+$).
HPLC: Method A, detection at 254 nm, RT=5.72 min, peak area 80%.

Mixture of tert-butyl (±)-erythro-1-(4-fluorophenyl)-1-hydroxy-3-oxo-3-(pyrrolidin-1-yl)propan-2-ylcarbamate and tert-butyl (±)-threo-1-(4-fluorophenyl)-1-hydroxy-3-oxo-3-(pyrrolidin-1-yl)propan-2-ylcarbamate as a erythro:threo mixture in a ratio of 80:20, SLA 19088

To a solution of tert-butyl (±)-1-(4-fluorophenyl)-1,3-dioxo-3-(pyrrolidin-1-yl)propan-2-ylcarbamate, SLA 19086

(1.00 g, 2.85 mmol), in MeOH (29 mL) cooled to ° C. was added NaBH₄ (119 mg, 3.14 mmol) as a solid. The mixture was stirred for 3 h at 4° C. All the volatiles were evaporated to give a solid that was partitioned using EtOAc (100 mL) and 0.5 M NaOH (2×50 mL). The organic layer was dried over sodium sulfate, filtered and evaporated to dryness. The residue obtained was purified by column chromatography (SiO₂) using a gradient of 0-1% MeOH in CH₂Cl₂ [v/v] to give a mixture of tert-butyl (±)-erythro-1-(4-fluorophenyl)-1-hydroxy-3-oxo-3-(pyrrolidin-1-yl)propan-2-ylcarbamate and tert-butyl (±)-threo-1-(4-fluorophenyl)-1-hydroxy-3-oxo-3-(pyrrolidin-1-yl)propan-2-ylcarbamate as a (±)-erythro:(±)-threo mixture in a ratio of 80:20, SLA 19088 (700 mg, 70% yield), as a pale yellow solid.

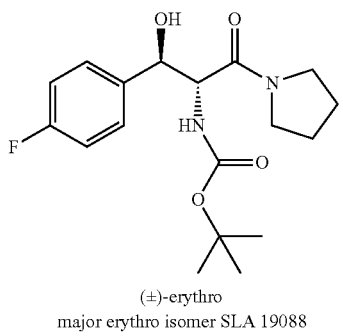

(±)-erythro
major erythro isomer SLA 19088

MW: 352.40; Yield: 70%; Pale Yellow solid; Mp (° C.) mixture=158.9 (dec).

$R_f$: 0.30 (MeOH:CH₂Cl₂=1:99).

¹H NMR (CDCl₃, δ): major erythro isomer 1.42 (s, 9H, C(CH₃)₃), 1.63-1.85 (m, 4H, 2×CH₂), 2.77-3.56 (m, 4H, 2×CH₂), 4.58-4.62 (m, 1H, NCH), 4.90-4.94 (m, 1H, OCH), 5.00 (bs, 1H, OH), 5.73 (d, 1H, J=8.9 Hz, NH), 7.02 (t, 2H, J=8.7 Hz, 2×ArH), 7.28-7.37 (m, 2H, 2×ArH).

¹³C NMR (CD₃OD, δ): major erythro isomer 27.8, 29.3, 31.1 (3×C), 49.7, 61.1, 76.7, 83.1, 118.2 (2×C, d, J=15.1 Hz), 132.8 (2×C, d, J=7.5 Hz), 141.5, 159.6, 164.8 (d, J=241.5 Hz, CF), 168.0, 173.3.

MS-ESI m/z (% rel. Int.): 375.1 (37, [M+Na]⁺).

HPLC: Method A, detection at 254 nm, RT=5.23 min, mixture erythro:threo=80:20, peak area 99%.

(±)-erythro-2-Amino-3-(4-fluorophenyl)-3-hydroxy-1-pyrrolidin-1-yl-propan-1-one hydrochloride, Compound 4

To a solution of trifluoroacetic acid (2.70 mL) in CH₂Cl₂ (18 mL) was added a 80:20 mixture of tert-butyl (±)-erythro-1-(4-fluorophenyl)-1-hydroxy-3-oxo-3-(pyrrolidin-1-yl)propan-2-ylcarbamate and tert-butyl (±)-threo-1-(4-fluorophenyl)-1-hydroxy-3-oxo-3-(pyrrolidin-1-yl)propan-2-ylcarbamate, SLA 19088 (620 mg, 0.176 mmol), at 0° C. and the solution was warmed to 25° C. with continuous stirring for 2 h. The volatiles were evaporated to obtain a pale yellow oil that was dissolved in MeOH at 0° C. and treated with a solid form of Amberlite OH⁻ (10 mL) that was obtained using Amberlite Cl⁻ washed with H₂O (3×100 mL), stirred with 1 N NaOH (100 mL) for 10 min, filtered, washed with H₂O (4×100 mL) and MeOH (2×100 mL). The heterogeneous mixture was stirred for 20 min filtered and evaporated to dryness to give a yellow solid (348 mg). 100 mg of the crude product was purified by preparative HPLC using as eluent a gradient from 0% eluent B to 12% eluent B in eluent A in 7 min. with a Prep C18 Xterra® 19×50 mm column 186001108—Eluent A: H₂O (0.05% TFA), eluent B: CH₃CN (0.05% TFA). After evaporation to dryness, the obtained solid (62 mg) was dissolved in MeOH (3 mL), treated at 0° C. with a 0.18 M HCl solution (113 µL) and stirred for 15 min at 0° C. to give, after evaporation to dryness, (±)-threo-2-amino-3-(4-fluorophenyl)-3-hydroxy-1-(pyrrolidin-1-yl)propan-1-one hydrochloride, Compound 4, as a white solid (49 mg, 38% yield).

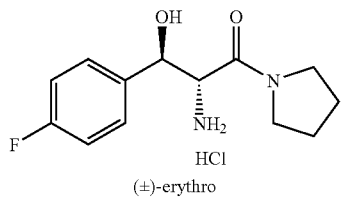

Compound 4

(±)-erythro

MW: 288.75; Yield: 38%; White Solid; Mp (° C.): 136.9.

¹H NMR (CD₃OD, δ): 1.77-1.90 (m, 4H, 2×CH₂), 3.00-3.53 (m, 4H, 2×CH₂), 4.42 (d, 1H, J=5.5 Hz, NCH), 5.12 (d, 1H, J=5.6 Hz, OCH), 7.14 (t, 2H, J=8.5 Hz, 2×ArH), 7.46 (t, 2H, J=8.2 Hz, 2×ArH).

¹³C NMR (CD₃OD, δ): 24.9, 26.8, 48.0, 48.2, 57.7, 72.4, 116.6 (d, J=22.6 Hz, 2×C), 130.2 (d, J=7.6 Hz, 2×C), 136.1, 164.1 (d, J=241.5 Hz, CF), 166.1.

MS-ESI m/z (% rel. Int.): 253.0 (36, [MH]⁺).

HPLC: Method A, detection at 254 nm, RT=3.58 min, peak area 99%.

Example 5

Preparation of (+)-erythro-2-amino-3-(4-fluorophenyl)-3-hydroxy-1-(pyrrolidin-1-yl)propan-1-one hydrochloride, Compound 5, and (−)-erythro-2-amino-3-(4-fluorophenyl)-3-hydroxy-1-(pyrrolidin-1-yl)propan-1-one hydrochloride, Compound 6

Samples are dissolved in EtOH. Compound 4 and its corresponding free base gave identical chromatograms in the chromatographic conditions used. Due to the lower solubility of the salt, the separation was done on the free base. The sign given by the on-line polarimeter is the sign of the free base in the solvent used for the chromatographic separation.
Analytical Chiral Separation:

20 µL of a 1 mg/mL solution of Compound 4 free base were injected on Sepapak®-2 HR column: flow-rate=1 mL/min, temperature=25° C., mobile phase hexane:ethanol=6:4, detection on UV 220 nm and on polarimeter, Rt(+)=9.37 min, Rt(−)=11.05 min, k(+)=1.91, k(−)=2.43, α=1.27 and resolution Rs=2.92. (chromatogram FIG. 4).

Preparation of (±)-erythro-2-amino-3-(4-fluorophenyl)-3-hydroxy-1-pyrrolidin-1-yl-propan-1-one, Compound 4, free base To a solution of (±)-erythro-2-amino-3-(4-fluorophenyl)-3-hydroxy-1-pyrrolidin-1-yl-propan-1-one trifluoroacetate (326 mg, 0.89 mmol) in MeOH (10 mL) at 0° C. was added a solid form of Amberlite OH⁻ (5 mL) that was prepared using Amberlite Cl⁻ washed with H₂O (3×100 mL), treated with 1 N NaOH (100 mL) for 10 min, filtered washed with H₂O (4×100 mL) and MeOH (4×100 mL). The heterogeneous mixture was stirred for 20 min, filtered and the volatiles of the filtrate were evaporated under reduced pressure to obtain (±)-erythro-2-amino-3-(4-fluorophenyl)-3-hydroxy-1-pyrrolidin-1-yl-propan-1-one, Compound 4, free base (224 mg) as a white solid.

Semi-Preparative Chiral Separation:

A 5 mg/mL solution of racemic Compound 4, free base (190 mg) was prepared and 400 µL of this solution were injected every 10 min on Sepapak®-2 HR, flow-rate=1 mL/min, mobile phase hexane:ethanol=7:3, detection on UV 254 nm. 95 Successive injections were done. The two main fractions were identified on UV and collected in two different flasks. The solvent was removed in vacuo at 35° C. The resulting solid was dissolved in 50 mL of $CH_2Cl_2$ and then filtered on a 0.45 µm millipore membrane. After evaporation of $CH_2Cl_2$, the solid was dissolved in 50 mL of methanol and then filtered. The two fractions (65 mg each) have an enantiomeric excess higher than 98% (as measured by analytical chiral HPLC).

Regeneration of the HCl Salts:

After the chiral separation, about 65 mg of each enantiomer (free base) were dissolved in 100 mL of EtOH and 4.2 mL of HCl (0.25 N, 4 eq) were added. The solvent was evaporated, and then 100 mL of EtOH were added and then removed in vacuo. The product was dissolved in 2 mL of MeOH, then 30 mL of EtOAc and 50 mL of hexane were added. The solvents were removed to give a solid and the solids were dried over $P_2O_5$ under vacuum overnight. The enantiomeric excess (e.e.) of Compound 5 (white solid, 75 mg, 34.5% yield) and Compound 6 (white solid, 75 mg, 34.5% yield) was checked by analytical injection of the regenerated salts.

Rotatory Powers:

20.0 mg of the (+) enantiomer Compound 5 were dissolved in 2 mL of MeOH and this solution was put in the cell. For the (−) enantiomer Compound 6, 30.0 mg were dissolved in 3 mL of MeOH.

(+)-erythro-2-Amino-3-(4-fluorophenyl)-3-hydroxy-1-(pyrrolidin-1-yl)propan-1-one hydrochloride Compound 5

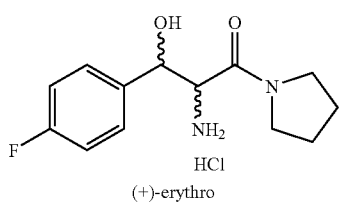

Compound 5
(+)-erythro

MW: 288.10; Yield: 34.5%; White Solid; Mp (° C.)=143.3. e.e.=98.6% (chromatogram FIG. 5).
$\alpha^{25}_D$=+28.2 (MeOH, c=1)
$\alpha^{25}_{578}$=+29.4 (MeOH, c=1)
$\alpha^{25}_{546}$=+34.9 (MeOH, c=1)
$\alpha^{25}_{436}$=+62.7 (MeOH, c=1).

(−)-erythro-2-Amino-3-(4-fluorophenyl)-3-hydroxy-1-(pyrrolidin-1-yl)propan-1-one hydrochloride Compound 6

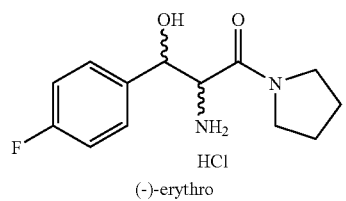

Compound 6
(−)-erythro

MW: 288.10; Yield: 34.5%; White Solid; Mp (° C.)=143.8. e.e.=98.2% (chromatogram FIG. 6).
$\alpha^{25}_D$=−28.0 (MeOH, c=1)
$\alpha^{25}_{578}$=−29.3 (MeOH, c=1)
$\alpha^{25}_{545}$=−34.7 (MeOH, c=1)
$\alpha^{25}_{436}$=62.3 (MeOH, c=1)

Example 6

Preparation of (±)-threo-2-amino-3-(4-fluorophenyl)-3-hydroxy-1-morpholin-4-yl-propan-1-one hydrochloride, Compound 7

2-Isocyano-1-morpholinoethanone, SLA 19178

To stirred and cooled (0° C.) methyl 2-isocyanoacetate (96% technical grade, 1.0 g, 10.09 mmol) was slowly added morpholine (1.05 g, 12.11 mmol). The mixture was stirred for 1 h with continuous stirring at room temperature and then concentrated. The resulting oil was co-evaporated twice from a mixture $CH_2Cl_2$:hexane to obtain crude 2-isocyano-1-morpholinoethanone, SLA 19178, as a yellow oil (1.65 g, 99% yield) and used in the next step without further purification.

SLA 19178

MW: 154.17; Yield: 99%; Yellow Oil.
$^1$H-NMR (CDCl$_3$, δ): 3.40-3.48 (m, 2H, CH$_2$), 3.58-3.67 (m, 2H, CH$_2$), 3.70-3.74 (m, 4H, 2×CH$_2$), 4.25 (s, 2H, CH$_2$CO).

(±)-trans-(5-(4-Fluorophenyl)-4,5-dihydrooxazol-4-yl)(morpholino)methanone, SLA 19180

To a stirred and cooled (0° C.) solution of KOH (0.60 g, 10.70 mmol) in MeOH (100 mL) was added successively 4-fluorobenzaldehyde (1.21 g, 9.73 mmol) and 2-isocyano-1-morpholinoethanone SLA 19178 (1.50 g, 9.73 mmol). The solution was stirred 16 h (0° C. to RT) and then concentrated. The residue was partitioned between $CH_2Cl_2$ (20 mL) and brine (20 mL). The organic layer was separated and the aqueous layer was extracted with $CH_2Cl_2$ (3×20 mL). The organic layers were combined and washed with brine (30 mL), dried over MgSO$_4$, filtered and evaporated to give a pale crude yellow solid. Purification of this crude product by column chromatography (Florisil®, eluent CH$_2$Cl$_2$:MeOH=98:2) yielded, after evaporation and drying, (±)-trans-(5-(4-fluorophenyl)-4,5-dihydrooxazol-4-yl)(morpholino)methanone, SLA 19180, as a pale yellow oil (0.65 g, 24% yield).

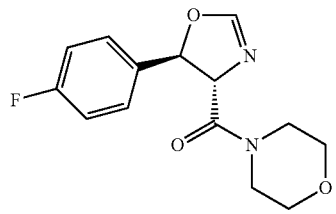

SLA 19180

MW: 278.28; Yield: 24%; Pale Yellow Oil.
R$_f$: 0.30 (CH$_2$Cl$_2$:MeOH=98:2).
$^1$H-NMR (CDCl$_3$, δ): 3.40-3.99 (m, 8H, 4×CH$_2$), 4.60 (d, 1H, J=7.6 Hz, NCH), 6.20 (d, 1H, J=7.6 Hz, OCH), 6.90-7.10 (m, 3H, 2×ArH & OCHN), 7.23-7.32 (m, 2H, 2×ArH).
$^{13}$C-NMR(CDCl$_3$, δ): 42.7, 46.1, 53.5, 66.5, 66.7, 74.4, 80.4, 116.2, 115.7 (d, 2×C, J=15.1 Hz), 127.6 (d, 2×C, J=7.6 Hz), 135.4 (d, J=3.0 Hz), 155.1, 162.6 (d, J=247.5 Hz), 166.9.
MS-ESI m/z (% rel. Int.): 279.2 ([MH]$^+$, 37), 114.0 (100).

(±)-threo-2-Amino-3-(4-fluorophenyl)-3-hydroxy-1-morpholin-4-yl-propan-1-one hydrochloride, Compound 7

To a stirred solution of (±)-trans-(5-(4-fluorophenyl)-4,5-dihydrooxazol-4-yl)(morpholino)methanone, SLA 19180 (623 mg, 2.24 mmol), in MeOH (23 mL) was added concentrated HCl (37%, 206 µL, 2.46 mmol). After heating at 52° C. for 4 h, the reaction mixture was concentrated and the resulting yellow oil was co-evaporated twice with EtOAc before solidifying. Trituration with CH$_2$Cl$_2$ and drying afforded to (±)-threo-2-amino-3-(4-fluorophenyl)-3-hydroxy-1-morpholin-4-yl-propan-1-one hydrochloride, Compound 7, as a pale yellow solid (581 mg, 85% yield).

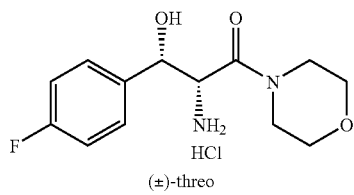

Compound 7

(±)-threo

MW: 304.75; Yield: 85%; Pale Yellow Solid; Mp (° C.)=113.4.
$^1$H NMR (CD$_3$OD, δ): 2.65-2.80 (m, 2H, CH$_2$), 3.03-3.60 (m, 6H, 3×CH$_2$), 4.47 (d, 1H, J=8.9 Hz, NCH), 4.76-4.84 (m, 1H, OCH), 7.19 (t, 2H, J=8.6 Hz, 2×ArH), 7.49 (t, 2H, J=8.7 Hz, 2×ArH).
$^{13}$C-NMR (CD$_3$OD, δ): 43.6, 47.2, 56.7, 66.9, 67.2, 73.8, 116.7 (2×C, J=22.6 Hz), 130.2 (2×C, J=8.38 Hz), 136.8 (d, J=3.25 Hz), 165.0 (d, J=241.5 Hz), 166.7.
MS-ESI m/z (% rel. Int.): 269.2 ([MH]$^+$, 22), 114.0 (100).
HPLC: Method A, detection UV 254 nm, RT=3.3 min, peak area 98.8%.

Example 7

Preparation of (±)-threo-2-Amino-3-(4-fluorophenyl)-3-hydroxy-1-(piperidin-1-yl)propan-1-one hydrochloride Compound 8

2-Isocyano-1-(piperidin-1-yl)ethanone, SLA 07116B

To stirred and cooled (0° C.) methyl 2-isocyanoacetate (96% technical grade, 2.46 g, 24.63 mmol) was slowly added piperidine (3.22 mL, 37.85 mmol). The mixture was stirred for 1 h with continuous stirring at room temperature and then concentrated. The residue was dissolved in dichloromethane (50 mL) and the organic layer was washed with 10% aqueous citric acid (2×25 mL), dried over MgSO$_4$, filtered and evaporated. 2-Isocyano-1-(piperidin-1-yl)ethanone, SLA 07116B, was obtained as an orange solid (3.13 g, 83% yield) that was used in the next step without further purification.

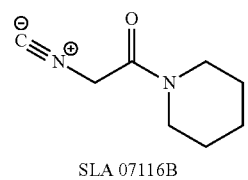

SLA 07116B

MW: 152.19; Yield: 83%; Orange Solid; Mp (° C.): 81.6.
$^1$H-NMR (CDCl$_3$, δ): 1.56-1.74 (m, 6H, 3×CH$_2$), 3.33 (t, 2H, J=5.7 Hz, CH$_2$N), 3.58 (t, 2H, J=5.7 Hz, CH$_2$N), 4.29 (s, 2H, CH$_2$CO).

(±)-trans-(5-(4-Fluorophenyl)-4,5-dihydrooxazol-4-yl)(piperidin-1-yl)methanone, SLA 19138

To a stirred and cooled (0° C.) solution of KOH (0.19 g, 2.89 mmol) in MeOH (27 mL) was added successively 4-fluorobenzaldehyde (0.49 g, 3.94 mmol) and 2-isocyano-1-(piperidin-1-yl)ethanone, SLA 07116B (0.40 g, 2.63 mmol). The solution was stirred 16 h (0° C. to RT) and then concentrated. The residue was partitioned between CH$_2$Cl$_2$ (20 mL) and brine (20 mL). The organic layer was separated and the aqueous layer was extracted with CH$_2$Cl$_2$ (3×20 mL). The combined organic layers were washed with brine (30 mL), dried over MgSO$_4$, filtered and evaporated to give a pale crude yellow solid. Purification of the crude product by column chromatography (Florisil®; eluent CH$_2$Cl$_2$:MeOH=98:2) yielded, after evaporation and drying, (±)-trans-(5-(4-fluorophenyl)-4,5-dihydrooxazol-4-yl)(piperidin-1-yl) methanone, SLA 19138, as a pale yellow oil (0.66 g, 91% yield).

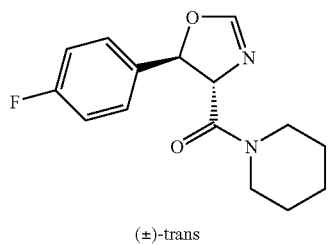

(±)-trans
SLA 19138

MW: 276.31; Yield: 91%; Pale Yellow Oil.
R$_f$: 0.30 (CH$_2$Cl$_2$:MeOH=98:2).

¹H-NMR (CDCl₃, δ): 1.56-1.66 (m, 6H, 3×CH₂), 3.43-3.56 (m, 2H, NCH₂), 3.68-3.79 (m, 2H, NCH₂), 4.65 (dd, 1H, J=2.1 Hz, J=7.6 Hz, NCH), 6.18 (d, 1H, J=7.6 Hz, OCH), 7.00 (d, 1H, J=2.1 Hz, OCH=N), 7.02-7.08 (m, 2H, 2×ArH), 7.26-7.35 (m, 2H, 2×ArH).

¹³C-NMR (CDCl₃, δ): 24.4, 25.5, 26.4, 43.7, 46.8, 74.5, 81.0, 115.8 (d, 2×C, J=21.9 Hz), 127.8 (d, 2×C, J=7.6 Hz), 135.6 (d, J=3.0 Hz), 154.9, 162.7 (d, J=247.5 Hz), 166.3.

MS-ESI m/z (% rel. Int.): 277.1 ([MH]⁺, 20), 111.8 (100).

(±)-threo-2-Amino-3-(4-fluorophenyl)-3-hydroxy-1-(piperidin-1-yl)propan-1-one hydrochloride, Compound 8

To a stirred solution of (±)-trans-(5-(4-fluorophenyl)-4,5-dihydrooxazol-4-yl)(piperidin-1-yl)methanone, SLA 19138 (660 mg, 2.39 mmol), in MeOH (24 mL) was added concentrated HCl (37%, 2.00 mL, 23.90 mmol). After heating at 52° C. for 1.5 h the reaction mixture was concentrated and the resulting yellow oil was co-evaporated twice with EtOAc before solidifying. Trituration (CH₂Cl₂) and drying afforded to (±)-threo-2-amino-3-(4-fluorophenyl)-3-hydroxy-1-(piperidin-1-yl)propan-1-one hydrochloride, Compound 8, as a pale yellow solid (405 mg, 56% yield).

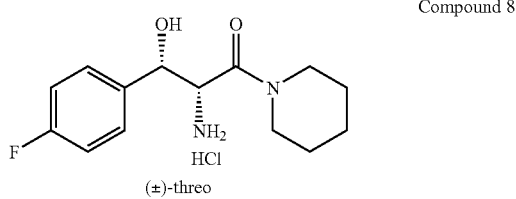

Compound 8
(±)-threo

MW: 302.77; Yield: 56%; Pale Yellow Solid; Mp (° C.)=174.6.

R_f=0.3 (CH₂Cl₂:MeOH=95:5, free base).

¹H NMR (CD₃OD, δ): 0.65-0.85 (m, 1H, 0.5×CH₂), 1.24-1.54 (m, 5H, 2.5×CH₂), 2.66-2.74 (m, 1H, 0.5×NCH₂), 3.08-3.18 (m, 1H, 0.5×NCH₂), 3.28-3.39 (m, 1H, 0.5×NCH₂), 3.43-3.50 (m, 1H, 0.5×NCH₂), 4.47 (d, 1H, J=8.8 Hz, NCH), 4.82 (d, 1H, J=8.9 Hz, OCH) 7.15 (t, 2H, J=8.8 Hz, 2×ArH), 7.45 (t, 2H, J=8.6 Hz, 2×ArH).

¹³C-NMR (CD₃OD, δ): 24.9, 26.2, 26.7, 44.3, 47.8, 56.7, 73.8, 116.6 (d, 2×C, J=21.9 Hz), 130.0 (d, 2×C, J=8.3 Hz), 136.5 (d, J=3.0 Hz), 164.4 (d, J=246.0 Hz), 166.2.

MS-ESI m/z (% rel. Int.): 267.2 ([MH]⁺, 26), 112.1 (100).

Example 8

Preparation of (±)-threo-2-amino-N,N-diethyl-3-(4-fluorophenyl)-3-hydroxypropanamide hydrochloride, Compound 9

N,N-Diethyl-2-isocyanoacetamide, SLA 19136

To stirred and cooled (0° C.) methyl 2-isocyanoacetate (96% technical grade, 2.51 g, 25.36 mmol) was slowly added diethylamine (2.78 g, 38.04 mmol). The mixture was stirred for 16 h at 52° C. and then concentrated. The resulting oil was co-evaporated twice with CH₂Cl₂:hexane, and purified using column chromatography (SiO₂, eluent cyclohexane: EtOAc=6:4) to yield after evaporation and drying N₃N-diethyl-2-isocyanoacetamide, SLA 19136, as a brown oil (890 g, 25% yield).

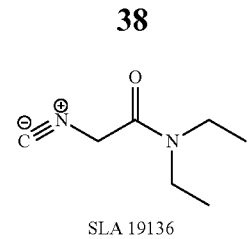

SLA 19136

MW: 140.18; Yield: 25%; Brown Oil.

¹H-NMR (CDCl₃, δ): 1.00-1.35 (m, 6H, 2×CH₃), 3.15-3.35 (m, 2H, NCH₂), 3.36-3.55 (m, 2H, NCH₂), 4.30 (s, 2H, CH₂CO).

MS-ESI m/z (% rel. Int.): 140.9 ([MH]⁺, 100).

(±)-trans-N,N-Diethyl-5-(4-fluorophenyl)-4,5-dihydrooxazole-4-carboxamide, SLA 19142

To a stirred and cooled (0° C.) solution of KOH (0.26 g, 3.92 mmol) in MeOH (36 mL) was added successively 4-fluorobenzaldehyde (0.443 g, 3.56 mmol) and N,N-diethyl-2-isocyanoacetamide (0.50 g, 3.57 mmol). The solution was stirred for 16 h (0° C. to RT) and then concentrated. The residue was partitioned between CH₂Cl₂ (20 mL) and brine (20 mL). The organic layer was separated and the desired product was extracted with CH₂Cl₂ (3×20 mL). The combined organic layers were washed with brine (30 mL), dried over MgSO₄, filtered and evaporated. A pale crude yellow solid was obtained the (±)-trans-N,N-diethyl-5-(4-fluorophenyl)-4,5-dihydrooxazole-4-carboxamide, SLA 19142, as a brown oil (0.86 g, 91% yield).

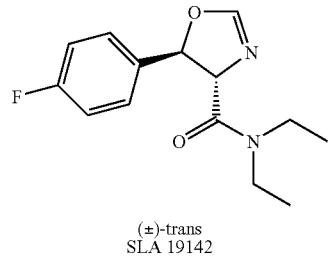

(±)-trans
SLA 19142

MW: 264.30; Yield: 91%; Brown Oil.

¹H-NMR (CDCl₃, δ): 1.12-1.20 (m, 6H, 2×CH₃), 3.17-3.60 (m, 4H, 2×NCH₂), 4.60 (d, 1H, J=6.0 Hz, NCH), 6.14 (d, 1H, J=6.0 Hz, OCH), 6.90-7.11 (m, 2H, ArH & OCH=N), 7.25-7.31 (m, 2H, 2×ArH), 7.33-7.43 (m, 1H, 1×ArH).

MS-ESI m/z (% rel. Int.): 265.2 ([MH]⁺, 23), 100 (100).

(±)-threo-2-Amino-N,N-diethyl-3-(4-fluorophenyl)-3-hydroxypropanamide hydrochloride, Compound 9

To a stirred solution of (±)-trans-N,N-diethyl-5-(4-fluorophenyl)-4,5-dihydrooxazole-4-carboxamide, SLA 19142 (0.86 mg, 3.25 mmol), in MeOH (32.5 mL) was added concentrated HCl (2.71 mL, 32.50 mmol). After heating at 52° C. for 2 h, the reaction mixture was concentrated and the resulting yellow oil was co-evaporated twice with EtOAc.

To a solution of crude (±)-threo-2-amino-N,N-diethyl-3-(4-fluorophenyl)-3-hydroxypropanamide hydrochloride, SLA 19144 (0.96 g), in MeOH (65 mL) at 0° C. was added a OH⁻ form of Amberlite OH⁻ (25 mL) that was prepared using Amberlite Cl⁻ washed with H₂O (3×50 mL), treated with NaOH (1N) (50 mL) for 10 min, filtered, washed with H₂O (4×50 mL) and MeOH (4×50 mL). The heterogeneous mixture was stirred for 20 min filtered and evaporated to dryness to give a yellow solid (289 mg). This crude product (325 mg) was purified using preparative HPLC using a gradient from 8% eluent B to 12% eluent B in eluent A in 10 min. with a Prep C18 Xterra 19×50 mm column 186001108. Eluent A: H$_2$O (0.05% TFA); eluent B: CH$_3$CN (0.05% TFA). The resulting solid (240 mg) was dissolved in MeOH (3 mL) at 0° C. and treated with a solution of HCl (0.123 M) in MeOH and stirred for 15 min at 0° C. to give, after evaporation and drying, (±)-threo-2-amino-N,N-diethyl-3-(4-fluorophenyl)-3-hydroxypropanamide hydrochloride, Compound 9 (240 mg, 53% yield) as a pale yellow solid.

Compound 9

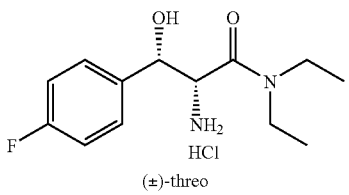

(±)-threo

MW: 290.76; Yield: 53%; Pale Yellow Solid; Mp (° C.)=169.3.

R$_f$=0.3 (CH$_2$Cl$_2$:MeOH=95:5, free base).

$^1$H NMR (CD$_3$OD, δ): 0.88 (t, 3H, J=6.0 Hz, CH$_3$), 0.99 (t, 3H, J=6.0 Hz, CH$_3$), 2.60-2.74 (m, 1H, 0.5×NCH$_2$), 2.79-2.93 (m, 1H, 0.5×NCH$_2$), 2.99-3.11 (m, 1H, 0.5×NCH$_2$), 3.44-3.56 (m, 1H, 0.5×NCH$_2$), 4.27 (d, 1H, J=9.1 Hz, NCH), 4.88 (d, 1H, J=9.4 Hz, OCH), 7.08-7.16 (m, 2H, 2×ArH), 7.42-7.48 (m, 2H, 2×ArH).

$^{13}$C-NMR (CD$_3$OD, δ): 12.7, 13.9, 41.8, 42.8, 57.1, 73.9, 116.5 (d, 2×C, J=21.8 Hz), 130.0 (d, 2×C, J=8.29 Hz), 136.7, 164.5 (d, J=246.47 Hz), 167.2.

MS-ESI m/z (% rel. Int.): 255.2 ([MH]$^+$, 16), 100.0 (100).

Example 9

Preparation of (±)-threo-2-amino-3-(4-fluorophenyl)-3-hydroxy-1-(4-methylpiperidin-1-yl)propan-1-one hydrochloride, Compound 10

Potassium (±)-trans-5-(4-fluorophenyl)-4,5-dihydrooxazole-4-carboxylate, ANP 20162

To a stirred and cooled (4° C.) solution of KOH (3.04 g, 46.02 mmol) in MeOH (50 mL) were slowly added 4-fluorobenzaldehyde (4.13 mL, 38.35 mmol) and methyl 2-isocyanoacetate (4.00 g, 38.35 mmol). This mixture was stirred at RT under N$_2$ atmosphere for 7 h. The solvent was evaporated and the residue was dried overnight under vacuum to give potassium (±)-threo-5-(4-fluorophenyl)-4,5-dihydrooxazole-4-carboxylate ANP 20162 (10.09 g, quantitative yield), as a beige powder. This material was used in the next reaction without further purification.

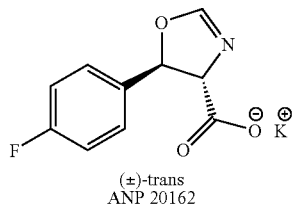

(±)-trans
ANP 20162

MW: 247.26; Yield: Quantitative; Beige powder.

$^1$H-NMR (D$_2$O, δ): 4.42 (dd, 1H, J=7.7 Hz J=1.9 Hz, CHN); 5.53-5.55 (d, 1H, J=7.7 Hz, CHO); 7.15-7.21 (m, 2H, 2×ArH); 7.31 (d, 1H, J=1.8 Hz, CH=N); 7.38-7.43 (m, 2H, 2×ArH).

$^{13}$C-NMR (D$_2$O, δ): 74.2, 81.5, 113.5 (d, 2×C, J=22.1 Hz), 125.7 (d, 2×C, J=8.5 Hz), 133.0 (d, J=249 Hz), 154.8, 160.4 (d, J=249 Hz), 175.5.

MS-ESI m/z (% rel. Int.): 182 (100).

(±)-trans-5-(4-Fluorophenyl)-4,5-dihydrooxazol-4-yl)(4-methylpiperidin-1-yl)methanone, LPO 26074

To a solution of potassium (±)-threo-5-(4-fluorophenyl)-4,5-dihydrooxazole-4-carboxylate, ANP 20162 (500 mg, 2.02 mmol), and triethylamine hydrochloride (278.3 mg, 2.02 mmol) in 50 mL of anhydrous CHCl$_3$ at 4° C., was added HOBT (300.5 mg, 2.22 mmol) and EDCI (426.3 mg, 2.22 mmol). The reaction mixture was stirred at 4° C. for 10 min under nitrogen and 4-methylpiperidine (477.5 µL, 4.04 mmol) was added dropwise. The reaction mixture was stirred at 4° C. to RT for 15 h under nitrogen. The solvent was evaporated and the obtained residue was partitioned between EtOAc (150 mL) and 1N NaOH (50 mL). The organic layer was washed with brine (20 mL), dried over MgSO$_4$, filtered and evaporated to give (±)-trans-5-(4-fluorophenyl)-4,5-dihydrooxazol-4-yl)(4-methylpiperidin-1-yl)methanone, LPO 26074 as a red oil (590 mg, 100% crude yield).

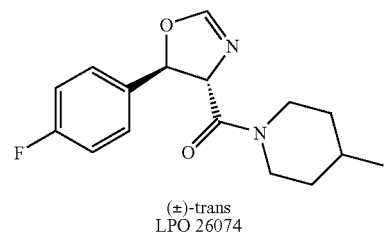

(±)-trans
LPO 26074

MW: 290.33; Yield: 100% crude; Red Oil.

$^1$H-NMR (CDCl$_3$, δ): 0.83-0.98 (m, 4H, 2×CH$_2$), 1.11-1.28 (m, 3H, CH$_3$), 1.56-1.78 (m, 4H, 2×NCH$_2$), 2.31-2.38 (m, 1H, CH), 3.09-3.29 (m, 1H, NCH), 4.99-5.06 (m, 1H, OCH), 6.97-7.11 (m, 2H, 2×ArH), 6.99-7.06 (m, 1H, CH=N), 7.29-7.39 (m, 2H, 2×ArH).

MS-ESI m/z (% rel. Int.): 291.2 ([MH]$^+$, 20), 581.2 (2M+1, 4).

HPLC: Method A, detection UV 210 nm, RT=4.25 min, peak area 70%.

(±)-threo-2-Amino-3-(4-fluorophenyl)-3-hydroxy-1-(4-methylpiperidin-1-yl)propan-1-one hydrochloride, Compound 10

(±)-trans-5-(4-Fluorophenyl)-4,5-dihydrooxazol-4-yl)(4-methylpiperidin-1-yl)methanone, LPO 26074 (590 mg, 2.03 mmol), was dissolved in MeOH (3 mL) and HCl (37%, 1.94 mL, 23.3 mmol) was added slowly. The mixture was stirred at 45° C. for 15 min under nitrogen. The solvent was evaporated and the residue was dried to give a crude yellow solid. The crude product was partitioned between EtOAc (150 mL) and 1M K$_2$CO$_3$ (40 mL). The organic layer was washed with brine (30 mL), dried over MgSO$_4$, filtered and evaporated to give crude (±)-threo-2-amino-3-(4-fluorophenyl)-3-hydroxy-1-(4-methylpiperidin-1-yl)propan-1-one, LPO 26080A, as a yellow oil (300 mg). This crude product was purified by column chromatography (SiO$_2$, eluent CH$_2$Cl$_2$:MeOH=98:2 to 95:5) to give, after evaporation, a white solid (40.7 mg, 0.145 mmol). This white solid was dissolved in MeOH (2 mL) and a 1.56 N HCl solution in MeOH (102 µL, 0.16 mmol) was slowly added. The reaction mixture was stirred at 4° C.

for 10 min. After evaporation and drying, (±)-threo-2-amino-3-(4-fluorophenyl)-3-hydroxy-1-(4-methylpiperidin-1-yl)propan-1-one hydrochloride, Compound 10, was obtained as a white solid (54 mg, 7% yield).

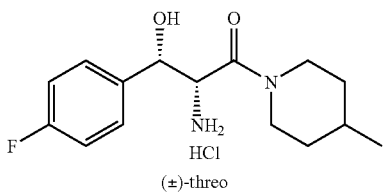

Compound 10
(±)-threo

MW: 316.8; Yield: 7%; White solid, Mp (° C.): 157.7.
$R_f$: 0.25 ($CH_2Cl_2$:MeOH=95:5) free base.
$^1$H-NMR ($CD_3OD$, δ): 0.72-0.89 (m, 3H, $CH_3$), 0.97-1.64 (m, 5H, 0.5×$NCH_2$ & 2×$CCH_2$), 1.86-3.59 (m, 3H, 1.5×$NCH_2$), 4.37-4.44 (m, 2H, NCH & CCH), 4.75-4.83 (m, 1H, OCH), 7.10-7.17 (m, 2H, 2×ArH), 7.39-7.48 (m, 2H, 2×ArH).
MS-ESI m/z (% rel. Int.): 281.3 ([MH]$^+$, 100)
HPLC: Method A, detection UV 254 nm, RT=4.05 min, peak area 96%.

Example 10

Preparation of (±)-threo-2-amino-3-(4-fluorophenyl)-3-hydroxy-1-(4-methoxypiperidin-1-yl)propan-1-one hydrochloride Compound 11

(±)-threo-2-Amino-3-(4-fluorophenyl)-3-hydroxypropanoic acid hydrochloride, LPO 22180

Potassium (±)-threo-5-(4-fluorophenyl)-4,5-dihydrooxazole-4-carboxylate, ANP 20162 (6.00 g, 24.30 mmol), was added to a solution of 6N HCl (150 mL, 0.90 mol) in a 500 mL round bottom flask equipped with a magnetic stirbar. The resulting mixture was stirred 1 h under nitrogen atmosphere at 90° C., and the solvents were evaporated at 65° C. and coevaporated with water (20 mL) to give, after drying, (±)-threo-2-amino-3-(4-fluorophenyl)-3-hydroxypropanoic acid hydrochloride, LPO 22180, (contaminated with KCl) as a white solid (6.5 g, 86% yield). This material was used in the next reaction without further purification.

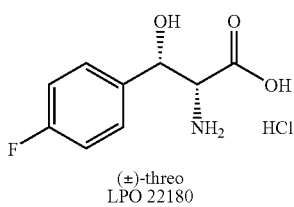

(±)-threo
LPO 22180

MW: 310.19; Yield: 86%; White Solid.
$^1$H-NMR ($D_2O$, δ): 4.19 (d, 1H, J=9.56 Hz, CH); 5.34 (d, 1H, J=7.69 Hz, CH); 7.08-7.14 (m, 2H, 2×ArH); 7.38-7.42 (m, 2H, 2×ArH).
$^{13}$C-NMR ($D_2O$, δ): 56.9, 67.8, 113.5 (d, 2×C, J=21.9 Hz), 125.6 (d, 2×C, J=8.6 Hz), 131.7 (d, 1×C, J=3 Hz), 160.4 (d, 1×C, J=249 Hz), 167.7.
MS-ESI m/z (% rel. Int.): 182 (100), 200.2 ([MH]$^+$, 5).
HPLC: Method A, detection UV 254 nm, RT=0.87 min, peak area <70%.

(±)-threo-2-(tert-Butoxycarbonylamino)-3-(4-fluorophenyl)-3-hydroxypropanoic acid LPO 22182

(±)-threo-2-Amino-3-(4-fluorophenyl)-3-hydroxypropanoic acid hydrochloride, LPO 22180 (6.50 g, 20.25 mmol), was dissolved in a mixture of THF:$H_2O$ (120.0 mL:50.0 mL) in presence of DIEA (11.1 mL, 67.06 mmol) in a 500 mL round bottom flask equipped with a magnetic stirbar. A solution of di-tert-butyl dicarbonate (5.50 g, 25.14 mmol) in THF (70 mL) was added dropwise at 4° C. The mixture was stirred at RT 8 h under nitrogen atmosphere and the solvents were evaporated at 45° C. The residue was dried under vacuum and purified by column chromatography ($SiO_2$, eluent $CH_2Cl_2$:MeOH=95:5 to 92:8) to give, after evaporation and drying, (±)-threo-2-(tert-butoxycarbonylamino)-3-(4-fluorophenyl)-3-hydroxypropanoic acid, LPO 22182 (1.2 g, 26% yield), as a white solid.

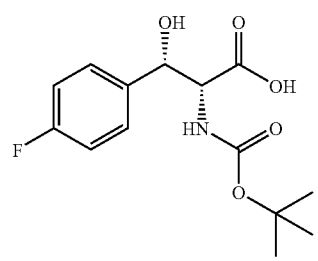

(±)-threo
LPO 22182

MW; 299.29; Yield: 260%; White Solid; Mp (° C.): 122.1.
$R_f$: 0.15 ($CH_2CO_2$:MeOH=95:5).
$^1$H-NMR ($CDCl_3$, δ): 1.15 (s, 3H, 0.33×tBu, minor rotamer), 1.31 (s, 6H, 0.66×tBu, major rotamer), 4.42 (d, 0.33H, J=8.4 Hz, 0.33×CHN, minor rotamer); 4.57 (d, 0.66H, J=7.9 Hz, 0.66×CHN, major rotamer), 5.38 (s, 1H, CHO), 5.53 (d, 0.66H, J=8.9 Hz, 0.66×NH, major rotamer), 6.12 (s broad, 2H, OH), 6.51 (d, 0.33H, J=8.1 Hz, 0.33×NH), 6.99-7.04 (m, 2H, 2×ArH), 7.26-7.34 (m, 2H, 2×ArH).
$^{13}$C-NMR($CDCl_3$, δ): 27.8 (0.66×tBu, major rotamer), 28.1 (0.33×tBu, minor rotamer), 59.2, 72.5, 80.8, 115.2 (d, 2×C, J=22.4 Hz), 127.7 (d, 2×C, J=7.7 Hz), 135.2, 156.2, 162.4 (d, 1×C, J=249 Hz), 174.2.
MS-ESI m/z (% rel. Int.): 621.4 ([2M+23]$^+$, 4), 322.2 ([M+23]$^+$, 6), 300.2 ([MH]$^+$, 3), 136.1 (100).
HPLC: Method A, detection UV 254 nm, RT=4.9 min, peak area 99%.

(±)-threo-tert-Butyl-1-(4-fluorophenyl)-1-hydroxy-3-(4-methoxypiperidin-1-yl)-3-oxopropan-2-ylcarbamate LPO 26092

To a solution of (±)-threo-2-(tert-butoxycarbonylamino)-3-(4-fluorophenyl)-3-hydroxypropanoic acid, LPO 22182 (250 mg, 0.835 mmol), in 10 mL of anhydrous $CH_2Cl_2$ at 4° C. was added HOBT (118.5 mg, 0.877 mmol) and EDCI (168.1 mg, 0.877 mmol). The reaction mixture was stirred at 4° C. for 10 min under nitrogen and 4-methoxypiperidine (217 µL, 1.754 mmol) was added dropwise. The reaction mixture was stirred at 4° C. to RT for 15 h under nitrogen. $CH_2Cl_2$ (80 mL) and water (30 mL) were added. After separation the organic layer was washed with 0.5N NaOH solution (2×20 mL), with brine (20 mL), dried over $MgSO_4$, filtered and evaporated to give (±)-threo-tert-butyl-1-(4-fluorophenyl)-1-hydroxy-3-(4-methoxypiperidin-1-yl)-3-oxopropan-2-ylcarbamate, LPO 26092, as a pale yellow solid (199 mg, 60% yield).

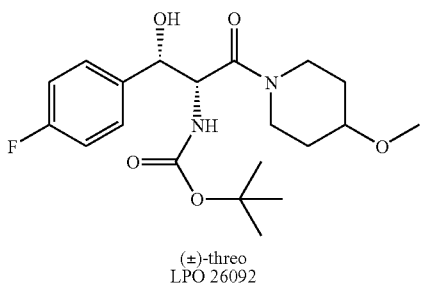

(±)-threo
LPO 26092

MW: 396.45; Yield: 60%; Pale Yellow Solid; Mp (° C.): 166.4.

$^1$H-NMR (CDCl$_3$, δ): 1.30 (s, 9H, 3×CH$_3$), 1.45-1.85 (m, 4H, 2×CCH$_2$), 3.08-4.13 (m, 4H, 2×NCH$_2$), 3.34 (s, 3H, OCH$_3$), 4.68 (s, 1H, NCH), 5.06 (s, 1H, OCH), 6.99-7.04 (m, 2H, 2×ArH), 7.30-7.39 (m, 2H, 2×ArH).

MS-ESI m/z (% rel. Int.): 397.3 ([MH]$^+$, 10), 419.2 (2M+23, 30).

HPLC: Method A, detection UV 210 nm, RT=5.18 min, peak area 97%.

(±)-threo-2-Amino-3-(4-fluorophenyl)-3-hydroxy-1-(4-methoxypiperidin-1-yl)propan-1-one hydrochloride, Compound 11

A solution of (±)-threo-tert-Butyl-1-(4-fluorophenyl)-1-hydroxy-3-(4-methoxypiperidin-1-yl)-3-oxopropan-2-ylcarbamate, LPO 26092 (199 mg, 0.50 mmol), in CH$_2$Cl$_2$ (2.30 mL) and TFA (2.30 mL, 30.12 mmol) was stirred at RT for 15 min. The solvent and TFA were evaporated and the obtained residue was dried to give a yellow solid. This crude product was partitioned between EtOAc (150 mL) and a 1 M K$_2$CO$_3$ aqueous solution (40 mL). After separation the organic layer was washed with brine (20 mL), dried over MgSO$_4$, filtered and evaporated to give LPO 26100B a white oil (140 mg). LPO 26100B (140 mg) was purified by column chromatography (SiO$_2$, eluent CH$_2$Cl$_2$:MeOH=95:5 to 92:8) to give, after evaporation, a white solid (85.5 mg, 0.29 mmol). This solid (85.5 mg, 0.29 mmol) was dissolved in MeOH (2 mL) and a 1.56 N HCl solution in MeOH (203 μL, 0.317 mmol) was slowly added. The reaction mixture was stirred at 4° C. for 10 min. After evaporation of the solvent and drying (±)-threo-2-amino-3-(4-fluorophenyl)-3-hydroxy-1-(4-methoxypiperidin-1-yl)propan-1-one hydrochloride, Compound 11, was obtained as a white solid (87.2 mg, 52% yield).

Compound 11

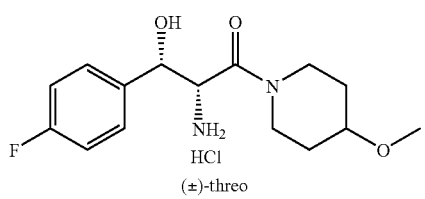

(±)-threo

MW: 332.8; Yield: 52%; White solid; Mp (° C.): 172.3.
R$_f$: 0.25 (CH$_2$Cl$_2$:MeOH=95:5) free base.

$^1$H-NMR (CD$_3$OD, δ): 0.68-1.76 (m, 4H, 2×CCH$_2$), 2.50-3.64 (m, 4H, 2×NCH$_2$), 3.25-3.33 (m, 4H, OCH$_3$ & CCH), 4.51 (d, 1H, J=8.8 Hz, NCH), 4.83 (d, 1H, J=8.8 Hz, OCH), 7.12-7.17 (m, 2H, 2×ArH), 7.43-7.48 (m, 2H, 2×ArH).

MS-ESI m/z (% rel. Int.): 297.3 ([MH]$^+$, 50).

HPLC: Method A, detection UV 210 nm, RT=3.68 min, peak area 97%.

Example 11

Preparation of (±)-threo-2-amino-1-(azepan-1-yl)-3-(4-fluorophenyl)-3-hydroxypropan-1-one hydrochloride. Compound 12 tert-Butyl (±)-threo 1-(azepan-1-yl)-3-(4-fluorophenyl)-3-hydroxy-1-oxopropan-2-yl-carbamate To a solution of (±)-threo-2-(tert-butoxycarbonylamino)-3-(4-fluorophenyl)-3-hydroxypropanoic acid, LPO 22182 (800 mg, 2.67 mmol), and hexamethyleneimine (298 mg, 2.94 mmol) in 20 mL of anhydrous DMF was added N,N-diisopropylethylamine (992 μL, 5.88 mmol), HOBT (459 mg, 2.94 mmol) and EDCI (627 mg, 3.21 mmol). After overnight stirring at RT, EtOAc was added to the reaction mixture and the solution was washed successively with a 5% NaHCO$_3$ solution, a saturated NH$_4$Cl solution and brine. The organic layer was dried over Na$_2$SO$_4$, filtered and evaporated. The residue was purified by column chromatography (SiO$_2$, eluent CH$_2$Cl$_2$:MeOH=99:1 to 98:2) to give, after evaporation, tert-butyl (±)-threo-1-(azepan-1-yl)-3-(4-fluorophenyl)-3-hydroxy-1-oxopropan-2-yl-carbamate as a yellow oil (954 mg, 94% yield).

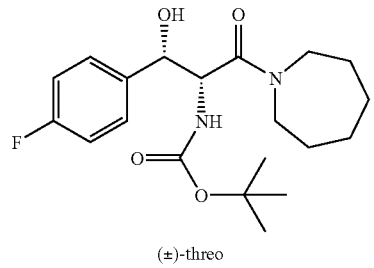

(±)-threo

MW: 380.45; Yield: 940%; Yellow Oil.

$^1$H-NMR (CDCl$_3$, δ): 1.31 (s, 9H, 3×CH$_3$), 1.34-1.76 (m, 8H, 4×CH$_2$), 3.46 (m, 4H, 2×NCH$_2$), 4.66 (m, 1H, NCH), 4.84 (br s, 1H, OH), 5.02 (d, 1H, J=3.3 Hz, OCH), 5.60 (d, 1H, J=9.9 Hz, NH), 6.96-7.06 (m, 2H, 2×ArH), 7.33-7.40 (m, 2H, 2×ArH)

MS-ESI m/z (% rel. Int.): 325.2 ([M-tBu+H]$^+$, 85), 381.2 ([MH]$^+$, 100).

HPLC: Method C, detection UV 205 nm, RT=21.71 min, peak area 98.0%.

(±)-threo-2-Amino-1-(azepan-1-yl)-3-(4-fluorophenyl)-3-hydroxypropan-1-one hydrochloride, Compound 12

A solution of tert-Butyl (±)-threo-1-(azepan-1-yl)-3-(4-fluorophenyl)-3-hydroxy-1-oxopropan-2-yl-carbamate (944 mg, 2.48 mmol) in CH$_2$Cl$_2$ (6 mL) and TFA (6 mL) was stirred at RT for 1 h. The solvent and TFA were evaporated and the obtained residue was dried to give a white solid. This crude product was partitioned between EtOAc and a saturated NaHCO₃ aqueous solution. The organic layer was washed with brine, dried over Na₂SO₄, filtered and evaporated. The residue was purified by column chromatography (SiO₂, eluent CH₂Cl₂:MeOH=99:1 to 90:10) to give, after evaporation, a white solid (220 mg, 0.78 mmol). This solid was dissolved in MeOH (5 mL) and a 2 N HCl solution in Et₂O (780 μL, 1.60 mmol) was slowly added. The reaction mixture was stirred at RT for 10 min. After evaporation of the solvent and drying, (±)-threo-2-amino-1-(azepan-1-yl)-3-(4-fluorophenyl)-3-hydroxypropan-1-one hydrochloride, Compound 12, was obtained as a beige solid (233 mg, 33% yield).

Compound 12

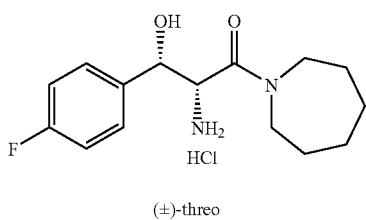

(±)-threo

MW: 316.80; Yield: 33%; Beige Solid; Mp (° C.): 167.2.

R_f: 0.38 (CH₂Cl₂:MeOH=90:10) free base.

¹H-NMR (CD₃OD, δ): 1.09-1.13 (m, 8H, 4×CH₂), 2.70 (m, 1H, 0.5×NCH₂), 3.13-3.27 (m, 2H, NCH₂), 3.52 (m, 1H, 0.5×NCH₂), 4.39 (d, 1H, J=9.0 Hz, NCH), 4.88 (d partially masked by water broad peak at 4.89 ppm, 1H, OCH), 7.09-7.17 (m, 2H, 2×ArH), 7.43-7.50 (m, 2H, 2×ArH).

MS-ESI m/z (% rel. Int.): 281.3 ([MH]⁺, 100).

HPLC: Method C, detection UV 207 nm, RT=14.06 min, peak area 99.6%.

Example 12

Preparation of (±)-threo-2-amino-1-(3,3-difluoropyrrolidin-1-yl)-3-(4-fluorophenyl)-3-hydroxypropan-1-one hydrochloride, Compound 13 tert-Butyl (±)-threo-1-(3,3-difluoropyrrolidin-1-yl)-3-(4-fluorophenyl)-3-hydroxy-1-oxopropan-2-ylcarbamate To a solution of (±)-threo-2-(tert-butoxycarbonylamino)-3-(4-fluorophenyl)-3-hydroxypropanoic acid, LPO 22182 (800 mg, 2.67 mmol), and 3,3-difluoropyrrolidine hydrochloride (422 mg, 2.94 mmol) in 20 mL of anhydrous DMF was added N,N-diisopropylethylamine (1.80 mL, 10.7 mmol), HOBT (459 mg, 2.94 mmol) and EDCI (627 mg, 3.21 mmol). After overnight stirring at PT, EtOAc was added to the reaction mixture and the solution was washed successively with a 5% NaHCO₃ solution, a saturated NH₄Cl solution and brine. The organic layer was dried over Na₂SO₄, filtered and evaporated to afford tert-butyl (±)-threo-1-(3,3-difluoropyrrolidin-1-yl)-3-(4-fluorophenyl)-3-hydroxy-1-oxopropan-2-ylcarbamate as pale yellow solid (1.02 g, 89%).

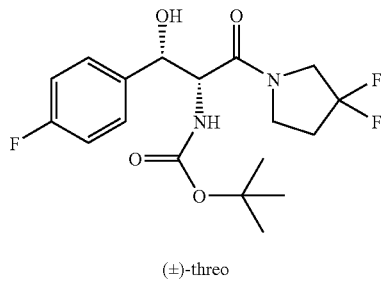

(±)-threo

MW: 388.38; Yield: 89%; Yellow Solid.

¹H-NMR (CDCl₃, δ): 1.34 (s, 9H, 3×CH₃), 2.15-2.40 (m, 2H, CH₂), 3.30-3.94 (m, 4H, 2×NCH₂), 4.35-4.54 (m, 2H, OH and NCH), 5.02 (m, 1H, OCH), 5.64 (m, 1H, NH), 6.98-7.07 (m, 2H, 2×ArH), 7.33-7.39 (m, 2H, 2×ArH).

MS-ESI m/z (% rel. Int.): 333.1 ([M-tBu+H]⁺, 100), 389.2 ([MH]⁺, 50).

HPLC: Method C, detection UV 205 nm, RT=20.28 min, peak area 98.6%.

(±)-threo-2-Amino-1-(3,3-difluoropyrrolidin-1-yl)-3-(4-fluorophenyl)-3-hydroxypropan-1-one hydrochloride, Compound 13

A solution of tert-butyl (±)-threo-1-(3,3-difluoropyrrolidin-1-yl)-3-(4-fluorophenyl)-3-hydroxy-1-oxopropan-2-ylcarbamate (1.02 g, 2.63 mmol) in CH₂Cl₂ (7 mL) and TFA (6 mL) was stirred at RT for 1 h. The solvent and TFA were evaporated and the obtained residue was dried. This crude product was partitioned between EtOAc and a saturated NaHCO₃ aqueous solution. The organic layer was washed with brine, dried over Na₂SO₄, filtered and evaporated to give a beige solid. This solid was purified by column chromatography (SiO₂, eluent CH₂Cl₂:MeOH=99:1 to 90:10) to give, after evaporation, a white solid (550 mg, 1.90 mmol). This solid (522 mg, 1.81 mmol) was dissolved in MeOH (6 mL) and a 2 N HCl solution in Et₂O (1.80 mL, 3.60 mmol) was slowly added. The reaction mixture was stirred at RT for 10 min. After evaporation of the solvent and drying, (±)-threo-2-amino-1-(3,3-difluoropyrrolidin-1-yl)-3-(4-fluorophenyl)-3-hydroxypropan-1-one hydrochloride, Compound 13, was obtained as a beige solid (566 mg, 66% yield).

Compound 13

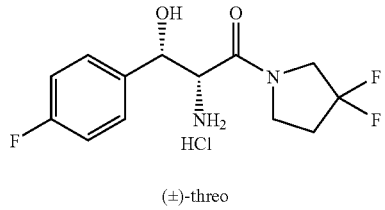

(±)-threo

MW: 324.73; Yield: 66%; Beige Solid; Mp (° C.): 174.3.

R_f: 0.38 (CH₂Cl₂:MeOH=90:10) free base.

¹H-NMR (CD₃OD, δ): 1.43-2.57 (m, 2.8H), 2.82-2.96 (m, 0.2H), 3.39-3.97 (m, 3H), 4.14 (d, 0.5H, J=9.3 Hz, 0.5×NCH), 4.26 (d, 0.5H, J=8.7 Hz, 0.5×NCH), 4.62 (d, 0.1H, J=8.4 Hz, 0.1×OCH), 4.72 (d, 0.2H, J=8.7 Hz, 0.2×OCH), 5.02-5.15 (m, 0.5H, 0.5×OCH), 5.38 (m, 0.2H, 0.2×OCH), 7.13-7.30 (m, 2H, 2×ArH), 7.46-7.57 (m, 1.7H, 1.7×ArH), 7.65-7.71 (m, 0.3H, 0.3×ArH)

MS-ESI m/z (% rel. Int.): 289.3 ([MH]⁺, 100).
HPLC: Method C, detection UV 206 nm, RT=12.94 min, peak area 97.3%.

Example 13

Preparation of (2R,3S)-2-amino-3-(4-fluorophenyl)-1-((S)-3-fluoropyrrolidin-1-yl)-3-hydroxypropan-1-one hydrochloride and (2S,3R)-2-amino-3-(4-fluorophenyl)-1-((S)-3-fluoropyrrolidin-1-yl)-3-hydroxypropan-1-one hydrochloride (as a 1:1 mixture), Compound 14 tert-Butyl (1R,2S)-1-(4-fluorophenyl)-3-((S)-3-fluoropyrrolidin-1-yl)-1-hydroxy-3-oxopropan-2-ylcarbamate and tert-butyl (1S,2R)-1-(4-fluorophenyl)-3-((S)-3-fluoropyrrolidin-1-yl)-1-hydroxy-3-oxopropan-2-ylcarbamate (1:1)

To a solution of (±)-threo-2-(tert-butoxycarbonylamino)-3-(4-fluorophenyl)-3-hydroxypropanoic acid, LPO 22182 (1.0 g, 3.30 mmol) and (S)-3-fluoropyrrolidine hydrochloride (462 mg, 3.68 mmol) in 20 mL of anhydrous DMF was added N,N-diisopropylethylamine (1.80 mL, 10.7 mmol), HOBT (574 mg, 3.68 mmol) and EDCI (784 mg, 4.01 mmol). After overnight stirring at RT, EtOAc was added to the reaction mixture and the solution was washed successively with a 5% NaHCO₃ solution, a saturated NH₄Cl solution and brine. The organic layer was dried over Na₂SO₄, filtered and evaporated to give a 1:1 mixture of tert-butyl (1R,2S)-1-(4-fluorophenyl)-3-((S)-3-fluoropyrrolidin-1-yl)-1-hydroxy-3-oxopropan-2-ylcarbamate and tert-butyl (1S,2R)-1-(4-fluorophenyl)-3-((S)-3-fluoropyrrolidin-1-yl)-1-hydroxy-3-oxopropan-2-ylcarbamate as a yellow solid (602 mg, 49% yield).

(2R,3S)-2-Amino-3-(4-fluorophenyl)-1-((S)-3-fluoropyrrolidin-1-yl)-3-hydroxypropan-1-one hydrochloride and (2S,3R)-2-amino-3-(4-fluorophenyl)-1-((S)-3-fluoropyrrolidin-1-yl)-3-hydroxypropan-1-one hydrochloride (1:1), Compound 14

A solution of tert-Butyl (1R,2S)-1-(4-fluorophenyl)-3-((S)-3-fluoropyrrolidin-1-yl)-1-hydroxy-3-oxopropan-2-ylcarbamate and tert-butyl (1S,2R)-1-(4-fluorophenyl)-3-((S)-3-fluoropyrrolidin-1-yl)-1-hydroxy-3-oxopropan-2-ylcarbamate (1:1) (602 mg, 1.62 mmol) in CH₂Cl₂ (4 mL) and TFA (3 mL) was stirred at RT for 1 h. The solvent and TFA were evaporated and the obtained residue was dried to give a brown solid. This crude product was partitioned between EtOAc and a saturated NaHCO₃ aqueous solution. The organic layer was washed with brine, dried over Na₂SO₄, filtered and evaporated. The residue was purified by column chromatography (SiO₂, eluent CH₂Cl₂:MeOH=99:1 to 90:10) to give, after evaporation, an orange solid (296 mg, 1.09 mmol). This solid (276 mg, 0.78 mmol) was dissolved in MeOH (3 mL) and a 2 N HCl solution in Et₂O (1.0 mL, 2.0 mmol) was slowly added. The reaction mixture was stirred at PT for 10 min. After evaporation of the solvent and drying, a 1:1 mixture of (2R,3S)-2-amino-3-(4-fluorophenyl)-1-((S)-3-fluoropyrrolidin-1-yl)-3-hydroxypropan-1-one hydrochloride and (2S,3R)-2-amino-3-(4-fluorophenyl)-1-((S)-3-fluoropyrrolidin-1-yl)-3-hydroxypropan-1-one hydrochloride, Compound 14, was obtained as a beige solid (305 mg, 61% yield).

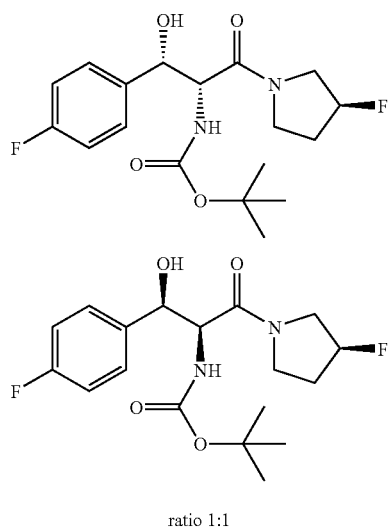

ratio 1:1

MW: 370.39; Yield: 49%; Yellow Solid.

¹H-NMR (CDCl₃, δ): 1.32 (s, 9H, 3×CH₃), 1.65-2.34 (m, 3H, 1.5×CH₂), 3.10-3.96 (m, 3H, 1.5×CH₂), 4.35-4.59 (m, 0.5H, 0.5×NCH), 5.02 (m, 0.5H, 0.5×NCH), 5.06-5.10 (m, 1H, OCH), 5.24-5.34 (m, 0.5H, 0.5×CHF), 5.42-5.56 (m, 0.5H, 0.5×CHF), 6.97-7.07 (m, 2H, 2×ArH), 7.33-7.41 (m, 2H, 2×ArH).

MS-ESI m/z (% rel. Int.): 315.1 ([M-tBu+H]⁺, 100), 371.2 ([MH]⁺, 72).

Compound 14

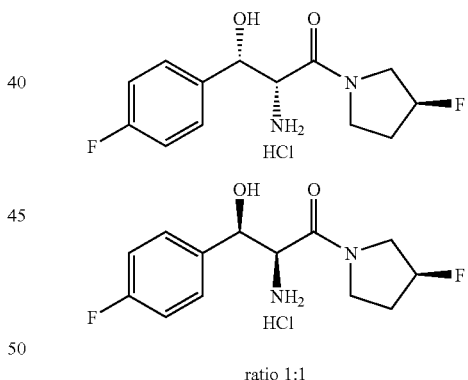

ratio 1:1

MW: 306.74; Yield: 61%; Beige Solid; Mp (° C.): 182.4.

R_f: 0.38 (CH₂Cl₂:MeOH=90:10) free base.

¹H-NMR (CD₃OD, δ): 1.33-2.39 (m, 2.5H, 2.5×CH₂), 2.55-2.69 (m, 0.5H, 0.5×CH₂), 3.13-3.85 (m, 3H, 1.5×CH₂), 4.10 (d, 0.2H, J=9.3 Hz, 0.2×NCH), 4.17-4.25 (m, 0.8H, 0.8×NCH), 4.82 (d partially masked by water broad peak at 4.89 ppm, 1H, OCH), 4.97 (m, 0.2H, 0.2×CHF), 5.07 (m, 0.3H, 0.3×CHF), 5.14 (m, 0.2H, 0.2×CHF), 5.24 (m, 0.3H, 0.3×CHF), 7.08-7.21 (m, 2H, 2×ArH), 7.43-7.53 (m, 2H, 2×ArH).

MS-ESI m/z (% rel. Int.): 271.3 ([MH]⁺, 100).
HPLC: Method C, detection UV 205 nm, RT=11.75 min, peak area 97.2%.

Example 14

Preparation of (±)-threo-2-(benzylamino)-3-(4-fluorophenyl)-3-hydroxy-1-(pyrrolidin-1-yl)propan-1-one hydrochloride, Compound 15

To a solution (±)-threo-2-amino-3-(4-fluorophenyl)-3-hydroxy-1-(pyrrolidin-1-yl)propan-1-one (free base of Compound 1, 220 mg, 0.872 mmol) in $CH_2Cl_2$ (5 mL) was added benzaldehyde (97.5 µL, 0.959 mmol). The reaction mixture was stirred under nitrogen at RT for 5 min and acetic acid (60.1 µL, 1.744 mmol) and sodium cyanoborohydride (60-3 mg, 0.959 mmol) were slowly added. The mixture was stirred at RT under nitrogen atmosphere for 6.5 h. The solvent was evaporated and the residue was partitioned between EtOAc (250 mL) and a 1 M $K_2CO_3$ aqueous solution (60 mL). The organic layer was washed with brine (30 mL), dried over $MgSO_4$, filtered and evaporated to give a colourless oily product (310 mg). This crude product was purified by column chromatography ($SiO_2$, eluent $CH_2Cl_2$:EtOAc=9:1 to 6:4) to give, after evaporation and drying, (±)-threo-2-(benzylamino)-3-(4-fluorophenyl)-3-hydroxy-1-(pyrrolidin-1-yl)propan-1-one, LPO 22054A (152 mg, 50% yield). LPO 22054A (152 mg, 0.44 mmol) was dissolved in MeOH (4 mL) and a 0.65 N HCl solution in MeOH (752.2 µL, 0.49 mmol) was slowly added. The reaction mixture was stirred at 4° C. for 10 min. After evaporation and drying, (±)-threo-2-(benzylamino)-3-(4-fluorophenyl)-3-hydroxy-1-(pyrrolidin-1-yl)propan-1-one hydrochloride, Compound 15, was obtained as a white solid (157.3 mg, 48% yield).

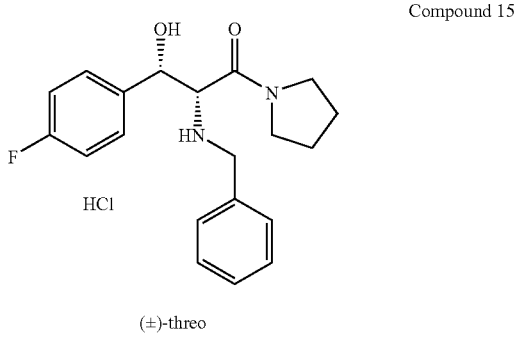

Compound 15

(±)-threo

MW: 378.87; Yield: 48%; White Solid; Mp (° C.): 204.3.
$R_f$: 0.25 ($CH_2Cl_2$:EtOAc=6:4) free base.
$^1$H-NMR ($CD_3OD$, δ): 1.23-1.29 (m, 2H, $CH_2$), 1.41-1.65 (m, 2H, $CH_2$), 1.79-1.86 (m, 1H, 0.5×$NCH_2$), 2.57-2.64 (m, 1H, 0.5×$NCH_2$), 3.06-3.18 (m, 2H, $NCH_2$), 3.91 (d, 1H, J=9.5 Hz, NCH), 4.25 (s, 2H, $NHCH_2$), 4.85-4.89 (m, 1H, OCH), 7.08-7.13 (m, 2H, 2×ArH), 7.38-7.46 (m, 7H, 7×ArH).
$^{13}$C-NMR ($CD_3OD$, δ): 24.6, 26.3, 47.1, 47.3, 51.2, 65.3, 73.8, 116.4 (d, 2×C J=22 Hz), 129.8 (d, 2×C, J=8 Hz), 130.2 (2×C), 130.7, 131.3 (2×C), 132.2, 136.5, 164.5 (d, J=249.0 Hz), 165.3.
MS-ESI m/z (% rel. Int.): 343.2 ([MH]$^+$, 100), 365.2 (M+23, 6).
HPLC: Method A, detection UV 210, RT=4.75 min, peak area 98%.

Example 15

Preparation of (±)-threo-2-(3,4-dichlorobenzylamino)-3-(4-fluorophenyl)-3-hydroxy-1-(pyrrolidin-1-yl)propan-1-one hydrochloride, Compound 16

To a solution (±)-threo-2-amino-3-(4-fluorophenyl)-3-hydroxy-1-(pyrrolidin-1-yl)propan-1-one (free base of Compound 1, 200 mg, 0.79 mmol) in $CH_2Cl_2$ (6 mL) was added 3,4-dichlorobenzaldehyde (145.5 mg, 0.83 mmol). The solution was stirred under nitrogen at RT for 5 min then acetic acid (79.3 µL, 1.38 mmol) and sodium cyanoborohydride (52.2 mg, 0.83 mmol) were added slowly. The reaction mixture was stirred at RT under nitrogen atmosphere for 15 h. After evaporation, the residue was partitioned between EtOAc (250 mL) and a 1 M $K_2CO_3$ aqueous solution (60 mL). The organic layer was washed with brine (30 mL), dried over $MgSO_4$, filtered and the solvent was evaporated to give a white solid (230 mg). This crude compound was purified by column chromatography ($SiO_2$, eluent $CH_2Cl_2$:EtOAc=8:2) to give, after evaporation and drying, (±)-threo-2-(3,4-dichlorobenzylamino)-3-(4-fluorophenyl)-3-hydroxy-1-(pyrrolidin-1-yl)propan-1-one, LPO 22042A (93 mg, 37% yield). LPO 22042A (93 mg, 0.23 mmol) was dissolved in MeOH (3 mL), and a 0.65 N HCl solution in MeOH (417 µL, 0.271 mmol) was slowly added. The reaction mixture was stirred at 4° C. for 10 min. After evaporation and drying, (±)-threo-2-(3,4-dichlorobenzylamino)-3-(4-fluorophenyl)-3-hydroxy-1-(pyrrolidin-1-yl)propan-1-one hydrochloride, Compound 16, was obtained as a white solid (91.5 mg, 29% yield).

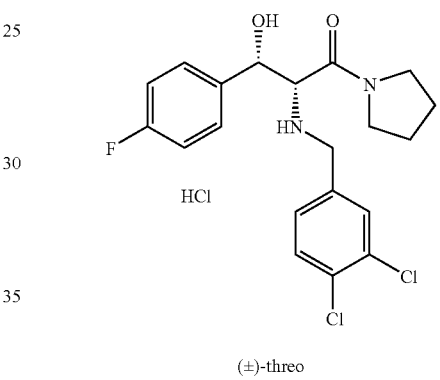

Compound 16

(±)-threo

MW: 447.76; Yield: 29%; White Solid; Mp (° C.): 216.0.
$R_f$: 0.25 ($CH_2Cl_2$:EtOAc=6:4) free base.
$^1$H-NMR ($CD_3OD$, δ): 1.32-1.67 (m, 4H, 2×$CH_2$), 1.87-1.92 (m, 1H, 0.5×$NCH_2$), 2.84-2.90 (m, 1H, 0.5×$NCH_2$), 3.09-3.15 (m, 2H, $NCH_2$), 4.10 (d, 1H, J=9.5 Hz, N—CH), 4.11-4.36 (m, 2H, $NHCH_2$), 4.80 (m, 1H, OCH), 7.12 (t, 2H, J=8.7 Hz, 2×ArH), 7.40-7.46 (m, 3H, 3×ArH), 7.61 (d, 1H, J=8.3 Hz, ArH), 7.70 (s, 1H, ArH).
$^{13}$C-NMR ($CD_3OD$, δ): 24.6, 26.4, 47.2, 47.5, 50.1, 65.7, 73.6, 116.3, 116.6, 129.7, 129.8, 131.5, 132.2, 132.3, 133.7, 133.8, 135.0, 136.2, 163.6 (d, J=246.9 Hz), 164.7.
MS-ESI m/z (% rel. Int.): 411.1 ([MH]$^+$, 100), 433.1 (M+23, 8).
HPLC: Method A, detection UV 210 nm, RT=4.85 min, peak area 98%.

Example 16

Preparation of (1S,2R)-2-amino-1-(4-fluorophenyl)-3-oxo-3-(pyrrolidin-1-yl)propyl acetate hydrochloride Compound 17 tert-Butyl (1S,2R)-1-(4-fluorophenyl)-1-hydroxy-3-oxo-3-(pyrrolidin-1-yl)propan-2-ylcarbamate, CCH 23140-1

To a solution of (−)-threo-2-amino-3-(4-fluorophenyl)-3-hydroxy-1-(pyrrolidin-1-yl)propan-1-one hydrochloride, Compound 3 (375 mg, 1.30 mmol), in dry $CH_2Cl_2$ (17 mL) in a 50 mL round-bottomed flask equipped with a magnetic stirbar was added successively $NEt_3$ (0.43 mL, 3.09 mmol), DMAP (15 mg, 123 µmol) and di-tert-butyl dicarbonate (312 mg, 1.43 mmol). The reaction mixture was stirred overnight at RT, washed with 10% citric acid aqueous solution (5 mL), brine (5 mL), dried over $Na_2SO_4$, filtered and concentrated at 35° C. under vacuum. Purification by column chromatography ($SiO_2$, eluent $CH_2Cl_2$:MeOH=98:2) afforded, after evaporation and drying, tert-butyl (1S,2R)-1-(4-fluorophenyl)-1-hydroxy-3-oxo-3-(pyrrolidin-1-yl)propan-2-ylcarbamate, CCH 23140-1, as a white solid (434 mg, 95% yield).

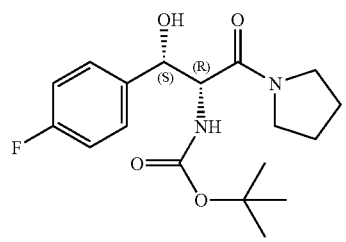

CCH 23140-1

MW: 352.40; Yield: 95%; White Solid; Mp (° C.): 125.5.
$\alpha^{22}_D$=–13.8 (MeOH, c=1).
$R_f$: 0.35 ($CH_2Cl_2$: MeOH=97:3).
$^1$H-NMR ($CDCl_3$, δ): 1.33 (s, 9H, 3×$CH_3$), 1.80-1.89 (m, 4H, 2×$CH_2$), 3.07-3.53 (m, 4H, 2×$NCH_2$), 4.50 (d, 1H, J=6.9 Hz, OH), 4.59 (d, 1H, J=1.6 Hz, NCH), 5.02 (d, 1H, J=1.6 Hz, OCH), 5.53 (d, 1H, NH, J=8.3 Hz), 6.99-7.05 (m, 2H, 2×ArH), 7.35-7.40 (m, 2H, 2×ArH).
MS-ESI m/z (% rel. Int.): 253.2 (100), 353.2 ([MH]$^+$, 5), 375.2 ([M+23]$^+$, 20).
HPLC: Method A, detection UV 254 nm, RT=5.1 min, peak area 97%.

(1S,2R)-2-(tert-Butoxycarbonylamino)-1-(4-fluorophenyl)-3-oxo-3-(pyrrolidin-1-yl)propyl acetate, CCH 23140-2

To a solution of tert-butyl (1S,2R)-1-(4-fluorophenyl)-1-hydroxy-3-oxo-3-(pyrrolidin-1-yl)propan-2-ylcarbamate, CCH 23140-1 (434 mg, 1.23 mmol), in dry $CH_2Cl_2$ (15 mL) at 0° C. in a 50 mL round-bottomed flask equipped with a magnetic stirbar was added successively diisopropylaminomethyl-polystyrene resin (1.0 g, 3.0 mmol), DMAP (15 mg, 123 µmol) and acetic anhydride (130 µL, 1.38 mmol). The reaction mixture was stirred overnight at RT, then filtered through cotton wool, washed with brine (5 mL), dried over $Na_2SO_4$, filtered and concentrated at 35° C. under vacuum. Purification by column chromatography ($SiO_2$, eluent cyclohexane:EtOAc=3:2) afforded, after evaporation and drying, (1S,2R)-2-(tert-butoxycarbonylamino)-1-(4-fluorophenyl)-3-oxo-3-(pyrrolidin-1-yl)propyl acetate, CCH 23140-2, as a colorless oil (338 mg, 70% yield).

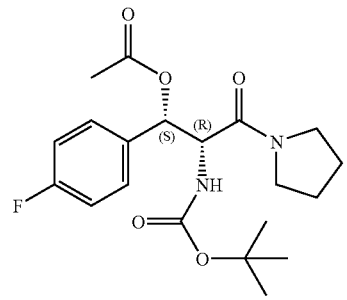

CCH 23140-2

MW: 394.44; Yield: 70%; Colorless Oil.
$R_f$: 0.2 (cyclohexane:EtOAc=3:2).
$^1$H-NMR ($CDCl_3$, δ): 1.41 (s, 9H, $C(CH_3)_3$), 1.623-1.90 (m, 4H, 2×$CH_2$), 2.12 (s, 3H, $CH_3$), 2.82-2.89 (m, 1H, 0.5×$NCH_2$), 3.14-3.22 (m, 1H, 0.5×$NCH_2$), 3.34-3.52 (m, 2H, $NCH_2$), 4.74 (dd, 1H, J=8.1 and 9.5 Hz, NHCH, 5.50 (d, 1H, J=9.5 Hz, NHCH), 6.01 (d, 1H, J=8.1 Hz, OCH), 6.99-7.05 (m, 2H, 2×ArH), 7.30-7.40 (m, 2H, 2×ArH).
$^{13}$C-NMR ($CDCl_3$, δ): 20.9 ($CH_3$), 23.9 ($CH_2$), 25.7 ($CH_2$), 28.2 ($C(CH_3)_3$), 45.7 ($CH_2$), 46.4 ($CH_2$), 56.7 (CH), 74.7 (CH), 79.8 ($C(CH_3)_3$), 115.2 (d, J=21.6 Hz, 2×CH), 128.7 (d, J=8.2 Hz, 2×CH), 132.4 (d, J=3.0 Hz, C), 155.2 (CO), 163.3 (d, J=247.5 Hz, CF), 167.2 (C=O), 169.9 (C=O).

(1S,2R)-2-Amino-1-(4-fluorophenyl)-3-oxo-3-(pyrrolidin-1-yl)propyl acetate hydrochloride, Compound 17

A solution of (1S,2R)-2-(tert-butoxycarbonylamino)-1-(4-fluorophenyl)-3-oxo-3-(pyrrolidin-1-yl)propyl acetate, CCH 23140-2 (104 mg, 264 µmol), in $Et_2O$ (20 mL) in a 100 mL round-bottomed flask equipped with a magnetic stirbar was stirred for 1 h at RT in presence of a stream of HCl. The reaction mixture was concentrated and dried for 3 days under vacuum to obtain (1S,2R)-2-amino-1-(4-fluorophenyl)-3-oxo-3-(pyrrolidin-1-yl)propyl acetate hydrochloride, Compound 17, as a white solid (86 mg, 98% yield).

Compound 17

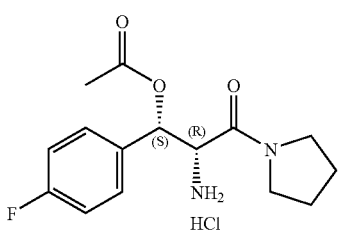

MW: 330.78; Yield: 98%; White Solid; Mp (° C.): 146.0.
$\alpha^{22}_D$=–17.7 (MeOH, c=1).
$^1$H-NMR ($CD_3OD$, δ): 1.41-1.70 (m, 4H, 2×$CH_2$), 2.10 (s, 3H, $CH_3$), 2.37-2.45 (m, 1H, 0.5×$NCH_2$), 3.04-3.37 (m, 3H, 1.5×$CH_2$), 4.49 (d, 1H, J=9.1 Hz, NCH), 5.85 (d, 1H, J=9.1 Hz, OCH), 7.06-7.12 (m, 2H, 2×ArH), 7.34-7.39 (m, 2H, 2×ArH).
$^{13}$C-NMR ($CD_3OD$, δ): 20.8 ($CH_3$), 24.8 ($CH_2$), 26.6 ($CH_2$), 47.4 ($CH_2$), 47.9 ($CH_2$), 56.7 (CH), 75.0 (CH), 116.9 (d, J=22.2 Hz, 2×CH), 130.1 (d, J=8.5 Hz, 2×CH), 132.3 (d, J=3.2 Hz, C), 164.7 (d, J=247.8 Hz, CF), 165.1 (CO), 170.8 (CO).

MS-ESI m/z (rel. int.): 98 (100), 277 (32), 295 ([M+H]+, 8), 317 ([M+Na]+, 12).

HPLC: Method A, detection UV 254 nm, RT=3.76 min, peak area 95.7%.

Example 17

Preparation of (±)-threo-2-amino-3-(4-fluorophenyl)-3-hydroxy-N-methoxy-N-methylpropanamide hydrochloride, Compound 18

(±)-threo-tert-Butyl-1-(4-fluorophenyl)-1-hydroxy-3-(methoxy(methyl)amino)-3-oxopropan-2-ylcarbamate TTA 24064

To a solution of (±)-threo-2-(tert-butoxycarbonylamino)-3-(4-fluorophenyl)-3-hydroxypropanoic acid, LPO 22182 (300 mg, 1.00 mmol), in 18 mL of anhydrous CH$_2$Cl$_2$ was added at 4° C. DIEA (435 μL, 1.754 mmol), HOBT (176 mg, 1.30 mmol) and EDCI (250 mg, 1.30 mmol). The reaction mixture was stirred for 10 min at 4° C. under nitrogen atmosphere and N,O-dimethylhydroxylamine hydrochloride (128 mg, 1.3 mmol) was added portionwise. After stirring for 15 h at 4° C. to RT, CH$_2$Cl$_2$ (80 mL) and water (30 mL) were added. The organic layer was washed with a 0.5N NaOH (2×20 mL) solution, brine, dried over MgSO$_4$, filtered and evaporated to give (±)-threo-tert-butyl-1-(4-fluorophenyl)-1-hydroxy-3-(methoxy(methyl)amino)-3-oxopropan-2-ylcarbamate, TTA 24064, as a pale yellow solid (340 mg, 99% yield).

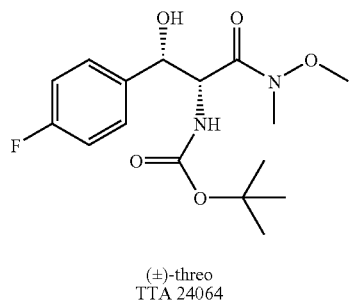

(±)-threo
TTA 24064

MW: 342.16; Yield 99%, Pale Yellow Solid.

$^1$H-NMR (CDCl$_3$, δ): 1.33 (s, 9H, 3×CH$_3$), 3.20 (s, 3H, NCH$_3$), 3.72 (s, 3H, NCH$_3$), 3.34 (s, 3H, OCH$_3$), 4.93 (d, 1H, J=7.1 Hz, NCH), 5.02 (d, 1H, J=2.8 Hz, OCH), 5.47 (d, 1H, J=8.1 Hz, NH), 7.00-7.07 (m, 2H, 2×ArH), 7.33-7.40 (m, 2H, 2×ArH).

MS-ESI m/z (% rel. Int.): 243.2 ([MH-Boc]+, 40), 365.2 (M+23, 30).

HPLC: Method A, detection UV 210 nm, RT=5.24 min, peak area 95%. (±)-threo-2-Amino-3-(4-fluorophenyl)-3-hydroxy-N-methoxy-N-methyl propanamide hydrochloride, Compound 18

A solution of (±)-threo-tert-butyl-1-(4-fluorophenyl)-1-hydroxy-3-(methoxy(methyl)amino)-3-oxopropan-2-ylcarbamate, TTA 24064 (250 mg, 0.73 mmol), in CH$_2$Cl$_2$ (5 mL) and TFA (1 mL, 13 mmol) was stirred at RT for 15 min. The solvent and TFA were evaporated and the residue was dried to give a yellow solid. This crude product was partitioned between CH$_2$Cl$_2$ (80 mL) and a 1 M K$_2$CO$_3$ solution (30 mL). The organic layer was washed with brine, dried over MgSO$_4$, filtered and evaporated to give an oil (160 mg). that the crude oil was purified by column chromatography (SiO$_2$, eluent EtOAc to EtOAc:MeOH=9:1) to give, after evaporation and drying, (±)-threo-2-amino-3-(4-fluorophenyl)-3-hydroxy-N-methoxy-N-methylpropanamide, TTA 24068 (88 mg, 50% yield). Compound TTA 24068 (88 mg, 0.36 mmol) was dissolved in MeOH (3 mL) and a 0.2 N HCl solution in MeOH (3 mL, 0.39 mmol) was slowly added. The reaction mixture was stirred at 4° C. for 10 min. After evaporation of the solvent and drying, (±)-threo-2-amino-3-(4-fluorophenyl)-3-hydroxy-N-methoxy-N-methylpropanamide hydrochloride, Compound 18, was obtained as a white solid (95 mg, 47% yield).

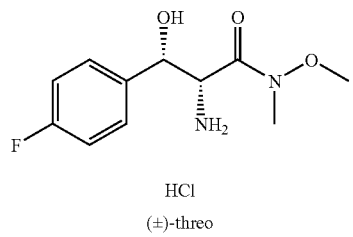

Compound 18

(±)-threo

MW: 278.71; Yield: 47%; White Solid, Mp (° C.): 148.1.
R$_f$: 0.20 (EtOAc:MeOH=9:1) free base.

$^1$H-NMR (CD$_3$OD, δ): 3.12 (s, 3H, NCH$_3$), 3-55 (s, 3H, OCH$_3$), 4.40 (d, 1H, J=6.02 Hz, NCH), 5.05 (d, 1H, J=5.8 Hz, OCH), 7.10-7.15 (m, 2H, 2×ArH), 7.42-7.46 (m, 2H, 2×ArH).

$^{13}$C-NMR (CD$_3$OD, δ): 32.4, 57.8, 62.1, 72.1, 116.4 (d, 2×C, J=22.0 Hz), 129.5 (d, 2×C, J=7.7 Hz), 136.8, 164.3 (d, 1C, J=245.0 Hz), 168.2.

MS-ESI m/z (% rel. Int.): 243.2 ([MH]+, 25).

HPLC: Method A, detection UV 210 nm, RT=3.64 min, peak area 97%.

While this invention has been described with respect to these specific examples, it is understood that other modifications and variations are possible without departing from the spirit of the invention.

What is claimed is:
1. A compound represented by the Formula I:

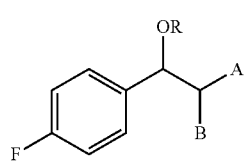

Formula I or a pharmaceutically acceptable salt thereof, wherein:
A is a cyclic amide moiety of the structure:

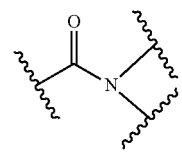

wherein the carbonyl carbon atom directly attaches to the carbon atom of Formula I, and wherein the nitrogen atom attached to the carbonyl of the amide moiety is part of a cycle; and further wherein A has the molecular formula $C_{1-7}O_{1-2}S_{0-1}N_{1-2}H_{2-16}F_{0-2}$;

B is an amine moiety of the structure:

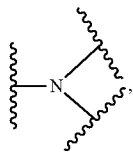

wherein one bond from the nitrogen atom attaches to the carbon atom of Formula I, and the other two bonds from the nitrogen attach to the remainder of the amine moiety; an N-amide moiety of the structure:

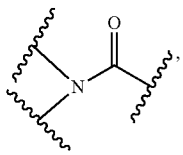

wherein one bond from the nitrogen atom attaches to the carbon atom of Formula I, and the other bond from the nitrogen atom and the bond from the carbonyl carbon attach to the remainder of the N-amide moiety; or a sulfonamide moiety of the structure:

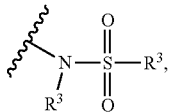

wherein each $R^3$ independently is H or $C_{1-6}$ alkyl; and further wherein B has the molecular formula $C_{1-12}H_{2-30}O_{1-4}S_{0-1}N_{1-3}F_{0-2}Cl_{0-2}Br_{0-2}I_{0-2}$, and R is H, $C_{1-6}$ alkyl, or $C_{1-6}$ acyl.

2. The compound of claim 1 wherein R is H.
3. The compound of claim 2 wherein A is:

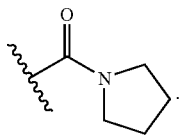

4. The compound of claim 2 wherein B is $NH_2$.
5. The compound of claim 3 wherein B is $NH_2$.
6. A compound of the formula:

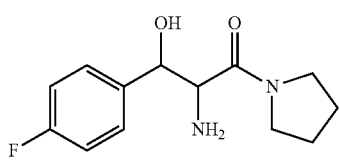

or a pharmaceutically acceptable salt thereof.
7. The compound of claim 6 which is the erythro form.
8. The compound of claim 7 which is the (+)-enantiomer.
9. The compound of claim 7 which is the (−)-enantiomer.
10. The compound of claim 6 which is the threo form.
11. The compound of claim 10 which is the (+)-enantiomer.
12. The compound of claim 10 which is the (−)-enantiomer.
13. A compound selected from the group consisting of:
(±)-threo-2-Amino-3-(4-fluorophenyl)-3-hydroxy-1-(pyrrolidin-1-yl)propan-1-one hydrochloride;
(+)-threo-2-Amino-3-(4-fluorophenyl)-3-hydroxy-1-(pyrrolidin-1-yl)propan-1-one hydrochloride;
(−)-threo-2-Amino-3-(4-fluorophenyl)-3-hydroxy-1-(pyrrolidin-1-yl)propan-1-one hydrochloride;
(±)-erythro-2-Amino-3-(4-fluorophenyl)-3-hydroxy-1-(pyrrolidin-1-yl)propan-1-one hydrochloride;
(+)-erythro-2-Amino-3-(4-fluorophenyl)-3-hydroxy-1-(pyrrolidin-1-yl)propan-1-one hydrochloride;
(−)-erythro-2-Amino-3-(4-fluorophenyl)-3-hydroxy-1-(pyrrolidin-1-yl)propan-1-one hydrochloride;
(±)-threo-2-Amino-3-(4-fluorophenyl)-3-hydroxy-1-(morpholin-4-yl)-propan-1-one hydrochloride;
(±)-threo-2-Amino-3-(4-fluorophenyl)-3-hydroxy-1-(piperidin-1-yl)propan-1-one hydrochloride;
(±)-threo-2-Amino-N,N-diethyl-3-(4-fluorophenyl)-3-hydroxypropanamide hydrochloride;
(±)-threo-2-Amino-3-(4-fluorophenyl)-3-hydroxy-1-(4-methylpiperidin-1-yl)propan-1-one hydrochloride;
(±)-threo-2-Amino-3-(4-fluorophenyl)-3-hydroxy-1-(4-methoxypiperidin-1-yl)propan-1-one hydrochloride;
(±)-threo-2-Amino-1-(azepan-1-yl)-3-(4-fluorophenyl)-3-hydroxypropan-1-one hydrochloride;
(±)-threo-2-Amino-1-(3,3-difluoropyrrolidin-1-yl)-3-(4-fluorophenyl)-3-hydroxypropan-1-one hydrochloride;
(2R,3S)-2-Amino-3-(4-fluorophenyl)-1-((S)-3-fluoropyrrolidin-1-yl)-3-hydroxypropan-1-one hydrochloride and (2S,3R)-2-amino-3-(4-fluorophenyl)-1-((S)-3-fluoropyrrolidin-1-yl)-3-hydroxypropan-1-one hydrochloride in ratio (1:1);
(±)-threo-2-(Benzylamino)-3-(4-fluorophenyl)-3-hydroxy-1-(pyrrolidin-1-yl)propan-1-one hydrochloride;
(±)-threo-2-(3,4-Dichlorobenzylamino)-3-(4-fluorophenyl)-3-hydroxy-1-(pyrrolidin-1-yl)propan-1-one hydrochloride;
(1S,2R)-2-Amino-1-(4-fluorophenyl)-3-oxo-3-(pyrrolidin-1-yl)propyl acetate hydrochloride; and
(±)-threo-2-Amino-3-(4-fluorophenyl)-3-hydroxy-N-methoxy-N-methylpropanamide hydrochloride; or any other pharmaceutically acceptable salt thereof.
14. A method of treating pain comprising administering a compound according to claim 1 or a pharmaceutically acceptable salt thereof to a mammal in need thereof.
15. A dosage form comprising at least one compound according to claim 1, or a pharmaceutically acceptable salt thereof, and at least one pharmaceutically acceptable excipient.
16. The compound of claim 1, wherein A is selected from the group consisting of:

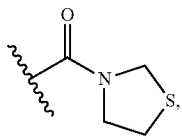 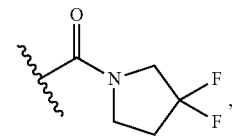

-continued
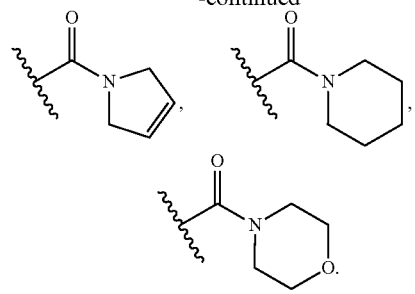
17. The compound of claim 1, wherein B is an N-amide moiety and is selected from the group consisting of:
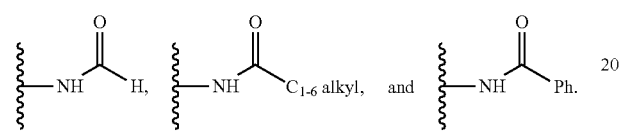
18. A compound selected from the group consisting of:
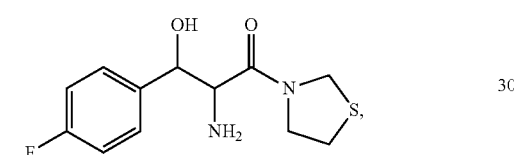
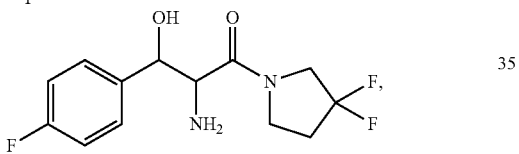
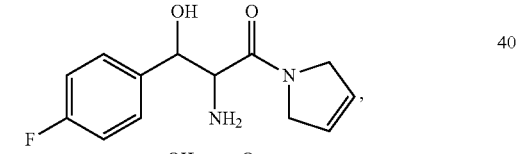
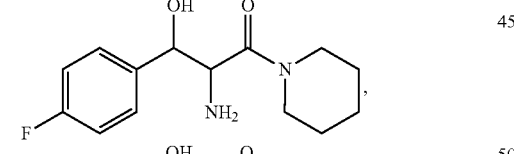
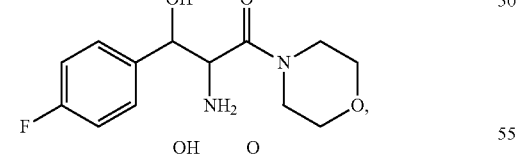
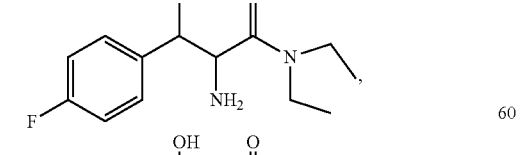
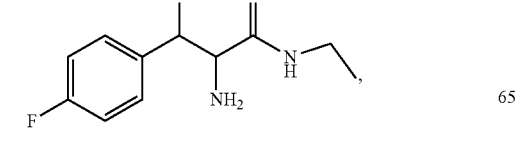
-continued
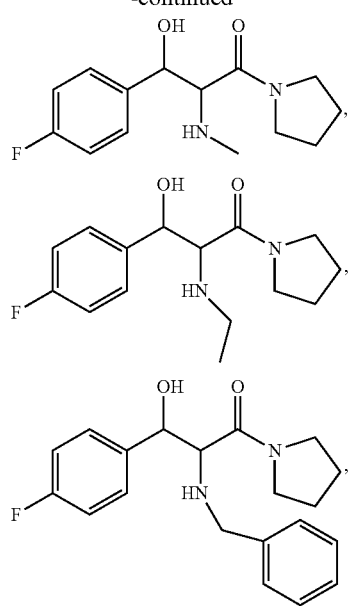
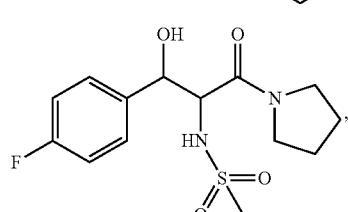
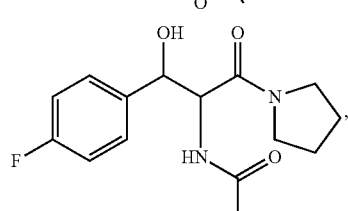
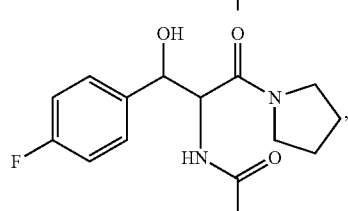
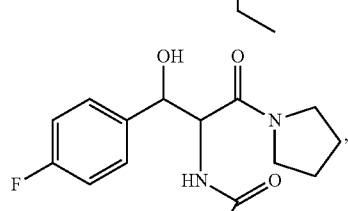
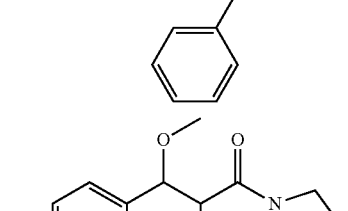

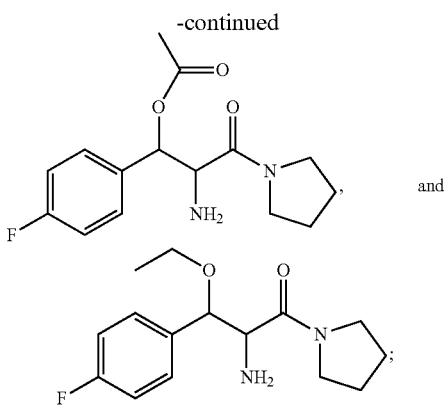 and or a pharmaceutically acceptable salt thereof.

19. A dosage form comprising at least one compound according to claim 6, or a pharmaceutically acceptable salt thereof, and at least one pharmaceutically acceptable excipient.

20. A dosage form comprising at least one compound according to claim 13, or any other pharmaceutically acceptable salt thereof, and at least one pharmaceutically acceptable excipient.

21. A dosage form comprising at least one compound according to claim 18, or a pharmaceutically acceptable salt thereof, and at least one pharmaceutically acceptable excipient.

* * * * *